United States Patent
Eriksson et al.

(10) Patent No.: US 7,754,750 B2
(45) Date of Patent: Jul. 13, 2010

(54) METALLOPROTEINASE INHIBITORS

(75) Inventors: Anders Eriksson, Lund (SE); Matti Lepistö, Lund (SE); Michael Lundkvist, Lund (SE); Magnus Munck Af Rosenschöld, Lund (SE); Pavol Zlatoidsky, Lund (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/115,785

(22) Filed: May 6, 2008

(65) Prior Publication Data
US 2008/0306065 A1    Dec. 11, 2008

Related U.S. Application Data

(62) Division of application No. 10/471,900, filed as application No. PCT/SE02/00472 on Mar. 13, 2002, now Pat. No. 7,427,631.

(30) Foreign Application Priority Data
Mar. 15, 2001    (SE)    ................................ 0100902

(51) Int. Cl.
*A61K 31/4178* (2006.01)
*A61K 31/454* (2006.01)
*A61K 31/4545* (2006.01)
*A61K 31/496* (2006.01)
*C07D 403/14* (2006.01)
*C07D 403/12* (2006.01)
*C07D 211/96* (2006.01)
*C07D 401/14* (2006.01)

(52) U.S. Cl. .................. 514/385; 514/333; 514/253.09; 544/370; 544/360; 546/211; 546/210; 546/193; 548/314.7

(58) Field of Classification Search ............ 514/253.09, 514/333, 385; 544/370, 360; 546/193, 210, 546/211; 548/314.7
See application file for complete search history.

(56) References Cited

U.S. PATENT DOCUMENTS

| | | | |
|---|---|---|---|
| 2,327,890 A | 8/1943 | Henze | |
| 2,745,875 A | 5/1956 | Ehrhart et al. | |
| 3,452,040 A | 6/1969 | Langis | |
| 3,529,019 A | 9/1970 | Suh et al. | |
| 3,849,574 A | 11/1974 | Suh et al. | |
| 4,241,073 A | 12/1980 | Jamieson et al. | |
| 4,315,031 A | 2/1982 | Vincent et al. | |
| 4,983,771 A | 1/1991 | Bryker et al. | |
| 5,068,187 A | 11/1991 | Takeichi et al. | |
| 5,246,943 A | 9/1993 | Blankley et al. | |
| 5,308,853 A | 5/1994 | Hodges et al. | |
| 5,521,187 A | 5/1996 | Freyne et al. | |
| 5,804,593 A | 9/1998 | Warpehoski et al. | |
| 5,919,790 A | 7/1999 | Allen et al. | |
| 5,955,435 A | 9/1999 | Baxter et al. | |
| 6,046,214 A | 4/2000 | Kristiansen et al. | |
| 6,048,841 A | 4/2000 | Baxter et al. | |
| 6,114,361 A | 9/2000 | Robinson et al. | |
| 6,159,995 A | 12/2000 | Thorwart et al. | |
| 6,166,041 A | 12/2000 | Cavalla et al. | |
| 6,218,418 B1 | 4/2001 | Pevarello et al. | |
| 6,268,379 B1 | 7/2001 | Xue et al. | |
| 6,277,987 B1 | 8/2001 | Kukkola et al. | |
| 6,291,685 B1 | 9/2001 | Junghans et al. | |
| 6,329,418 B1 | 12/2001 | Cheng et al. | |
| 6,339,101 B1 | 1/2002 | Ross et al. | |
| 6,340,691 B1 | 1/2002 | Levin et al. | |
| 6,429,213 B1 | 8/2002 | Xue et al. | |
| 6,890,915 B2 | 5/2005 | Sheppeck et al. | |
| 6,906,053 B2 | 6/2005 | Sheppeck et al. | |
| 7,078,424 B2 | 7/2006 | Hamilton et al. | |
| 7,132,434 B2 | 11/2006 | Eriksson et al. | |
| 7,354,940 B2 | 4/2008 | Henriksson et al. | |
| 7,368,465 B2 | 5/2008 | Eriksson et al. | |
| 7,427,631 B2 | 9/2008 | Eriksson et al. | |
| 2002/0006920 A1 | 1/2002 | Robinson et al. | |
| 2002/0028835 A1 | 3/2002 | Hu et al. | |
| 2002/0065219 A1 | 5/2002 | Naidu et al. | |
| 2002/0091107 A1 | 7/2002 | Madar et al. | |
| 2003/0130273 A1 | 7/2003 | Sheppeck et al. | |
| 2004/0044215 A1 | 3/2004 | Alcade et al. | |
| 2004/0106659 A1 | 6/2004 | Af Rosenschold | |
| 2004/0110809 A1 | 6/2004 | Lepisto et al. | |
| 2004/0116486 A1 | 6/2004 | Lepisto et al. | |
| 2004/0138276 A1 | 7/2004 | Eriksson et al. | |
| 2004/0147573 A1 | 7/2004 | Eriksson et al. | |

(Continued)

FOREIGN PATENT DOCUMENTS

EP    0175312    3/1986

(Continued)

OTHER PUBLICATIONS

Reisner, D.B. J. Am. Chem. Soc. 1956, 78, 5102-4. The CAS abstract and search structure are provided.*

(Continued)

*Primary Examiner*—Rebecca L Anderson
*Assistant Examiner*—Jason Nolan
(74) *Attorney, Agent, or Firm*—Fish & Richardson P.C.

(57) ABSTRACT

Compounds of the formula (I) wherein z is $SO_2$ or SO, useful as metalloproteinase inhibitors, especially as inhibitors of MMP12.

3 Claims, No Drawings

U.S. PATENT DOCUMENTS

| | | |
|---|---|---|
| 2004/0152697 A1 | 8/2004 | Chan et al. |
| 2004/0209874 A1 | 10/2004 | Sheppeck et al. |
| 2004/0266832 A1 | 12/2004 | Li et al. |
| 2005/0019994 A1 | 1/2005 | Chang |
| 2005/0026990 A1 | 2/2005 | Eriksson et al. |
| 2005/0171096 A1 | 8/2005 | Sheppeck et al. |
| 2005/0245586 A1 | 11/2005 | Henriksson et al. |
| 2005/0256176 A1 | 11/2005 | Burrows et al. |
| 2006/0019994 A1 | 1/2006 | Burrows et al. |
| 2006/0063818 A1 | 3/2006 | Burrows et al. |
| 2006/0276524 A1 | 12/2006 | Henriksson et al. |
| 2008/0004317 A1 | 1/2008 | Gabos et al. |
| 2008/0032997 A1 | 2/2008 | Gabos et al. |
| 2008/0064710 A1 | 3/2008 | Gabos et al. |
| 2008/0171882 A1 | 7/2008 | Eriksson et al. |
| 2008/0221139 A1 | 9/2008 | Chapman et al. |
| 2008/0262045 A1 | 10/2008 | Eriksson et al. |
| 2008/0293743 A1 | 11/2008 | Gabos et al. |
| 2008/0306065 A1 | 12/2008 | Eriksson et al. |
| 2009/0054659 A1 | 2/2009 | Cornwall et al. |

FOREIGN PATENT DOCUMENTS

| | | |
|---|---|---|
| EP | 0212617 | 3/1987 |
| EP | 0255390 | 2/1988 |
| EP | 0442584 | 8/1991 |
| EP | 0486280 | 5/1992 |
| EP | 0580210 | 1/1994 |
| EP | 0640594 | 3/1995 |
| EP | 0709375 | 5/1996 |
| EP | 0741724 | 11/1996 |
| EP | 0909754 | 4/1999 |
| EP | 1117616 | 7/2001 |
| EP | 1149843 | 10/2001 |
| EP | 1191024 | 3/2002 |
| EP | 02741724 | 3/2004 |
| EP | 1550725 | 7/2005 |
| WO | WO 92/01062 | 1/1992 |
| WO | WO 95/14025 | 5/1995 |
| WO | WO 96/21640 | 7/1996 |
| WO | WO 96/27583 | 9/1996 |
| WO | WO 98/50359 | 11/1998 |
| WO | WO 99/06361 | 2/1999 |
| WO | WO 99/24399 | 5/1999 |
| WO | WO 99/42443 | 8/1999 |
| WO | WO 99/62880 | 12/1999 |
| WO | WO 00/09103 | 2/2000 |
| WO | WO 00/12477 | 3/2000 |
| WO | WO 00/12478 | 3/2000 |
| WO | WO 00/35886 | 6/2000 |
| WO | WO 00/40577 | 7/2000 |
| WO | WO 00/44770 | 8/2000 |
| WO | WO 00/75106 | 12/2000 |
| WO | WO 01/05756 | 1/2001 |
| WO | WO 01/12189 | 2/2001 |
| WO | WO 01/22363 | 3/2001 |
| WO | WO 01/34573 | 5/2001 |
| WO | WO 02/06232 | 1/2002 |
| WO | WO 02/14262 | 2/2002 |
| WO | WO 02/14354 | 2/2002 |
| WO | WO 02/20515 | 3/2002 |
| WO | WO 02/74748 | 9/2002 |
| WO | WO 02/74749 | 9/2002 |
| WO | WO 02/74750 | 9/2002 |
| WO | WO 02/74751 | 9/2002 |
| WO | WO 02/74752 | 9/2002 |
| WO | WO 02/74767 | 9/2002 |
| WO | WO 02/96426 | 12/2002 |
| WO | WO 03/040098 | 5/2003 |
| WO | WO 03/087057 | 10/2003 |
| WO | WO 03/093260 | 11/2003 |
| WO | WO 03/094919 | 11/2003 |
| WO | WO 2004/020415 | 3/2004 |
| WO | WO 2004/024060 | 3/2004 |
| WO | WO 2004/024698 | 3/2004 |
| WO | WO 2004/024715 | 3/2004 |
| WO | WO 2004/024718 | 3/2004 |
| WO | WO 2004/024721 | 3/2004 |
| WO | WO 2004/033632 | 4/2004 |
| WO | WO 2004/108086 | 12/2004 |
| WO | WO 2006/004532 | 1/2006 |
| WO | WO 2006/004533 | 1/2006 |
| WO | WO 2006/065215 | 6/2006 |
| WO | WO 2006/065216 | 6/2006 |
| WO | WO 2006/077387 | 7/2006 |
| WO | WO 2007/106021 | 9/2007 |
| WO | WO 2007/106022 | 9/2007 |

OTHER PUBLICATIONS

Avgeropoulos et al., "New Treatment Strategies for Malignant Gliomas", *The Oncologist* 4:209-224 (1999).

Borkakoti, "Matrix metalloprotease inhibitors: design from structure", *Biochemical Society Transactions* 32:17-20 (2004).

Bruce et al., "The effect of marimastat, a metalloprotease inhibitor, on allergen-induced asthmatic hyper-activity", *Toxicol. & Appl. Pharmacol.* 205:126-132 (2005).

Catterall et al., "Drugs in development: bisphosphonates and metalloproteinase inhibitors", *Arthritis Res Ther* 5:12-24 (2003).

Chambers et al., "Changing Views of the Role of Matrix Metalloproteinases in Metastasis", *J Natl Cancer Inst* 89:1260-1270 (1997).

Chodosh et al., "Comparative trials of doxycycline versus amoxicillin, cephalexin and enoxacin in bacterial infections in chronic bronchitis and asthma", *Scand. J. Infect. Dis. Suppl.*53:22-8 (1988).

COPD; http://www.lungsonline.com/copd.html, downloaded Aug. 22, 2008.

Demedts et al., "Elevated MMP-12 protein levels in induced sputum from patients with COPD", *Thorax* 61:196-201 (2006).

Dormán et al., "MMP Inhibitors in Cardiac Diseases: An Update", *Recent Patents on Cardiovascular Drug Discovery* 2:000-000 (2007).

Dorwald, F.Z., "Side Reactions in Organic Synthesis: A Guide to Successful Synthesis Design", 2005, Wiley-VCH Verlag GmbH & Co. KGaA, Weinheim.

Doxycycline hyclate; http://en.wikipedia.org/wiki/Doxycycline_hyclate, downloaded Aug. 22, 2008.

Hirrlinger et al., "Purification and properties of an amidase from *Rhodococcus erythropolis* MP50 which enantioselectively hydrolyzes 2-arylpropionamides", *J. Bacteriology* 178(12):3501-3507 (1996).

Johnson et al., "Divergent effects of matrix metalloproteinases 3, 7, 9, and 12 on atherosclerotic plaque stability in mouse brachiocephalic arteries", *PNAS* 102(43):15575-15580 (2005).

Kelly et al., "Role of matrix metalloproteinase in asthma", *Current Opinion in Pulmonary Medicine* 9(1):28-33 (2003).

Morris et al., PubMed Abstract, "Sequential steps in hematogenous metastasis of cancer cells studied by in vivo videomicroscopy", *Invasion Metastasis* 17:281-296 (1997).

Murphy et al., "Reappraising metalloproteinases in rheumatoid arthritis and osteoarthritis: destruction or repair?", *Nature Clinical Practice Rheumatology* 4:128-135 (2008).

Rasmussen et al., "Matrix Metalloproteinase Inhibition as a Novel Anticancer Strategy: A Review with Special Focus on Batimastat and Marimastat", *Pharmacol. Ther.* 75:69-75 (1997).

Reisner, "Some α-amino acids containing a sulfonamide group", *J. Am. Chem. Soc.* 78:5102-5104 (1956). CAS abstract and search structure only.

Simone, "Oncology: Introduction", Cecil Textbook of Medicine, 20th Edition, vol. 1, pp. 1004-1010 (1996).

Smith, Michael B., Organic Synthesis Second Edition, 3.9.A Oxidation of sulfur compounds, McGraw-Hill 2002, ISBN-0-07-048242-X, p. 280.

Visse et al., "Matrix Metalloproteinases and Tissue Inhibitors of Metalloproteinases", *Circ Res*. 92:827-839 (2003).

Wikipedia, Matrix metalloproteinase, updated Mar. 9, 2009, <http://en.wikipedia.org/wiki/Matrix_metalloproteinase>, downloaded Mar. 11, 2009.

Wikipedia, Minocycline, updated Feb. 28, 2009, http://en.wikipedia.org/wiki/Minocycline, downloaded Mar. 11, 2009.

Aigner et al., "Growth Plate Cartilage as Developmental Model in Osteoarthritis Research—Potentials and Limitations", *Current Drug Targets* 8(2):377-385 (2007).

Banfield et al., "Heterocyclic Derivatives of Guanidine. Part V. Reaction of Some Glycidic Esters with Guanidines", *The Journal of the Chemical Society* 511:2747-2756 (1963).

Belvisi et al., "The role of matrix metalloproteinases (MMPs) in the patho-physiology of chronic obstructive pulmonary disease (COPD): a therapeutic role for inhibitors of MMPs?", *Inflammation Research* 52:95-100 (2003).

Borchers et al., "Acrolein-Induced MUC5ac Expression in Rat Airways", *The American Physiological Society* 274:L573-L581 (1998).

Carmeliet, "Proteinases in Cardiovascular Aneurysms and Rupture: Targets for Therapy?", *The Journal of Clinical Investigation* 105(11):1519-1520 (2000).

Comber et al., "5,5-Disubstituted Hydantoins: Syntheses and Anti-Hiv Activity", *J. Med. Chem*. 35:3567-3572 (1992).

Dahan et al., "Expression of Matrix Metalloproteinases in Healthy and Diseased Human Gingiva", *Journal of Clinical Periodontology* 28:128-136 (2001).

Doherty et al., "Therapeutic Developments in Matrix Metalloproteinase Inhibition", *Expert Opinion Ther. Patents* 12(5):665-707 (2002).

Elliot et al., "The Clinical Potential of Matrix Metalloproteinase Inhibitors in the Rheumatic Disorders", *Drugs & Aging* 18(2):87-99 (2001).

Fujita et al., "The pathogenesis of COPD: Lessons Learned from in vivo Animal Models", *Med. Sci Monit*. 13(2):RA19-24 (2007).

Gramatica et al., STN International, HCAPLUS Database, Columbus, OH, Accession No. 2002:356947, Reg. No. 36734-19-7 2002.

Hautamaki et al., "Requirement for Macrophage Elastase for Cigarette Smoke-Induced Emphysema in Mice", *Science* 277:2002-2004 (2002).

Lindy et al., "Matrix Metalloproteinase 13 (Collagenase 3) in Human Rheumatoid Synovium Arthritis Rheumatism," *Arthritis and Rheumatism* 40(8):1391-1399 (1997).

MacFadyen, "Can Matrix Metalloproteinase Inhibitors Provide a Realistic Therapy in Cardiovascular Medicine", *Current Opinion in Pharmacology* 7:171-178 (2007).

Mandal, Malay et al., "*Clinical Implications of Matrix Metalloproteinases*", *Molecular and Cellular Biochemistry*, 252:305-329, (2003).

PubMed Abstract (provided in enclosed Office Actions) for: Rifkin, B.R. et al, "Blocking Periodontal Disease Progression by Inhibiting Tissue-Destructive Enzymes: A Potential Therapeutic Role for Tetracyclines and Their Chemically-Modified Analogs", Periodontol, Aug. 1993 64 (8 Suppl), pp. 819-827 (see Rifkin below).

Pyo et al., "Targeted gene disruption of matrix metalloproteinase-9 (gelatinase B) suppresses development of experimental abdominal aortic aneurysms", *J. Clinical Investigation* 105:1641-1649 (2000).

Rouis et al, "Adenovirus-mediated overexpression of tissue inhibitor of metalloproteinase-1 reduces atherosclerotic lesions in apolipoprotein E-deficient mice", *Circulation* 100:533-540 (1999).

Rifkin et al, "Blocking Periodontal Disease Progression by Inhibiting Tissue-Destructive Enzymes: A Potential Therapeutic Role for Tetracyclines and Their Chemically-Modified Analogs", Periodontol Aug. 1993 64 (8 Suppl), pp. 819-827.

Wernicke, Dirk et al., "*Cloning of Collagenase 3 from the Synovial Membrane and Its Expression in Rheumatoid Arthritis and Osteoarthritis*", *The Journal of Rheumatology*, 23:590-595, (1996).

Whittaker, Mark et al., "*Design and Therapeutic Application of Matrix Metalloproteinase Inhibitors*", *Chemical Reviews*, 99:2735-2776, (1999).

Wingerchuk, Dean M. et al., "Multiple Sclerosis: Current Pathophysiological Concepts", Biology of Disease, Lab Invest 2001, vol. 81, pp. 263-281.

Aharony et al. "Pharmacological Characterization of a New Class of Nonpeptide Neurokinin A Antagonists that Demonstrate Species Selectivity." J. Pharmacol. Exp. Ther. 274:3 (1995), pp. 1216-1221.

Aimoto et al. "Synthesis of Carriers of Differing Strokes Radius with Activated Acyl Groups for Use as Reagents in Labeling Membrane Proteins." Journal of Biological Chemistry, vol. 256(10), pp. 5134-5143, 1981.

Chemical Abstracts, vol. 65, 1966, Abstract No. 13684 h, M. Lora-Tamayo et al.: "Potential anticancer agents. I. Glutamine sulfonate analogs", & Anales Real Soc. Espan. Fis. Quim (Madrid), Ser. B. 62(2), 173-86.

Croce, P. et al. "Stereoselective aldol addition of a chirai glycine enloate synthon to heteroaromatic aldehydes." Heterocycles, 52:3 (2000) pp. 1337-1344,.

Knabe, J. "Razemate and enantiomere basisch substituierter 5-phenylhydantoine." Pharmazie. 52:12 (1997) pp. 912-919.

Bright et al. "Monoclonal Antibodies as Surrogate Receptors in High Throughput Screen for Compounds that Enhance Insulin Sensitivity." Life Sciences. 61:23 (1997), pp. 2305-2315.

Lora-Tamayo et al. "Anticancerousos Potenciales." An. Quim 64:6 (1968), pp. 591-606.

Michaelides et al., "Recent Advances in Matrix Metalloproteinase Inhibitors Research", *Current Pharmaceutical Design* 5:787-819 (1999).

Miyake, Toshiaki et al. "Studies on Glycosylation of erythro-Beta-Hydroxy-L-histidine. A Key Step of Blemycin Total Synthesis." Bull. Chem. Soc. Jpn. 59 (1986), pp. 1387-1395.

Mock et al., "Principles of Hydroxamate Inhibition of Metalloproteases: Carboxypeptidase A", *Biochemistry* 39:13945-13952 (2000).

Nakajima, Riichiro et al. "The utility of 4-(2-thienyl)pyridines as a derivatization reagent for hplc and ce." Analytical Sciences. 7, Supplement 1991, pp. 177-180.

Nicolet, Ben. "Interpretation of the Dyhydration of Acetylglutamic acid by Means of Glutamylthiohydantoin Derivatives." Journal of the American Chemical Society, 1930, pp. 1192-1195.

Owa, Takashi et al. "Man-Designed Bleomycins: Significance of the binding Sites as Enzyme Models and of the Stereochemistry of the Linker Moiety." Tetrahedron. 48:7 (1992) pp. 1193-1208.

Peng, Sean X. "Separation and identification of methods for metalloproteinase inhibitors." Journal of Chromatography B. 764 (2001), pp. 59-80.

Saito, Sei-ichi et al. "A new synthesis of deglyco-bleomycine A2 aiming at the total synthesis of bleomycin." Tetrahedron Letters. 23(5) (1982), pp. 529-532.

STN International, file CAPLUS, accession No. 1978:424767, Raulais, Daniel J.P., "Synthesis and characterization of phenylthiohydantoin derivatives of amino-acids protected in their sid-chain functions, and their application for monitoring olid-phase peptide synthesis," & Journal of Chemical Research, Synopses (1978), p. 11.

STN International, file CAPLUS, accession No. 1994:299315, Document No. 120:299315, Sakamoto, Shuichi et al., "Preparation of pyridylserine derivatives as psychotropics," WO, A1, 9320053, 19931014, See CAS RN 154696-31-8, 154697-48-0. 1994.

STN International, file CAPLUS, accession No. 1997:644516, Batty, Craig et al. "Synthesis and exchange reaction of 5-alkyl-2oxo-6-thioxo-1,2,3,6-hexahydropyrimidine-4-carboxylic acids" & Journal of Heterocyclic Chemistry (1997), 34:3, 1355-1367.

STN International, file CAPLUS, accession No. 2002:640897, Gooding, Owen W. et al. "Use of Statistical Design of Experiments in the Optimization of Amide Synthesis Utilizing Polystryene-Supported N-Hydroxybenzotriazole Resin" & Journal of Combinatorial Chemistry (2002), 4(6), 576-583.

STN International, File CAPLUS, CAPLUS accession No. 1968:506154, Doc. No. 69:106154, Lora-Tamayo, J. et al.: "Potential anticancer agents, VI. Sulfonic analogs of aspartic acid", & An. Quim. (1968), 64(6), 591-606.

STN International, File CAPLUS, CAPLUS accession No. 1974:463633, Doc. No. 81:63633, Blaha, Ludvik et al.: "5-Methyl-5-phenoxymethyl-hydantoins", & CS 151744, B, 19731119 1973.

STN International, File CAPLUS, CAPLUS accession No. 1988:631020, Doc. No. 8109:231020, Mitsui Toatsu Chemicals, Inc.: "Process for the preparation of 5-benzylhdantoins as intermediates for aromatic amino acids": & JP, A2, 63079879, 19880409 1988.

STN International, File CAPLUS, CAPLUS accession No. 1989:173366, Doc. No. 110:173366, Oh, Chang Hyun et al., "Synthesis of new hydantoin-3-acetic acid derivatives", & Bull. Korean Chem. Soc. (1988), 9(4), 231-5.

STN International, File CAPLUS, CAPLUS accession No. 1990:138955, Doc. No. 112:138955, Crooks, Peter A. et al.: "Synthesis of 5-benzoyl-5-phenyl-and-5-(Phenylhydroxymethyl)-5-phenythydantoins as potential anticonvulsants"; & J. Heterocycl. Chem. (1989), 26(4), 1113-17.

* cited by examiner

METALLOPROTEINASE INHIBITORS

CROSS REFERENCE TO RELATED APPLICATIONS

This application is a divisional of U.S. application Ser. No. 10/471,900, filed on Jan. 14, 2004, now U.S. Pat. No. 7,427,631, which is the National Stage of International Application No.: PCT/SE02/00472, filed on Mar. 13, 2002, which claims the benefit of Swedish Application No.: SE 0100902-6, filed on Mar. 15, 2001. Each of these prior filed applications is incorporated herein by reference in its entirety.

The present invention relates to compounds useful in the inhibition of metalloproteinases and in particular to pharmaceutical compositions comprising these, as well as their use.

The compounds of this invention are inhibitors of one or more metalloproteinase enzymes. Metalloproteinases are a superfamily of proteinases (enzymes) whose numbers in recent years have increased dramatically. Based on structural and functional considerations these enzymes have been classified into families and subfamilies as described in N. M. Hooper (1994) FEBS Letters 354:1-6. Examples of metalloproteinases include the matrix metalloproteinases (MMPs) such as the collagenases (MMP1, MMP8, MMP13), the gelatinases (MMP2, MMP9), the stromelysins (MP3, MMP10, MMP11), matrilysin (MMP7), metalloelastase (MMP12), enamelysin (MMP19), the MT-MMPs (MMP14, MMP15, MMP16, MMP17); the reprolysin or adamalysin or MDC family which includes the secretases and sheddases such as TNF converting enzymes (ADAM10 and TACE); the astacin family which include enzymes such as procollagen processing proteinase (PCP); and other metalloproteinases such as aggrecanase, the endothelin converting enzyme family and the angiotensin converting enzyme family.

Metalloproteinases are believed to be important in a plethora of physiological disease processes that involve tissue remodelling such as embryonic development, bone formation and uterine remodelling during menstruation. This is based on the ability of the metalloproteinases to cleave a broad range of matrix substrates such as collagen, proteoglycan and fibronectin. Metalloproteinases are also believed to be important in the processing, or secretion, of biological important cell mediators, such as tumour necrosis factor (TNF); and the post translational proteolysis processing, or shedding, of biologically important membrane proteins, such as the low affinity IgE receptor CD23 (for a more complete list see N. M. Hooper et al., (1997) Biochem J. 321:265-279).

Metalloproteinases have been associated with many diseases or conditions. Inhibition of the activity of one or more metalloproteinases may well be of benefit in these diseases or conditions, for example: various inflammatory and allergic diseases such as, inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis); in tumour metastasis or invasion; in disease associated with uncontrolled degradation of the extracellular matrix such as osteoarthritis; in bone resorptive disease (such as osteoporosis and Paget's disease); in diseases associated with aberrant angiogenesis; the enhanced collagen remodelling associated with diabetes, periodontal disease (such as gingivitis), corneal ulceration, ulceration of the skin, postoperative conditions (such as colonic anastomosis) and dermal wound healing; demyelinating diseases of the central and peripheral nervous systems (such as multiple sclerosis); Alzheimer's disease; extracellular matrix remodelling observed in cardiovascular diseases such as restenosis and atherosclerosis; asthma; rhinitis; and chronic obstructive pulmonary diseases (COPD).

MMP12, also known as macrophage elastase or metalloelastase, was initially cloned in the mouse by Shapiro et al [1992, Journal of Biological Chemistry 267: 4664] and in man by the same group in 1995. MMP-12 is preferentially expressed in activated macrophages, and has been shown to be secreted from alveolar macrophages from smokers [Shapiro et al, 1993, Journal of Biological Chemistry, 268: 23824] as well as in foam cells in atherosclerotic lesions [Matsumoto et al, 1998, Am J Pathol 153: 109]. A mouse model of COPD is based on challenge of mice with cigarette smoke for six months, two cigarettes a day six days a week. Wildtype mice developed pulmonary emphysema after this treatment. When MMP12 knock-out mice were tested in this model they developed no significant emphysema, strongly indicating that MMP-12 is a key enzyme in the COPD pathogenesis. The role of MMPs such as MMP12 in COPD (emphysema and bronchitis) is discussed in Anderson and Shinagawa, 1999, Current Opinion in Anti-inflammatory and Immunomodulatory Investigational Drugs 1(1): 29-38. It was recently discovered that smoking increases macrophage infiltration and macrophage-derived MMP-12 expression in human carotid artery plaques Kangavari [Matetzky S, Fishbein M C et al., Circulation 102:(18) 36-39 Suppl. S, Oct. 31, 2000].

MMP13, or collagenase 3, was initially cloned from a cDNA library derived from a breast tumour [J. M. P. Freije et al. (1994) Journal of Biological Chemistry 269(24):16766-16773]. PCR-RNA analysis of RNAs from a wide range of tissues indicated that MMP13 expression was limited to breast carcinomas as it was not found in breast fibroadenomas, normal or resting mammary gland, placenta, liver, ovary, uterus, prostate or parotid gland or in breast cancer cell lines (T47-D, MCF-7 and ZR75-1). Subsequent to this observation MMP13 has been detected in transformed epidermal keratinocytes [N. Johansson et al., to (1997) Cell Growth Differ. 8(2):243-250], squamous cell carcinomas [N. Johansson et al., (1997) Am. J. Pathol. 151(2):499-508] and epidermal tumours [K. Airola et al., (1997) J. Invest. Dermatol. 109(2):225-231]. These results are suggestive that MMP13 is secreted by transformed epithelial cells and may be involved in the extracellular matrix degradation and cell-matrix interaction associated with metastasis especially as observed in invasive breast cancer lesions and in malignant epithelia growth in skin carcinogenesis.

Recent published data implies that MMP13 plays a role in the turnover of other connective tissues. For instance, consistent with MMP13's substrate specificity and preference for degrading type II collagen [P. G. Mitchell et al., (1996) J. Clin. Invest: 97(3):761-768; V. Knauper et al., (1996) The Biochemical Journal 271:1544-1550], MMP13 has been hypothesized to serve a role during primary ossification and skeletal remodelling [M. Stahle-Backdahl et al., (1997) Lab. Invest. 76(5):717-728; N. Johansson et al., (1997) Dev. Dyn. 208(3):387-397], in destructive joint diseases such as rheumatoid and osteo-arthritis [D. Wernicke et al., (1996) J. Rheumatol. 23:590-595; P. G. Mitchell et al., (1996) J. Clin. Invest. 97(3):761-768; O. Lindy et al., (1997) Arthritis Rheum 40(8): 1391-1399]; and during the aseptic loosening of hip replacements [S. Imai et al., (1998) J. Bone Joint Surg. Br. 80(4): 701-710]. MMP13 has also been implicated in chronic adult periodontitis as it has been localised to the epithelium of chronically inflamed mucosa human gingival tissue [V. J. Uitto et al., (1998) Am. J. Pathol 152(6):1489-1499] and in remodelling of the collagenous matrix in chronic wounds [M. Vaalamo et al., (1997) J. Invest. Dermatol. 109(1):96-101].

MMP9 (Gelatinase B; 92 kDa TypeIV Collagenase; 92 kDa Gelatinase) is a secreted protein which was first purified, then cloned and sequenced, in 1989 [S. M. Wilhelm et al (1989) J. Biol. Chem. 264 (29): 17213-17221; published erratum in J. Biol. Chem. (1990) 265 (36): 22570]. A recent review of MMP9 provides an excellent source for detailed information and references on this protease: T. H. Vu & Z. Werb (1998) (In: Matrix Metalloproteinases. 1998. Edited by W. C. Parks & R. P. Mecham. pp 115-148. Academic Press. ISBN 0-12-545090-7). The following points are drawn from that review by T. H. Vu & Z. Werb (1998).

The expression of MMP9 is restricted normally to a few cell types, including trophoblasts, osteoclasts, neutrophils and macrophages. However, it's expression can be induced in these same cells and in other cell types by several mediators, including exposure of the cells to growth factors or cytokines. These are the same mediators often implicated in initiating an inflammatory response. As with other secreted MMPs, MMP9 is released as an inactive Pro-enzyme which is subsequently cleaved to form the enzymatically active enzyme. The proteases required for this activation in vivo are not known. The balance of active MMP9 versus inactive enzyme is further regulated in vivo by interaction with TIMP-1 (Tissue Inhibitor of Metalloproteinases-1), a naturally-occurring protein. TIMP-1 binds to the C-terminal region of MMP9, leading to inhibition of the catalytic domain of MMP9. The balance of induced expression of ProMMP9, cleavage of Pro- to active MMP9 and the presence of TIMP-1 combine to determine the amount of catalytically active MMP9 which is present at a local site. Proteolytically active MMP9 attacks substrates which include gelatin, elastin, and native Type IV and Type V collagens; it has no activity against native Type I collagen, proteoglycans or laminins.

There has been a growing body of data implicating roles for MMP9 in various physiological and pathological processes. Physiological roles include the invasion of embryonic trophoblasts through the uterine epithelium in the early stages of embryonic implantation; some role in the growth and development of bones; and migration of inflammatory cells from the vasculature into tissues.

MMP-9 release, measured using enzyme immunoassay, was significantly enhanced in fluids and in AM supernatants from untreated asthmatics compared with those from other populations [Am. J. Resp. Cell & Mol. Biol., November 1997, 17 (5):583-591]. Also, increased MMP9 expression has been observed in certain other pathological conditions, thereby implicating MMP9 in disease processes such as COPD, arthritis, tumour metastasis, Alzheimer's, Multiple Sclerosis, and plaque rupture in atherosclerosis leading to acute coronary conditions such as Myocardial Infarction.

MMP-8 (collagenase-2, neutrophil collagenase) is a 53 kD enzyme of the matrix metalloproteinase family that is preferentially expressed in neutrophils. Later studies indicate MMP-8 is expressed also in other cells, such as osteoarthritic chondrocytes [Shlopov et al, 1997, Arthritis Rheum, 40:2065]. MMPs produced by neutrophils can cause tissue remodelling, and hence blocking MM-8 should have a positive effect in fibrotic diseases of for instance the lung, and in degradative diseases like pulmonary emphysema. MMP-8 was also found to be up-regulated in osteoarthritis, indicating that blocking MMP-8 many also be beneficial in this disease.

MMP-3 (stromelysin-1) is a 53 kD enzyme of the matrix metalloproteinase enzyme family. MMP-3 activity has been demonstrated in fibroblasts isolated from inflamed gingiva [Uitto V. J. et al, 1981, J. Periodontal Res., 16:417-424], and enzyme levels have been correlated to the severity of gum disease [Overall C. M. et al, 1987, J. Periodontal Res., 22:81-88]. MMP-3 is also produced by basal keratinocytes in a variety of chronic ulcers [Saarialho-Kere U. K. et al, 1994, J. Clin. Invest., 94:79-88]. MMP-3 mRNA and protein were detected in basal keratinocytes adjacent to but distal from the wound edge in what probably represents the sites of proliferating epidermis. MMP-3 may thus prevent the epidermis from healing. Several investigators have demonstrated consistent elevation of MMP-3 in synovial fluids from rheumatoid and osteoarthritis patients as compared to controls [Walakovits L. A. et al, 1992, Arthritis Rheum., 35:35-42; Zafarullah M. et al, 1993, J. Rheumnatol., 20:693-697]. These studies provided the basis for the belief that an inhibitor of MMP-3 will treat diseases involving disruption of extracellular matrix resulting in inflammation due to lymphocytic infiltration, or loss of structural integrity necessary for organ function.

A number of metalloproteinase inhibitors are known (see for example the review of MMP inhibitors by Beckett R. P. and Whittaker M., 1998, Exp. Opin. Ther. Patients, 8(3):259-282]. Different classes of compounds may have different degrees of potency and selectivity for inhibiting various metalloproteinases.

Whittaker M. et al (1999, Chemical Reviews 99(9):2735-2776] review a wide range of known MMP inhibitor compounds. They state that an effective MMP inhibitor requires a zinc binding group or ZBG (functional group capable of chelating the active site zinc(II) ion), at least one functional group which provides a hydrogen bond interaction with the enzyme backbone, and one or more side chains which undergo effective van der Waals interactions with the enzyme subsites. Zinc binding groups in known MMP inhibitors include carboxylic acid groups, hydroxamic acid groups, sulfhydryl or mercapto, etc. For example, Whittaker M. et al discuss the following MMP inhibitors:

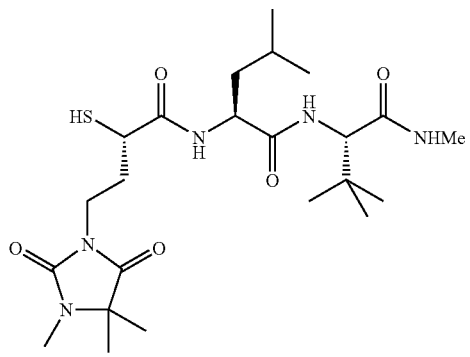

The above compound entered clinical development. It has a mercaptoacyl zinc binding group, a trimethylhydantoinyl-ethyl group at the P1 position and a leucinyl-tert-butyllglycinyl backbone.

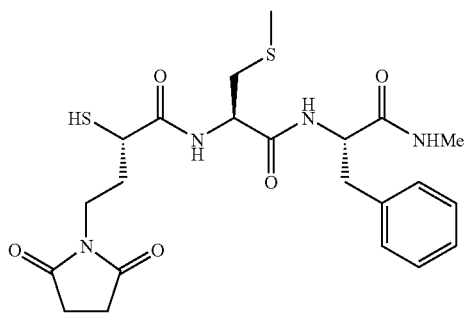

The above compound has a mercaptoacyl zinc binding group and an imide group at the P1 position.

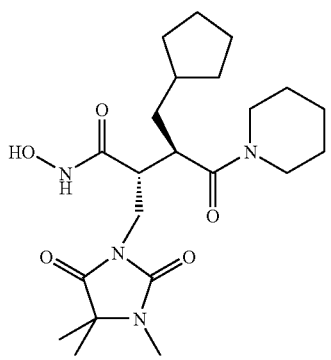

The above compound was developed for the treatment of arthritis. It has a non-peptidic succinyl hydroxamate zinc binding group and a trimethylhydantoinylethyl group at the P1 position.

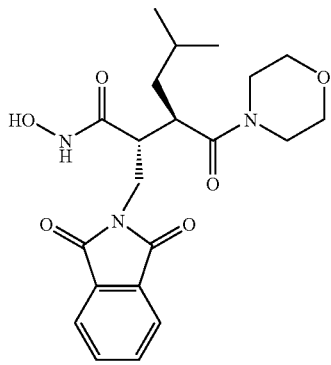

The above compound is a phthalimido derivative that inhibits collagenases. It has a non-peptidic succinyl hydroxamate zinc binding group and a cyclic imide group at P1. Whittaker M. et al also discuss other MMP inhibitors having a P1 cyclic imido group and various zinc binding groups (succinyl hydroxamate, carboxylic acid, thiol group, phosphorous-based group).

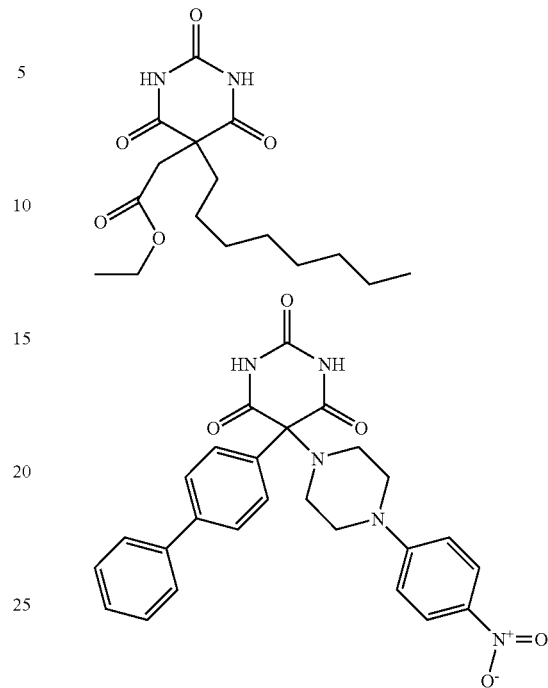

The above compounds appear to be good inhibitors of MMP8 and MMP9 (PCT patent applications WO9858925, WO9858915). They have a pyrimidin-2,3,4-trione zinc binding group.

The following compounds are not known as MMP inhibitors:—

Lora-Tamayo, M et al (1968, An. Quim 64(6): 591-606) describe synthesis of the following compounds as a potential anti-cancer agent:

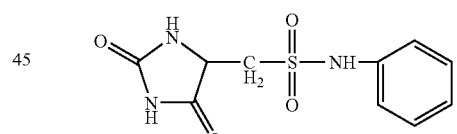

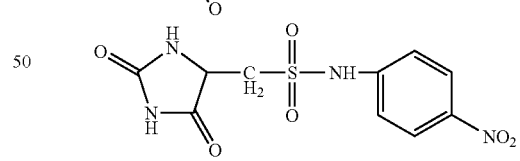

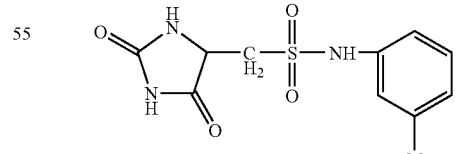

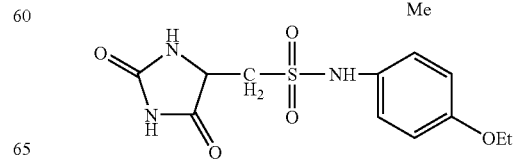

Czech patent numbers 151744 (19731119) and 152617 (1974022) describe the synthesis and the anticonvulsive activity of the following compounds:

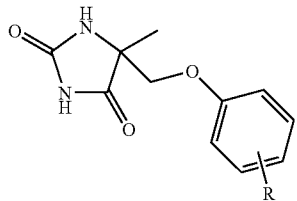

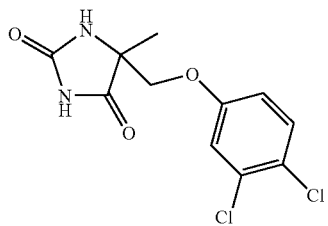

R = 4-N02, 4-OMe, 2-NO2,

U.S. Pat. No. 3,529,019 (19700915) describes the following compounds used as intermediates:

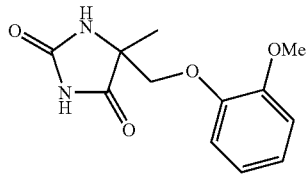

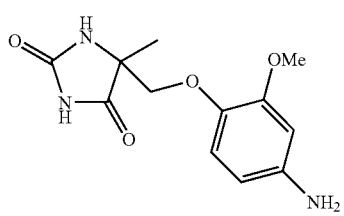

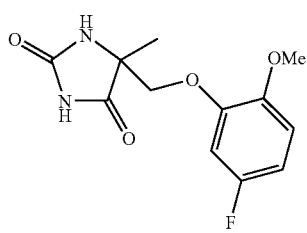

PCT patent application number WO 00/09103 describes compounds useful for treating a vision disorder, including the following (compounds 81 and 83, Table A, page 47):

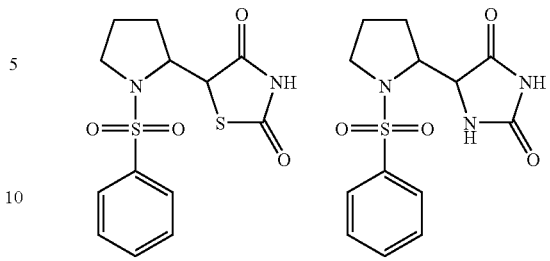

We have now discovered a new class of compounds that are inhibitors of metalloproteinases and are of particular interest in inhibiting MMPs such as MMP-12. The compounds are metalloproteinase inhibitors having a metal binding group that is not found in known metalloproteinase inhibitors. In particular, we have discovered compounds that are potent MMP12 inhibitors and have desirable activity profiles. The compounds of this invention have beneficial potency, selectivity and/or pharmacokinetic properties.

The metalloproteinase inhibitor compounds of the invention comprise a metal binding group and one or more other functional groups or side chains characterised in that the metal binding group has the formula (k).

(k)

wherein X is selected from NR1, O, S;
Y1 and Y2 are independently selected from O, S;
R1 is selected from H, alkyl, haloalkyl;

Any alkyl groups outlined above may be straight chain or branched; any alkyl group outlined above is preferably (C1-7)alkyl and most preferably (C1-6)alkyl.

A metalloproteinase inhibitor compound is a compound that inhibits the activity of a metalloproteinase enzyme (for example, an MMP). By way of non-limiting example the inhibitor compound may show IC50s in vitro in the range of 0.1-10000 nanomolar, preferably 0.1-1000 nanomolar.

A metal binding group is a functional group capable of binding the metal ion within the active site of the enzyme. For example, the metal binding group will be a zinc binding group in MMP inhibitors, binding the active site zinc(II) ion. The metal binding group of formula (k) is based on a five-membered ring structure and is preferably a hydantoin group, most preferably a –5 substituted 1-H,3-H-imidazolidine-2,4-dione.

In a first aspect of the invention we now provide compounds of the formula I

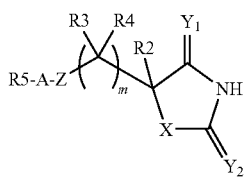

wherein
X is selected from NR1, O, S;
Y1 and Y2 are independently selected from O, S;
Z is selected from SO, $SO_2$;
m is 1 or 2;
A is selected from a direct bond, (C1-6)alkyl, (C1-6)haloalkyl, or (C1-6)heteroalkyl containing a hetero group selected from N, O, S, SO, SO2 or containing two hetero groups selected from N, O, S, SO, SO2 and separated by at least two carbon atoms;
R1 is selected from H, (C1-3)alkyl, haloalkyl;
Each R2 and R3 is independently selected from H, halogen (preferably fluorine), alkyl, heteroalkyl, cycloalkyl, heterocycloalkyl, aryl, heteroaryl, alkylaryl, alkyl-heteroaryl, heteroalkyl-aryl, heteroalkyl-heteroaryl, aryl-alkyl, aryl-heteroalkyl, heteroaryl-alkyl, heteroaryl-heteroalkyl, aryl-aryl, aryl-heteroaryl, heteroaryl-aryl, heteroaryl-heteroaryl, cycloalkyl-alkyl, heterocycloalkyl-alkyl, alkylcycloalkyl, alkyl-heterocycloalkyl;
Each R4 is independently selected from H, halogen (preferably fluorine), (C1-3)alkyl or haloalkyl;
Each of the R2 and R3 radicals may be independently optionally substituted with one or more (preferably one) groups selected from alkyl, heteroalkyl, aryl, heteroaryl, halo, haloalkyl, hydroxy, alkoxy, haloalkoxy, thiol, alkylthiol, arylthiol, alkylsulfon, haloalkylsulfon, arylsulfon, aminosulfon, N-alkylaminosulfon, N,N-dialkylaminosulfon, arylaminosulfon, amino, N-alkylamino, N,N-dialkylamino, amido, N-alkylamido, N,N-dialkylamido, cyano, sulfonamino, alkylsulfonamino, arylsulfonamino, amidino, N-aminosulfon-amidino, guanidino, N-cyano-guanidino, thioguanidino, 2-nitro-ethene-1,1-diamin, carboxy, alkyl-carboxy, nitro, carbamate;
Optionally R2 and R3 may join to form a ring comprising up to 7 ring atoms, or R2 and R4 may join to form a ring comprising up to 7 ring atoms, or R3 and R4 may join to form a ring comprising up to 7 ring atoms;
R5 is a monocyclic, bicyclic or tricyclic group comprising one, two or three ring structures each of up to 7 ring atoms independently selected from cycloalkyl, aryl, heterocycloalkyl or heteroaryl, with each ring structure being independently optionally substituted by one or more substituents independently selected from halogen, hydroxy, alkyl, alkoxy, haloalkoxy, amino, N-alkylamino, N,N-dialkylamino, alkylsulfonamino, alkylcarboxyamino, cyano, nitro, thiol, alkylthiol, alkylsulfonyl, haloalkylsulfonyl, alkylaminosulfonyl, carboxylate, alkylcarboxylate, aminocarboxy, N-alkylamino-carboxy, N,N-dialkylamino-carboxy, wherein any alkyl radical within any substituent may itself be optionally substituted with one or more groups selected from halogen, hydroxy, alkoxy, haloalkoxy, amino, N-alkylamino, N,N-dialkylamino, N-alkylsulfonamino, N-alkylcarboxyamino, cyano, nitro, thiol, alkylthiol, alkylsulfonyl, N-alkylamino-sulfonyl, carboxylate, alkylcarboxy, aminocarboxy, N-alkylaminocarboxy, N,N-dialkylaminocarboxy, carbamate;
when R5 is a bicyclic or tricyclic group, each ring structure is joined to the next ring structure by a direct bond, by —O—, by (C1-6)alkyl, by (C1-6)haloalkyl, by (C1-6)heteroalkyl, by (C1-6)alkenyl, by (C1-6)alkynyl, by sulfone, by CO, by NCO, by CON, by NH, by S, by C(OH) or is fused to the next ring structure;
Any heteroalkyl group outlined above is a hetero atom-substituted alkyl containing one or more hetero groups independently selected from N, O, S, SO, SO2, (a hetero group being a hetero atom or group of atoms);
Any heterocycloalkyl or heteroaryl group outlined above contains one or more hetero groups independently selected from N, O, S, SO, SO2;
Any alkyl, alkenyl or alkynyl groups outlined above may be straight chain or branched; unless otherwise stated, any alkyl group outlined above is preferably (C1-7)alkyl and most preferably (C1-6)alkyl.
Preferred compounds of the formula I are those wherein any one or more of the following apply:
X is NR1;
Z is $SO_2$ or SO; especially Z is $SO_2$;
At least one of Y1 and Y2 is O; especially both Y1 and Y2 are O;
m is 1;
R1 is H, (C1-3) alkyl, (C1-3) haloalkyl; especially R1 is H, (C1-3)alkyl; most especially R1 is H;
R2 is H, alkyl, hydroxyalkyl, alkoxyalkyl, aryloxy alkyl, aminoalkyl, cycloalkyl-alkyl, alkyl-cycloalkyl, arylalkyl, alkylaryl, alkyl-heteroaryl, heteroalkyl, heterocycloalkyl-alkyl, alkyl-heterocycloalkyl, heteroaryl-alkyl, heteroalkyl-aryl; especially R2 is alkyl, aminoalkyl, alkyl-heteroaryl, alkyl-heterocycloalkyl or heteroaryl-alkyl.
R3 and/or R4 is H;
R3 and/or R4 is methyl;
R5 comprises one, two or three optionally substituted aryl or heteroaryl 5 or 6 membered rings;
R5 is a bicyclic or tricyclic group comprising two or three optionally substituted ring structures.
Particularly preferred compounds of formula I are those wherein R5 is a bicyclic or tricyclic group comprising two or three optionally substituted ring structures.
The invention further provides compounds of the formula II

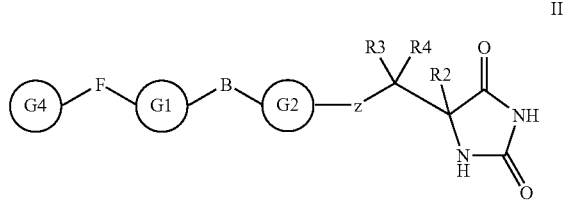

wherein
each of G1, G2 and G4 is a monocyclic ring structure comprising each of up to 7 ring atoms independently selected from cycloalkyl, aryl, heterocycloalkyl or heteroaryl, with each ring structure being independently optionally substituted by one or two substituents independently selected from halogen, hydroxy, haloalkoxy, amino, N-alkylamino, N,N-dialkylamino, cyano, nitro, alkyl, alkoxy, alkyl sulfone, haloalkyl sulfone, alkylcarbamate, allylamide, wherein any alkyl radical within any substituent may itself be optionally substituted with one or more groups selected from halogen, hydroxy, amino, N-alkylamino, N,N-dialkylamino, cyano, nitro, alkoxy, haloalkoxy, aryloxy, heteroaryloxy, carbamate;

Z is SO$_2$;

Each of B and F is independently selected from a direct bond, O, (C1-6)alkyl, (C1-6)heteroalkyl, alkynyl, CO, NCO, CON, NH, S;

R2 is selected from H, alkyl, hydroxyalkyl, alkoxyalkyl, aryloxy alkyl, aminoalkyl, (N-alkylamino)alkyl, (N,N-dialkylamino)alkyl, amidoalkyl, thioalkyl cycloalkyl-alkyl, alkyl-cycloalkyl, arylalkyl, alkylaryl, alkyl-heteroaryl, heteroalkyl, heterocycloalkyl-alkyl, alkyl-heterocycloalkyl, heteroaryl-alkyl, heteroalkyl-aryl;

R3 and R4 are independently selected from H or (C1-3)alkyl;

Optionally R2 and R3 may join to form a ring comprising up to 7 ring atoms, or R2 and R4 may join to form a ring comprising up to 7 ring atoms, or R3 and R4 may join to form a ring comprising up to 7 ring atoms;

Any heteroalkyl group outlined above is a hetero atom-substituted alkyl containing one or more hetero groups independently selected from N, O, S, SO, SO$_2$, (a hetero group being a hetero atom or group of atoms);

Any heterocycloalkyl or heteroaryl group outlined above contains one or more hetero groups independently selected from N, O, S, SO, SO2;

Any alkyl, alkenyl or alkynyl groups outlined above may be straight chain or branched; unless otherwise stated, any alkyl group outlined above is preferably (C1-7)alkyl and most preferably (C1-6)alkyl.

Preferred compounds of the formula II include those wherein R2 is alkyl, aminoalkyl, alkyl-heteroaryl, alkyl-heterocycloalkyl or heteroaryl-alkyl.

The invention further provides compounds of the formula IIa

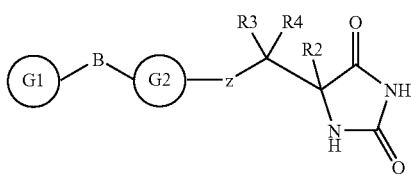

wherein each of G1 and G2 is a monocyclic ring structure comprising each of up to 7 ring atoms independently selected from cycloalkyl, aryl, heterocycloalkyl or heteroaryl, with each ring structure being independently optionally substituted by one or two substituents independently selected from halogen, hydroxy, haloalkoxy, amino, N-alkylamino, N,N-dialkylamino, cyano, nitro, alkyl, alkoxy, alkyl sulfone, haloalkyl sulfone, alkylcarbamate, alkylamide, wherein any alkyl radical within any substituent may itself be optionally substituted with one or more groups selected from halogen, hydroxy, amino, N-alkylamino, N,N-dialkylamino, cyano, nitro, alkoxy, haloalkoxy, aryloxy, heteroaryloxy, carbamate;

Z is SO$_2$;

B is selected from a direct bond, O, (C1-6)alkyl, (C1-6)heteroalkyl, CO, NCO, CON, NH, S, alkynyl;

R2 is selected from H, (C1-6)alkyl, haloalkyl, hydroxyalkyl, alkoxyalkyl, aminoalkyl, (N-alkylamino)alkyl, (N,N-dialkylamino)alkyl, amidoalkyl, thioalkyl, or R2 is a group of formula III

C and D are independently selected from a direct bond, H, (C1-C6)alkyl, (C1-C6)haloalkyl, or (C1-C6)heteroalkyl containing one or two hetero atoms selected from N, O or S such that when two hetero atoms are present they are separated by at least two carbon atoms;

G3 is a monocyclic ring structure comprising up to 7 ring atoms independently selected from cycloalkyl, aryl, heterocycloalkyl or heteroaryl, optionally substituted by one or two substituents independently selected from halogen, hydroxy, amino, N-alkylamino, N,N-dialkylamino, cyano, nitro, alkyl, alkoxy, alkyl sulfone, haloalkyl sulfone, or alkyl substituted with one or more groups selected from halogen, hydroxy, amino, N-alkylamino, N,N-dialkylamino, cyano, nitro, alkoxy, haloalkoxy;

Optionally R2 is substituted with halo, haloalkyl, hydroxy, alkoxy, haloalkoxy, amino, aminoalkyl, N-alkylamino, N,N-dialkylamino, (N-alkylamino)alkyl, (N,N-dialkylamino)alkyl, alkylsulfone, aminosulfone, N-alkylamino-sulfone, N,N-dialkylamino-sulfone, amido, N-alkylamido, N,N-dialkylamido, cyano, sulfonamino, alkyl-sulfonamino, amidino, N-aminosulfone-amidino, guanidino, N-cyano-guanidino, thioguanidino, 2-nitroguanidino, carboxy, alkylcarboxy, carbamate;

R3 and R4 are independently selected from H or (C1-3)alkyl;

Optionally R2 and R3 may join to form a ring comprising up to 7 ring atoms, or R2 and R4 may join to form a ring comprising up to 7 ring atoms, or R3 and R4 may join to form a ring comprising up to 7 ring atoms;

Any heteroalkyl group outlined above is a hetero atom-substituted alkyl containing one or more hetero groups independently selected from N, O, S, SO, SO2, (a hetero group being a hetero atom or group of atoms);

Any heterocycloalkyl or heteroaryl group outlined above contains one or more hetero groups independently selected from N, O, S, SO, SO2;

Any alkyl, alkenyl or alkynyl groups outlined above may be straight chain or branched; unless otherwise stated, any alkyl group outlined above is preferably (C1-7)alkyl and most preferably (C1-6)alkyl.

Preferred compounds of the formula IIa are those wherein one or more of the following apply:

B is selected from a direct bond, O, CO, S, alkynyl; especially B is a direct bond, O, S, or alkynyl;

R2 is selected from H, (C1-6)alkyl, aryl-C1-6)alkyl or heteroaryl-(C1-6)alkyl optionally substituted with halo, haloalkyl, hydroxy, alkoxy, haloalkoxy, amino, aminoalkyl, N-alkylamino, N,N-dialkylamino, N-alkylamino)alkyl, (N,N-dialkylamino)alkyl, alkylsulfone, aminosulfone, N-alkylamino-sulfone, N,N-dialkylamino-sulfone, amido, N-alkylamido, N,N-dialkylamido, carbamate, cyano, sulfonamino, alkyl-sulfonamino, amidino, N-aminosulfone-amidino, guanidino, N-cyano-guanidino, thioguanidino, 2-nitroguanidino, 2-nitro-ethene-1,1-diamino, carboxy, alkylcarboxy, carbamate;

Each of R3 and R4 is H;

G2 is a nitrogen containing six-membered ring;

G1 is para substituted.

Particularly preferred compounds of formula IIa are those wherein each of R3 and R4 is H.

For example, particular compounds of the invention include compounds of formula IIa wherein B is a direct bond, O, S or alkynyl; and R2 is selected from H, (C1-6)alkyl, aryl-(C1-6)alkyl or heteroaryl-C1-6)alkyl optionally substituted with cycloalkyl, heterocycloalkyl, halo, haloalkyl, hydroxy, alkoxy, aryloxy, haloalkoxy, amino, aminoalkyl, N-alkylamino, N,N-dialkylamino, (N-alkylamino)alkyl, (N,N-dialkylamino)alkyl, alkylsulfonyl, aminosulfonyl, N-alkylamino-sulfonyl, N,N-dialkylamino-sulfonyl, amido, N-alkylamido, N,N-dialkylamido, cyano, sulfonamino, alkyl-sulfonamino, amidino, N-aminosulfone-amidino, guanidino, N-cyano-guanidino, thioguanidino, 2-nitroguanidino, carbamate, carboxy, alkylcarboxy; and each of R3 and R4 is H.

Particularly preferred compounds of the invention are those of Formula IIb:

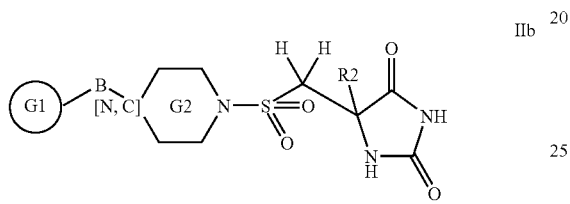

IIb wherein G2 is optionally substituted piperidine or piperazine, and G1, B, and R2 are as described for Formula IIa.

In a compound of Formula IIb, preferably G2 is unsubstituted and G1 is optionally substituted, preferably G1 is para substituted.

Suitable values for R2 include the following:

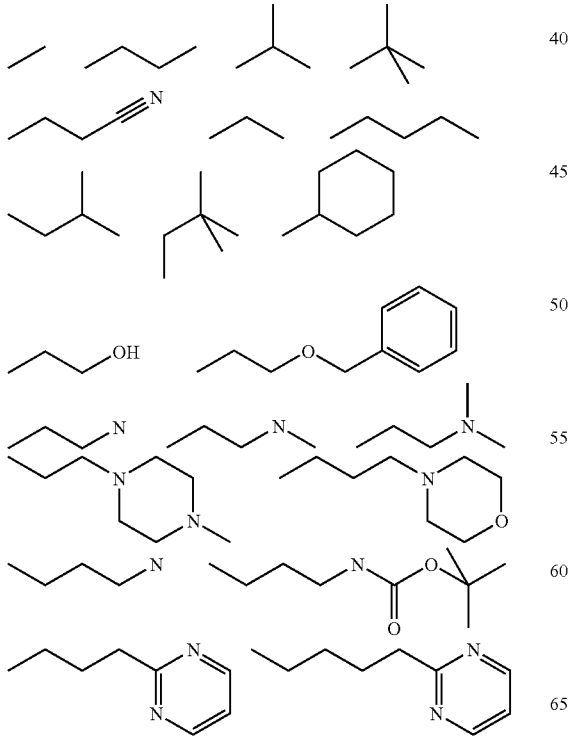

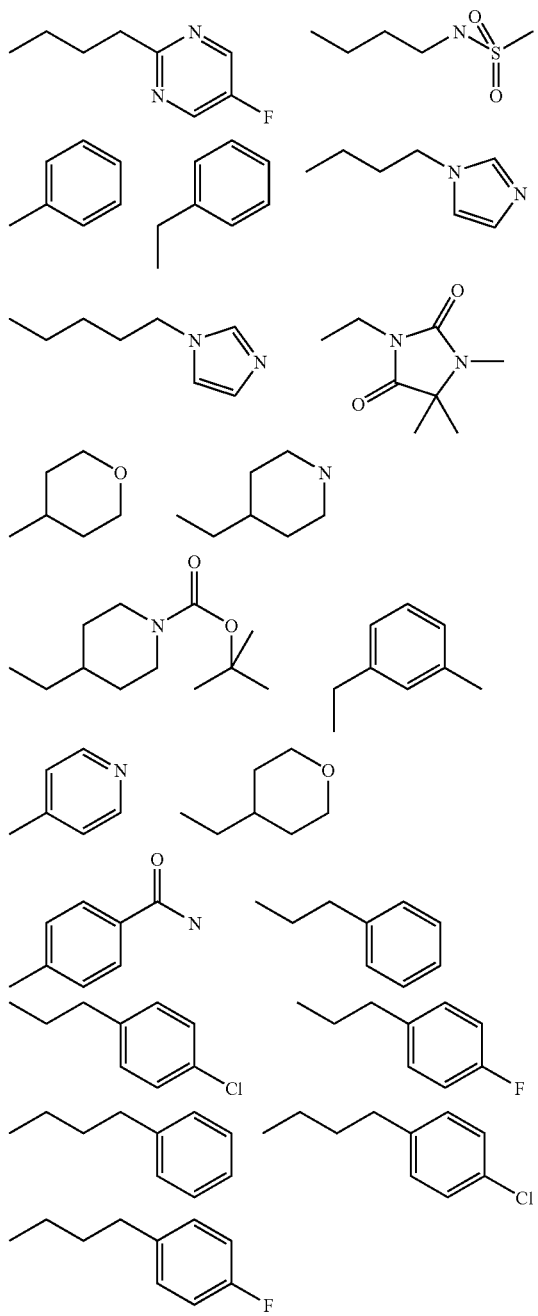

Suitable values for R5 include the following:

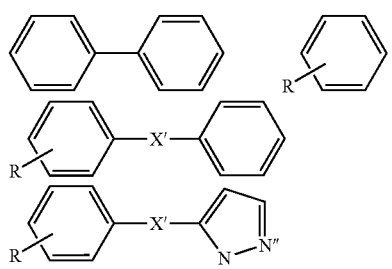

-continued

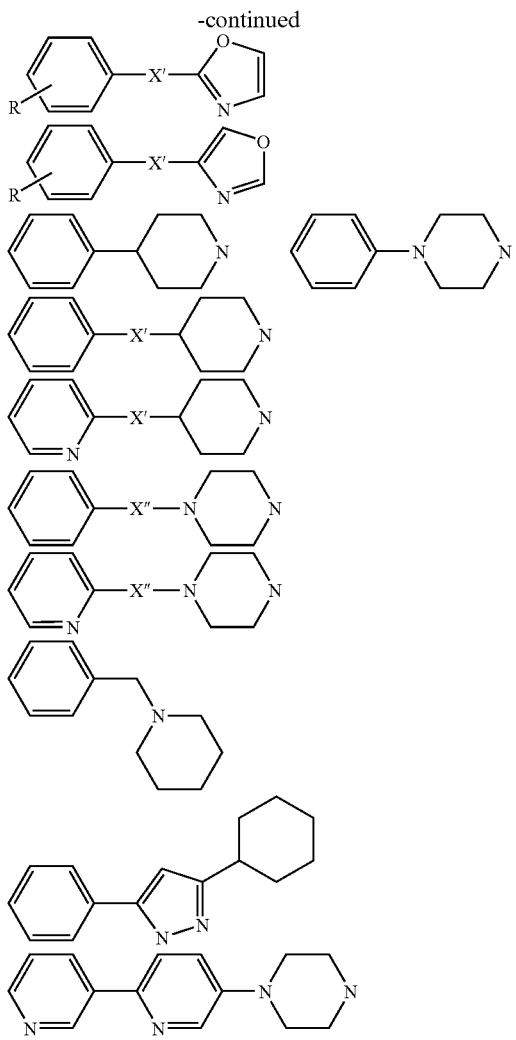

X'=bond, O, CH2, CHF, CF2, S, SO2, CO
X"=bond, CH2; CHF, CF2; SO2, CO
R=F, Cl, Br, CF3, CF3O, CH3O, OH, CF3CH2

It will be appreciated that the particular substituents and number of substituents in compounds of the invention are selected so as to avoid sterically undesirable combinations.

Each exemplified compound represents a particular and independent aspect of the invention.

Where optically active centres exist in the compounds of the invention, we disclose all individual optically active forms and combinations of these as individual specific embodiments of the invention, as well as their corresponding racemates. Racemates may be separated into individual optically active forms using known procedures (cf. Advanced Organic Chemistry: 3rd Edition: author J March, p 104-107) including for example the formation of diastereomeric derivatives having convenient optically active auxiliary species followed by separation and then cleavage of the auxiliary species.

It will be appreciated that the compounds according to the invention may contain one or more asymmetrically substituted carbon atoms. The presence of one or more of these asymmetric centres (chiral centres) in a compound of the invention can give rise to stereoisomers, and in each case the invention is to be understood to extend to all such stereoisomers, including enantiomers and diastereomers, and mixtures including racemic mixtures thereof.

Where tautomers exist in the compounds of the invention, we disclose all individual tautomeric forms and combinations of these as individual specific embodiments of the invention.

As previously outlined the compounds of the invention are metalloproteinase inhibitors, in particular they are inhibitors of MMP12. Each of the above indications for the compounds of the invention represents an independent and particular embodiment of the invention.

Certain compounds of the invention are of particular use as inhibitors of MMP13 and/or MMP9 and/or MMP8 and/or MMP3.

Compounds of the invention show a favourable selectivity profile. Whilst we do not wish to be bound by theoretical considerations, the compounds of the invention are believed to show selective inhibition for any one of the above indications relative to any MMP1 inhibitory activity, by way of non-limiting example they may show 100-1000 fold selectivity over any MMP1 inhibitory activity.

The compounds of the invention may be provided as pharmaceutically acceptable salts. These include acid addition salts such as hydrochloride, hydrobromide, citrate and maleate salts and salts formed with phosphoric and sulphuric acid. In another aspect suitable salts are base salts such as an alkali metal salt for example sodium or potassium, an alkaline earth metal salt for example calcium or magnesium, or organic amine salt for example triethylamine.

They may also be provided as in vivo hydrolysable esters. These are pharmaceutically acceptable esters that hydrolyse in the human body to produce the parent compound. Such esters can be identified by administering, for example intravenously to a test animal, the compound under test and subsequently examining the test animal's body fluids. Suitable in vivo hydrolysable esters for carboxy include methoxymethyl and for hydroxy include formyl and acetyl, especially acetyl.

In order to use a metalloproteinase inhibitor compound of the invention (a compound of the formula I or II, IIa or IIb) or a pharmaceutically acceptable salt or in vivo hydrolysable ester thereof for the therapeutic treatment (including prophylactic treatment) of mammals including humans, it is normally formulated in accordance with standard pharmaceutical practice as a pharmaceutical composition.

Therefore in another aspect the present invention provides a pharmaceutical composition which comprises a compound of the invention (a compound of the formula I or II, IIa or IIb) or a pharmaceutically acceptable salt or an in vivo hydrolysable ester and pharmaceutically acceptable carrier.

The pharmaceutical compositions of this invention may be administered in standard manner for the disease or condition that it is desired to treat, for example by oral, topical, parenteral, buccal, nasal, vaginal or rectal administration or by inhalation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more diseases or conditions referred to hereinabove.

The pharmaceutical compositions of this invention will normally be administered to humans so that, for example, a daily dose of 0.5 to 75 mg/kg body weight (and preferably of 0.5 to 30 mg/kg body weight) is received. This daily dose may be given in divided doses as necessary, the precise amount of the compound received and the route of administration depending on the weight, age and sex of the patient being treated and on the particular disease or condition being treated according to principles known in the art.

Typically unit dosage forms will contain about 1 mg to 500 mg of a compound of this invention.

Therefore in a further aspect, we provide a compound of the formula I or a pharmaceutically acceptable salt or in vivo hydrolysable ester thereof for use in a method of therapeutic treatment of the human or animal body or for use as a therapeutic agent. We disclose use in the treatment of a disease or condition mediated by one or more metalloproteinase enzymes. In particular we disclose use in the treatment of a disease or condition mediated by MMP12 and/or MMP13 and/or MMP9 and/or MMP8 and/or MMP3; especially use in the treatment of a disease or condition mediated by MMP12 or MMP9; most especially use in the treatment of a disease or condition mediated by MMP12.

In particular we provide a compound of the formula II, IIa or IIb or a pharmaceutically acceptable salt or in vivo hydrolysable ester thereof for use in a method of therapeutic treatment of the human or animal body or for use as a therapeutic agent (such as use in the treatment of a disease or condition mediated by MMP12 and/or MMP13 and/or MMP9 and/or MMP8 and/or MMP3; especially MMP12 or MMP9; most especially MMP12).

In yet a further aspect we provide a method of treating a metalloproteinase mediated disease or condition which comprises administering to a warm-blooded animal a therapeutically effective amount of a compound of the formula I or a pharmaceutically acceptable salt or in vivo hydrolysable ester thereof. We also disclose the use of a compound of the formula I or a pharmaceutically acceptable salt or in vivo hydrolysable precursor thereof in the preparation of a medicament for use in the treatment of a disease or condition mediated by one or more metalloproteinase enzymes.

For example we provide a method of treating a metalloproteinase mediated disease or condition which comprises administering to a warm-blooded animal a therapeutically effective amount of a compound of the formula II, IIa or IIb (or a pharmaceutically acceptable salt or in vivo hydrolysable ester thereof). We also provide the use of a compound of the formula II, IIa or IIb (or a pharmaceutically acceptable salt or in vivo hydrolysable precursor thereof) in the preparation of a medicament for use in the treatment of a disease or condition mediated by one or more metalloproteinase enzymes.

Metalloproteinase mediated diseases or conditions include asthma, rhinitis, chronic obstructive pulmonary diseases (COPD), arthritis (such as rheumatoid arthritis and osteoarthritis), atherosclerosis and restenosis, cancer, invasion and metastasis, diseases involving tissue destruction, loosening of hip joint replacements, periodontal disease, fibrotic disease, infarction and heart disease, liver and renal fibrosis, endometriosis, diseases related to the weakening of the extracellular matrix, heart failure, aortic aneurysms, CNS related diseases such as Alzheimer's disease and Multiple Sclerosis (MS), hematological disorders.

Preparation of the Compounds of the Invention

In another aspect the present invention provides a process for preparing a compound of the formula I or II, IIa, IIb or a pharmaceutically acceptable salt or in vivo hydrolysable ester thereof, as described in (a) to (d) below. It will be appreciated that many of the relevant starting materials are commercially or otherwise available or may be synthesised by known methods or may be found in the scientific literature.

(a) Compounds of formula I in which Y1 and Y2 are each O, Z is $SO_2$, R2 is as defined in formula I, A is a direct bond and R5 comprises a nitrogen directly attached to Z, or A is (C1-6) N-alkyl, may be prepared by reacting a compound of the formula IV in which R5 is defined as in formula I with the known compounds of the formula V in which X and m are as defined in formula I:

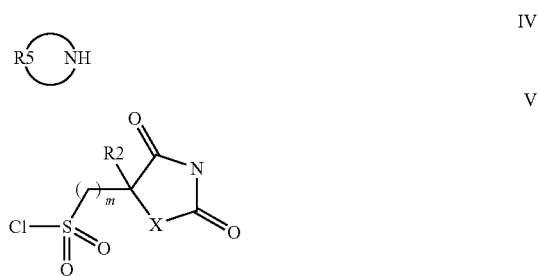

The reaction is preferably performed in suitable solvent optionally in the presence of base for 1 to 24 h at ambient to reflux temperature. Preferably, solvents such as pyridine, dimethylformamide, tetrahydrofurane, acetonitrile or dichloromethane are used with bases like triethylamine, N-methylmorpholine, pyridine or alkali metal carbonates at ambient temperature for 2-16 h reaction time, or until end of reaction is achieved as detected by chromatographic or spectroscopic methods. Reactions of sulfonyl chlorides of formula V with various primary and secondary amines are previously described in the literature, and the variations of the conditions will be evident for those skilled in the art.

Synthesis of compounds of formula V is described in the literature and can be prepared from e.g. cystein or homocystein (Mosher, J.: J. Org. Chem. 23, 1257 (1958). Sulfonylchlorides of formula V, in which m=1, X=NR1 (R1=H) and R2 is as described in formula I, are conveniently prepared by oxidative chlorination of compounds of formula Va, in which R2 is as described in formula I (Griffith, O.: J. Biol. Chem., 1983, 258, 3, 1591).

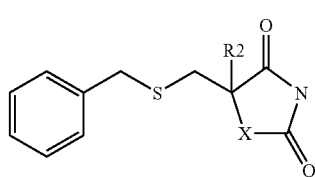

(b) Compounds of formula I in which Y1 and Y2 are each O, Z is S, and X and R5 are as described in formula I may be prepared by reacting a compound of formula VI in which K is a leaving group (e.g chloride, or sulfonate ester) and R5 as described in formula I,

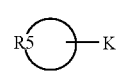

-continued

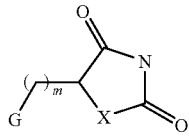
VII with a compound of formula VII, in which G is a sulfhydryl (SH), X and m as described in formula I. The reaction is preferably performed in the presence of base such as diethyl isopropyl amine or cesium carbonate and in the presence of a suitable solvent e.g DMF.

Alternatively, the compounds under process (b) may be prepared in the same manner as in process (b), by reacting the compounds of formula VI and VII, but in which K in compound VI is the sulfhydryl (SH) or a hydroxyl group and G in formula VII represents a leaving group.

(c) Compounds of the formula I in which Y1 and Y2 are each O, Z is SO2 or S(O), and X, A, and R5 are as described in formula I, may be prepared by oxidizing the final products described under process (b) and in which Z is S, with oxidizing agents like peroxide reagents, preferably m-chloroperbenzoic acid or oxone.

(d) Compounds of the formula I in which Y1 and Y2 are each O, X is NR(R1=H), m is 1, and R2, R3, R4, R5 are as described in formula I may be prepared by reacting a compound of formula XI in which R2, R3, R4, R5 and A are as described in formula I,

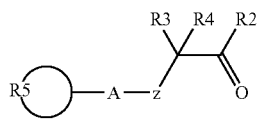
XI with ammonium and cyanide salts in protic solvents, preferably in the presence of excess ammonium carbonate and potassium cyanide in ethanol in a sealed vessel at 40-80 C for 4-24 hours.

The ketones of formula XI are conveniently prepared by treating sulfonamides of formula XII in which R3 is H and R5 is as described in formula I, with excess strong base and then treatment with esters of formula XIII, in which R is an alkyl or aryl residue and R2 are as described for formula I, in non-protic solvents. Preferable conditions are 2-3 equivalents of lithium bases like lithium diisopropylamide or lithium hexamethyldisilazane or butyl lithium in dried etheral solvents like tetrahydrofurane.

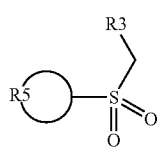
XII

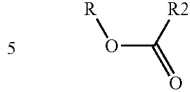
XIII

The ketones of formula XI, in which R3 and R4 are each alkyl or form a ring, R5 is aryl or heteroaryl and R2 is alkyl or aryl, can also be prepared by treating sulfinates of formula XIV in which R5 is aryl or heteroaryl as described in formula I, with a base such as tetrabutylammonium bromide and a ketone of formula XV in which R2 is alkyl or aryl (Crandall et al J. Org. Chem. 1985, (8) 50, 1327-1329). R3 and R4 are then introduced by reaction with alkyl halides or alkyl dihalides. The reaction is preferably performed in the presence of base such as potassium carbonate or caesium carbonate and in the presence of a suitable solvent e.g. DMF or DMSO at 50-10° C.

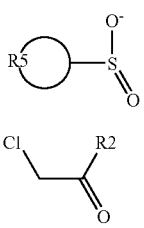

XIV

XV

The compounds of the invention may be evaluated for example in the following assays:

Isolated Enzyme Assays

Matrix Metalloproteinase Family Including for Example MMP12, MMP13.

Recombinant human MMP12 catalytic domain may be expressed and purified as described by Parkar A. A. et al, (2000), Protein Expression and Purification, 20:152. The purified enzyme can be used to monitor inhibitors of activity as follows: MMP12 (50 ng/ml final concentration) is incubated for 30 minutes at RT in assay buffer (0.1M Tris-HCl, pH 7.3 containing 0.1M NaCl, 20 mM $CaCl_2$, 0.040 mM ZnCl and 0.05% (w/v) Brij 35) using the synthetic substrate Mac-Pro-Cha-Gly-Nva-His-Ala-Dpa-NH2 in the presence or absence of inhibitors. Activity is determined by measuring the fluorescence at λex 328 nm and λem 393 nm. Percent inhibition is calculated as follows: % Inhibition is equal to the [$Fluorescence_{plus\ inhibitor}$–$Fluorescence_{background}$] divided by the [$Fluorescence_{minus\ inhibitor}$–$Fluorescence_{background}$].

Recombinant human proMMP13 may be expressed and purified as described by Knauper et al. [V. Knauper et al., (1996) The Biochemical Journal 271:1544-1550 (1996)]. The purified enzyme can be used to monitor inhibitors of activity as follows: purified proMMP13 is activated using 1 mM amino phenyl mercuric acid (APMA), 20 hours at 21° C.; the activated MMP13 (11.25 ng per assay) is incubated for 4-5 hours at 35° C. in assay buffer (0.1M Tris-HCl, pH 7.5 containing 0.1M NaCl, 20 mM $CaCl_2$, 0.02 mM ZnCl and 0.05% (w/v) Brij 35) using the synthetic substrate 7-methoxycoumarin-4-yl)acetyl.Pro.Leu.Gly.Leu.N-3-2,4-dinitrophenyl)-L-2,3-diaminopropionyl.Ala.Arg.NH2 in the presence or absence of inhibitors. Activity is determined by measuring the fluorescence at λex 328 nm and λem 393 nm. Percent inhibition is calculated as follows: % Inhibition is equal to the [Fluorescence$_{plus\ inhibitor}$−Fluorescene$_{background}$] divided by the [Fluorescence$_{minus\ inhibitor}$−Fluorescence$_{background}$].

A similar protocol can be used for other expressed and purified pro MMPs using substrates and buffers conditions optimal for the particular MMP, for instance as described in C. Graham Knight et al., (1992) FEBS Lett. 296(3):263-266.

Adamalysin Family Including for Example TNF Convertase

The ability of the compounds to inhibit proTNFα convertase enzyme may be assessed using a partially purified, isolated enzyme assay, the enzyme being obtained from the membranes of THP-1 as described by K. M. Mohler et al., (1994) Nature 370:218-220. The purified enzyme activity and inhibition thereof is determined by incubating the partially purified enzyme in the presence or absence of test compounds using the substrate 4',5'-Dimethoxy-fluoresceinyl Ser.Pro.Leu.Ala.Gln.Ala.Val.Arg.Ser.Ser.Ser.Arg.Cys(4-(3-succinimid-1-yl)-fluorescein)-NH$_2$ in assay buffer (50 mM Tris HCl, pH 7.4 containing 0.1% (w/v) Triton X-100 and 2 mM CaCl$_2$), at 26° C. for 18 hours. The amount of inhibition is determined as for MMP13 except λex 490 nm and λem 530 nm were used. The substrate was synthesised as follows. The peptidic part of the substrate was assembled on Fmoc-NH-Rink-MBHA-polystyrene resin either manually or on an automated peptide synthesiser by standard methods involving the use of Fmoc-amino acids and O-benzotriazol-1-yl-N,N,N',N'-tetramethyluronium hexafluorophosphate (HBTU) as coupling agent with at least a 4- or 5-fold excess of Fmoc-amino acid and HBTU. Ser$^1$ and Pro$^2$ were double-coupled. The following side chain protection strategy was employed; Ser$^1$(But), Gln$^5$(Trityl), Arg$^{8,12}$(Pmc or Pbf), Ser$^{9,10,11}$(Trityl), Cys$^{13}$(Trityl). Following assembly, the N-terminal Fmoc-protecting group was removed by treating the Fmoc-peptidyl-resin so obtained was acylated by treatment for 1.5-2 hr at 70° C. with 1.5-2 equivalents of 4',5'-dimethoxy-fluorescein-4(5)-carboxylic acid [Khanna & Ullman, (1980) Anal Biochem. 108: 156-161) which had been preactivated with diisopropylcarbodiimide and 1-hydroxybenzotriazole in DMF]. The dimethoxyfluoresceinyl-peptide was then simultaneously deprotected and cleaved from the resin by treatment with trifluoroacetic acid containing 5% each of water and triethylsilane. The dimethoxyfluoresceinyl-peptide was isolated by evaporation, trituration with diethyl ether and filtration. The isolated peptide was reacted with 4-N-maleimido)fluorescein in DMF containing diisopropylethylamine, the product purified by RP-HPLC and finally isolated by freeze-drying from aqueous acetic acid. The product was characterised by MALDI-TOF MS and amino acid analysis.

Natural Substrates

The activity of the compounds of the invention as inhibitors of aggrecan degradation may be assayed using methods for example based on the disclosures of E. C. Arner et al., (1998) Osteoarthritis and Cartilage 6:214-228; (1999) Journal of Biological Chemistry, 274 (10), 6594-6601 and the antibodies described therein. The potency of compounds to act as inhibitors against collagenases can be determined as described by T. Cawston and A. Barrett (1979) Anal. Biochem. 99:340-345.

Inhibition of Metalloproteinase Activity in Cell/Tissue Based Activity

Test as an Agent to Inhibit Membrane Sheddases Such as TNF Convertase

The ability of the compounds of this invention to inhibit cellular processing of TNFα production may be assessed in THP-1 cells using an ELISA to detect released TNF essentially as described K. M. Mohler et al., (1994) Nature 370: 218-220. In a similar fashion the processing or shedding of other membrane molecules such as those described in N. M. Hooper et al., (1997) Biochem. J. 321:265-279 may be tested using appropriate cell lines and with suitable antibodies to detect the shed protein.

Test as an Agent to Inhibit Cell Based Invasion

The ability of the compound of this invention to inhibit the migration of cells in an invasion assay may be determined as described in A. Albini et al., (1987) Cancer Research 47:3239-3245.

Test as an Agent to Inhibit Whole Blood TNF Sheddase Activity

The ability of the compounds of this invention to inhibit TNFα production is assessed in a human whole blood assay where LPS is used to stimulate the release of TNFα. Heparinized (10 Units/ml) human blood obtained from volunteers is diluted 1:5 with medium (RPMI1640+bicarbonate, penicillin, streptomycin and glutamine) and incubated (160 µl) with 20 µl of test compound (triplicates), in DMSO or appropriate vehicle, for 30 min at 37° C. in a humidified (5% $CO_2$/95% air) incubator, prior to addition of 20 µl LPS (E. coli. 0111: B4; final concentration 10 µg/l). Each assay includes controls of diluted blood incubated with medium alone (6 wells/plate) or a known TNFα inhibitor as standard. The plates are then incubated for 6 hours at 37° C. (humidified incubator), centrifuged (2000 rpm for 10 min; 4° C.), plasma harvested (50-100 µl) and stored in 96 well plates at −70° C. before subsequent analysis for TNFα concentration by ELISA.

Test as an Agent to Inhibit In Vitro Cartilage Degradation

The ability of the compounds of this invention to inhibit the degradation of the aggrecan or collagen components of cartilage can be assessed essentially as described by K. M. Bottomley et al., (1997) Biochem J. 323:483-488.

Pharmacodynamic Test

To evaluate the clearance properties and bioavailability of the compounds of this invention an ex vivo pharmacodynamic test is employed which utilises the synthetic substrate assays above or alternatively HPLC or Mass spectrometric analysis. This is a generic test which can be used to estimate the clearance rate of compounds across a range of species. Animals (e.g. rats, marmosets) are dosed iv or po with a soluble formulation of compound (such as 20% w/v DMSO, 60% w/v PEG400) and at subsequent time points (e.g. 5, 15, 30, 60, 120, 240, 480, 720, 1220 mins) the blood samples are taken from an appropriate vessel into 10 U heparin. Plasma fractions are obtained following centrifugation and the plasma proteins precipitated with acetonitrile (80% w/v final concentration). After mins at −20° C. the plasma proteins are sedimented by centrifugation and the supernatant fraction is evaporated to dryness using a Savant speed vac. The sediment is reconstituted in assay buffer and subsequently analysed for compound content using the synthetic substrate assay. Briefly, a compound concentration-response curve is constructed for the compound undergoing evaluation. Serial dilutions of the reconstituted plasma extracts are assessed for activity and the amount of compound present in the original plasma sample is calculated using the concentration-response curve taking into account the total plasma dilution factor.

In Vivo Assessment

Test as an Anti-TNF Agent

The ability of the compounds of this invention as ex vivo TNFα inhibitors is assessed in the rat. Briefly, groups of male Wistar Alderley Park (AP) rats (180-210 g) are dosed with compound (6 rats) or drug vehicle (10 rats) by the appropriate route e.g. peroral (p.o.), intraperitoneal (i.p.), subcutaneous (s.c.). Ninety minutes later rats are sacrificed using a rising concentration of $CO_2$ and bled out via the posterior vena cavae into 5 Units of sodium heparin/ml blood. Blood samples are immediately placed on ice and centrifuged at 2000 rpm for 10 min at 4° C. and the harvested plasmas frozen at −20° C. for subsequent assay of their effect on TNFα production by LPS-stimulated human blood. The rat plasma samples are thawed and 175 μl of each sample are added to a set format pattern in a 96 U well plate. Fifty μl of heparinized human blood is then added to each well, mixed and the plate is incubated for 30 min at 37° C. (humidified incubator). LPS (25 μl; final concentration 10 μg/ml) is added to the wells and incubation continued for a farther 5.5 hours. Control wells are incubated with 25 μl of medium alone. Plates are then centrifuged for 10 min at 2000 rpm and 200 μl of the supernatants are transferred to a 96 well plate and frozen at −20° C. for subsequent analysis of TNF concentration by ELISA.

Data analysis by dedicated software calculates for each compound/dose:

Percent inhibition of $TNF\alpha$ =

$$\frac{\text{Mean } TNF\alpha \text{ (Controls)} - \text{Mean } TNF\alpha \text{ (Treated)} \times 100}{\text{Mean } TNF\alpha \text{ (Controls)}}$$

Test as an Anti-Arthritic Agent

Activity of a compound as an anti-arthritic is tested in the collagen-induced arthritis (CIA) as defined by D. E. Trentham et al., (1977) J. Exp. Med. 146:857. In this model acid soluble native type II collagen causes polyarthritis in rats when administered in Freunds incomplete adjuvant. Similar conditions can be used to induce arthritis in mice and primates.

Test as an Anti-Cancer Agent

Activity of a compound as an anti-cancer agent may be assessed essentially as described in I. J. Fidler (1978) Methods in Cancer Research 15:399-439, using for example the B16 cell line (described in B. Hibner et al., Abstract 283 p 75 10th NCI-EORTC Symposium, Amsterdam Jun. 16-19 1998).

Test as an Anti-Emphysema Agent

Activity of a compound as an anti-emphysema agent may be assessed essentially as described in Hautamaki et al (1997) Science, 277: 2002.

The invention will now be illustrated but not limited by the following Examples:

General analytical methods: $^1$H-NMR spectra were recorded on either a Varian[Unity]Inova 400 MHz or Varian Mercury-VX300 MHz instrument. The central solvent peak of chloroform-d ($\delta_H$ 7.27 ppm), dimethylsulfoxide-$d_6$ ($\delta_H$ 2.50 ppm) or methanol-$d_4$ ($\delta_H$ 3.31 ppm) were used as internal references. Low resolution mass spectra were obtained on a Agilent 1100 LC-MS system equipped with an APCI ionization chamber.

EXAMPLE 1

5-(2-{[4-(4'-fluoro[1,1'-biphenyl]-4-yl)-1-piperazinyl]sulfonyl}ethyl)-2,4-imidazolidinedione

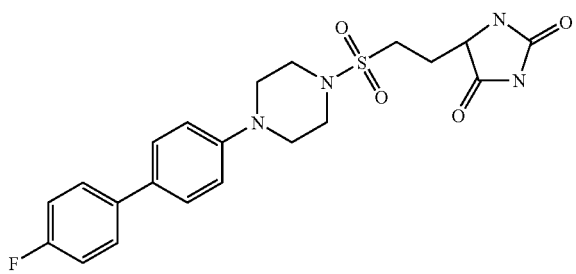

To the solution of 1-(4-fluorophenyl)-phenylpiperazin (0.125 mg, 0.48 mmol) in 5 ml of dichloromethane was added triethylamine (0.06 ml, 0.5 mmol) and 2-(2,5-dioxo-4-imidazolidinyl)-1-ethanesulfonyl chloride (0.113 ml 0.48 mol). The mixture was stirred for 18 hrs, diluted with DCM to 25 ml, extracted with 1N HCl (5 ml) sat. NaHCO3 (5 ml) and dried, evaporated, crystallised. EtOH-dioxan).

LC-MS (APCI) m/z 446.9 (MH+).

1H NMR δ 1.95 m (1H); 2.1 m (1.15H), 3.2 m (13.3H), 4.1 m (1H), 7.05 d (2H), 7.25 d (2.1H), 7.65 d (2.2H), 7.80 d (1.8H), 8.0 bs (NH).

The starting materials were prepared as follows:

2-(2,5-dioxo-4-imidazolidinyl)-1-ethanesulfonyl chloride

To the suspension of 5-(2-{[2-(2,5-dioxo-4-imidazolidinyl)ethyl]disulfanyl}ethyl)-2,4-imidazolidinedione (6.9 mol) in the mixture of 25 ml AcOH and 2 ml water stirred violently in three necked flask with gas-inlet tube, thermometer and short reflux condenser, placed in the ice bath, was bubbled chlorine gas for 15 min (until all precipitate dissolved) at max.temp.+5° C. Then, it was stirred 15 min more, evaporated to a small volume in vacuo (max.temp 30° C.), dissolved in 50 ml of dichloromethane, shaken carefully with sat.NaHCO3 (ca 25 ml), then with 10% sodium thiosulfate, dried, evaporated, crystallised from THF-hexane (Lora-Tamayo, M. et al, 1968, An. Quim., 64(6):591-606);

$^1$H NMR: δ 2.55 m (1.1H), 2.65 m (1.8H), 2.70 m (1H), 4.55 m (1H).

5-(2-{[2-(2,5-dioxo-4-imidazolidinyl)ethyl]disulfanyl}ethyl)-2,4-imidazolidinedione Commercially available RS homocystine (0.18 mol) was suspended in 25 ml water and of potassium cyanate 1.5 g (0.2 mol) was added and the mixture was stirred at 100° C. for 45 min. Then it was allowed to cool partially and 10 ml of 10% HCl were added at once and the mixture was stirred at 100° C. again for 50 min. It was placed in the fridge overnight, crystals were filtered and washed successively with water and dried in vacuo.

LC-MS (APCI) m/z 319.1 (MH+).

The overall generalised reaction scheme is shown below:

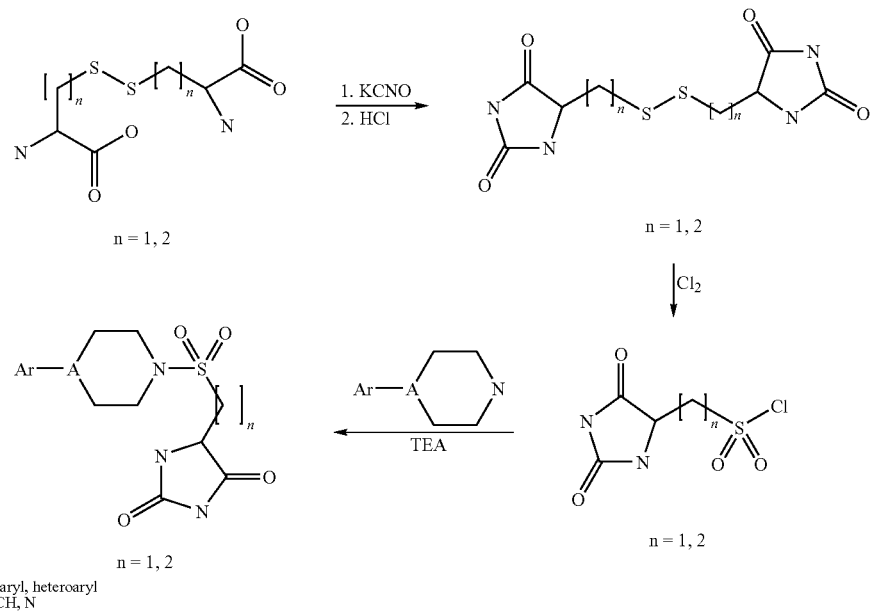

Ar = aryl, heteroaryl
A = CH, N

EXAMPLE 2

(5R)-5-{([4-phenyl-1-piperazinyl)sulfonyl]methyl}-2,4-imidazolidinedione

The title compound was prepared according to the scheme shown in Example 1. To the solution of R-(2,5-dioxo-4-imidazolidinyl)methanesulfonyl chloride (100 mg, 0.47 mmol) in 2.5 ml THF was added the solution of 1-phenylpiperazine (85 mg, 0.52 mmol) and 65 ul of triethylamine (0.52 mmol) in 2.5 ml THF via syringe at once. The mixture was stirred for 3 hrs, precipitated triethylammonium chloride was filtered, washed with two small portions of THF, evaporated and recrystallised from EtOH and a small amount of AcOH.

LC-MS (APCI) m/z 339.1 (MH+).

$^1$H NMR δ 2.5 m (2H), 3.1bs (6.5H), 3.3 m (2.5H), 4.55 m (1H), 6.8 t (1H), 6.9 d (1.88H), 7.2 t (2.05H), 9.1 bs (1.7H).

The starting materials were prepared as follows:

R-(2,5-dioxo-4-imidazolidinyl)methanesulfonyl chloride

To the suspension of R-5-({[(2,5-dioxo-4-imidazolidinyl)methyl]disulfanyl}methyl)-2,4-imidazolidinedione (6.9 mol) in the mixture of 25 ml AcOH and 2 ml water stirred violently in three necked flask with gas-inlet tube, thermometer and short reflux condenser, placed in the ice bath, was bubbled chlorine gas for 15 min (until all precipitate dissolved) at max.temp.+5° C. Then, it was stirred 15 min more, evaporated to a small volume in vacuo (max.temp 30° C.), dissolved in 50 ml of dichloromethane, shaken carefully with sat.NaHCO3 (ca 25 ml), then with 10% sodium thiosulfate, dried, evaporated, crystallised from THF-hexane (Lora-Tamayo, M. et al, 1968, An. Quim., 64(6):591-606);

$^1$H NMR (DMSO-d$_6$): δ 3.21 m (1.1H), 3.3 m (0.7H), 4.65 m (1H).

R-5-({[(2,5-dioxo-4-imidazolidinyl)methyl]disulfanyl}methyl)-2,4-imidazolidinedione Commercially available R cystine (0.18 mol) was suspended in 25 ml water and of potassium cyanate 1.5 g (0.2 mol) was added and the mixture was stirred at 100° C. for 45 min. Then it was allowed to cool partially and 10 ml of 10% HCl were added at once and the mixture was stirred at 10° C. again for 50 min. It was placed in the fridge overnight, crystals were filtered and washed successively with water and dried in vacuo.

LC-MS (APCI) m/z 291 (MH+).

EXAMPLE 3

(5S)-5-{[(4-phenyl-1-piperazinyl)sulfonyl]methyl}-2,4-imidazolidinedione

The title compound was prepared according to the scheme shown in Example 1. To the solution of S-(2,5-dioxo-4-imidazolidinyl)methanesulfonyl chloride (100 mg, 0.47 mmol) in 2.5 ml THF was added the solution of 1-phenylpiperazine (85 mg, 0.52 mmol) and 65 ul of triethylamine (0.52 mmol) in 2.5 ml THF via syringe at once. The mixture was stirred for 3 hrs, precipitated triethylammonium chloride was filtered, washed with two small portions of THF, evaporated and recrystallised from EtOH and a small amount of AcOH.

LC-MS (APCI) m/z 339.1 (MH+).

$^1$H NMR: δ 2.5 m (2H), 3.1 bs (6.5H), 3.3 m (2.5H), 4.55 m (1H), 6.8 t (1H), 6.9 d (1.88H), 7.2 t (2.05H), 9.1 bs (1.7H)

The starting materials were prepared as follows:

S-(2,5-dioxo-4-imidazolidinyl)methanesulfonyl chloride

To the suspension of S-5-({[(2,5-dioxo-4-imidazolidinyl)methyl]disulfanyl}methyl)-2,4-imidazolidinedione (6.9 mol) in the mixture of 25 ml AcOH and 2 ml water stirred violently in three necked flask with gas-inlet tube, thermometer and short reflux condenser, placed in the ice bath, was bubbled chlorine gas for 15 min (until all precipitate dissolved) at max.temp.+5° C. Then, it was stirred 15 min more, evaporated to a small volume in vacuo (max.temp 30° C.), dissolved in 50 ml of dichloromethane, shaken carefully with sat.NaHCO3 (ca 25 ml), then with 10% sodium thiosulfate, dried, evaporated, crystallised from THF-hexane (Lora-Tamayo, M. et al, 1968, An. Quim., 64(6):591-606);

$^1$H NMR (DMSO-d$_6$): δ 3.2 m (0.9H, 3.35 m (0.9H), 4.50 m (1H).

S-5-({[(2,5-dioxo-4-imidazolidinyl)methyl]disulfanyl}methyl)-2,4-imidazolidinedione Commercially available S cystine (0.18 mol) was suspended in 25 ml water and of potassium cyanate 1.5 g (0.2 mol) was added and the mixture was stirred at 100° C. for 45 min. Then it was allowed to cool partially and 10 ml of 10% HCl were added at once and the mixture was stirred at 100° C. again for 50 min. It was placed in the fridge overnight, crystals were filtered and washed successively with water and dried in vacuo.

LC-MS (APCI) m/z 291.1 (MH+).

EXAMPLE 4

(R)-5-(([4-(4'-fluoro[1,1'-biphenyl]-4-yl)-1-piperazinyl]sulfonyl)methyl)-2,4-imidazolidinedione

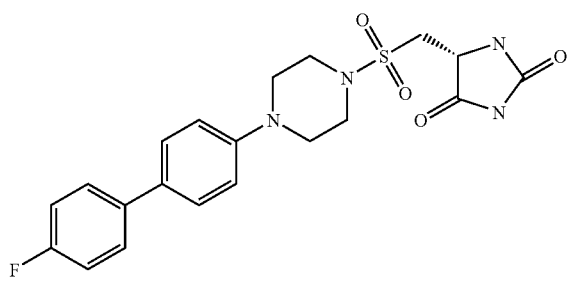

[(R)-2,5-Dioxoimidazolidinyl]methanesulfonyl chloride (0.0127 g, 0.060 mmol), 1-(4'-fluoro[1,1'-biphenyl]-4-yl) piperazine (0.0154 g, 0.060 mmol), triethylamine (0.0084 mL, 0.060 mmol) and dry tetrahydrofuran (0.70 mL) were stirred at room temperature over night. Polystyrene methylisocyanate (0.025 g, 0.030 mmol) was added and the mixture was shaken over night. The white suspension was carefully transferred to a round-bottomed flask, the resin was rinsed with tetrahydrofuran (2×1 mL) and washings were transferred to the bulk of suspension. The solvent was evaporated, the white solid was suspended in water (5 mL), collected on a filter, washed with water (2×1 mL), sucked free of water and dried in vacuo at 45° C. over night to afford approx. 0.010 g of the title compound.

LC-MS (APCI) m/z 434 (MH+).

$^1$H NMR (DMSO-d$_6$) δ 10.8 (1H, bs), 7.98 (1H, d, J=2 Hz), 7.63 (2H, dd, J$_1$=5 Hz, J$_2$=9 Hz), 7.53 (2H, d, J=9 Hz), 7.23 (2H, t, J=9 Hz), 7.05 (2H, d, J=9 Hz), 4.45 (1H, ddd, J$_1$=2 Hz, J$_2$=4 Hz, J$_3$=6 Hz), 3.51 (1H, dd, J$_1$=5 Hz, J$_2$=7 Hz), 3.44 (1H, dd, J$_1$=15 Hz, J$_2$=4 Hz), 3.35-3.25 (8H, m's; obscured by water signal) ppm.

$^{13}$C NMR (DMSO-d$_6$) δ 173.7, 161.3 (d, J=243 Hz), 157.3, 149.8, 136.4 (d, J=3 Hz), 130.1, 127.7 (d, J=8 Hz), 127.2, 116.2, 115.5 (d, J=21 Hz), 53.4, 49.4, 48.0, 44.9.

The starting materials were prepared as follows:

[(R)-2,5-Dioxoimidazolidinyl]methanesulfonyl chloride was prepared according to Mosher et al, 1958, J. Org. Chem. 23:1257.

1-(4'-Fluoro[1,1'-biphenyl]-4-yl)piperazine

4-Bromo-4'-fluorobiphenyl (4.46 g, 17.8 mmol), N-tert-butoxycarbonyl piperazine (3.97 g, 21.3 mmol), sodium tert-butoxide (2.39 g, 24.9 mmol), racemic 2,2'-bis(diphenylphosphino)-1,1'-binaphthyl (rac-BINAP) (0.082 g, 0.131 mmol), bis-(dibenzylideneacetone)palladium (0) (0.041 g, 0.045 mmol) and dry toluene (45 mL) were stirred at 80° C. under nitrogen atmosphere for six hours. The warm mixture was filtered, the solids were washed twice with warm toluene and the filtrate was concentrated in vacuo giving an orange-red crude, which was stirred with ether (50 mL) for two hours. The solid was filtered off, washed with small volumes of ether and dried in vacuo at 45° C. over night to give 5.57 g (88% yield) of tert-butyl 4-(4'-fluoro[1,1'-biphenyl]-4-yl)-1-piperazinecarboxylate. This product (5.52 g, 15.5 mmol) was dissolved in dioxane (150 mL) and stirred with 4M hydrochloric acid (8.1 mL) at RT over night. Concentrated hydrochloric acid (3.0 mL) was added and stirring was continued at 45° C. for 1.5 hours and at 60° C. for 1 hour. The solution was concentrated to dryness and the solid was triturated with ether (100 mL), filtered, washed with small volumes of ether and dried in vacuo at 45° C. for two hours to give 5.26 g (103% yield) of 1-(4'-fluoro[1,1'-biphenyl]-4-yl)piperazine dihydrochloride as a light-yellow salt.

LC-MS (APCI) m/z 257 (MH+).

$^1$H NMR (DMSO-d$_6$) δ 9.40 (2H, bs), 7.64 (2H, dd, J$_1$=6 Hz, J$_2$=9 Hz), 7.55 (2H, d, J=9 Hz), 7.24 (2H, t, J=9 Hz), 7.07 (2H, d, J=9 Hz), 3.46-3.41 (4H, m), 3.25-3.17 (4H, m).

The salt was treated with aqueous sodium hydroxide solution and the base was taken up in dichloro-methane. Drying with Na$_2$SO$_4$, filtering and concentrating the organic phase gave the title compound as an off white solid.

$^1$H NMR (DMSO-d$_6$) δ 7.61 (2H, dd, J=6 Hz, J$_2$=9 Hz), 7.49 (2H, d, J=9 Hz), 7.22 (2H, t, J=9 Hz), 6.98 (2H, d, J=9 Hz), 3.10-3.06 (4H, m), 2.86-2.81 (4H, m).

EXAMPLE 5

Using an analogous procedure to that described in Example 4, [(4R)-2,5-dioxoimidazolidinyl]methanesulfonyl chloride was reacted with the appropriate primary or secondary amine to give the compounds listed below. All the amines employed are commercially available.

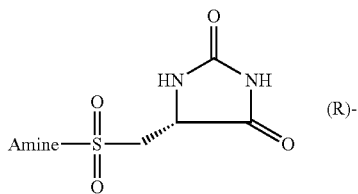

The Table below gives the Amine group for each compound of the above structure.

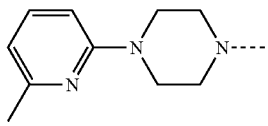

MW. 353.40
m/z 354 (MH+)

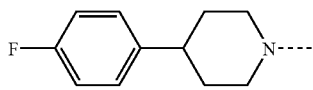

MW. 355.39
m/z 356 (MH+)

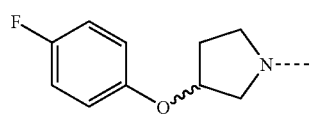

MW. 357.36
m/z 358 (MH+)

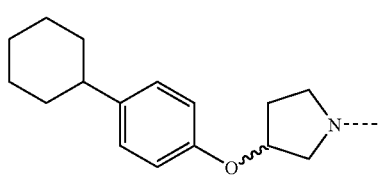

MW. 421.52
m/z 422 (MH+)

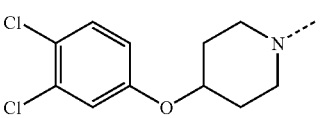

MW. 422.29
m/z 423 (MH+)

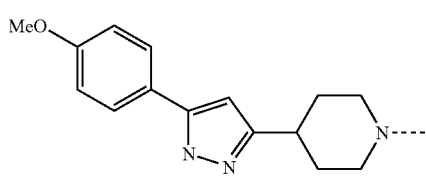

MW. 433.49
m/z 434 (MH+)

-continued

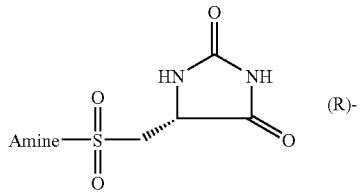

The Table below gives the Amine group for each compound of the above structure.

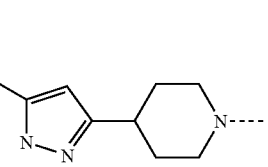

MW. 437.91
m/z 438 (MH+)

EXAMPLE 6

(S)-5-(([4-(4'-fluoro[1,1'-biphenyl]-4-yl)-1-piperazinyl]sulfonyl)methyl)-2,4-imidazolidinedione

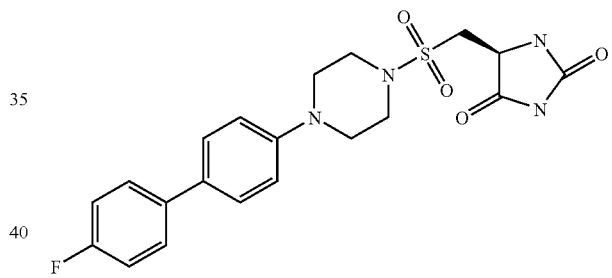

[(S)-2,5-Dioxoimidazolidinyl]methanesulfonyl chloride (0.0127 g, 0.060 mmol), 1-(4'-fluoro[1,1'-biphenyl]-4-yl)piperazine (0.0154 g, 0.060 mmol), triethylamine (0.0084 mL, 0.060 mmol) and dry tetrahydrofuran (0.70 mL) were stirred at room temperature over night. Polystyrene methylisocyanate (0.025 g, 0.030 mmol) was added and the mixture was shaken over night. The white suspension was carefully transferred to a round-bottomed flask, the resin was rinsed with tetrahydrofuran (2×1 mL) and washings were transferred to the bulk of suspension. The solvent was evaporated, the white solid was suspended in water (5 mL), collected on a filter, washed with water (2×1 mL), sucked free of water and dried in vacuo at 45° C. over night to afford approx. 0.010 g of the title compound.

LC-MS (APCI) m/z 433 (MH+).

$^1$H NMR (DMSO-d$_6$) δ 10.8 (1H, br s), 7.98 (1H, d, J=2 Hz), 7.63 (2H, dd, J$_1$=5 Hz, J$_2$=9 Hz), 7.53 (2H, d, J=9 Hz), 7.23 (2H, t, J=9 Hz), 7.05 (2H, d, J<Hz), 4.45 (1H, ddd, J$_1$=2 Hz, J$_2$=4 Hz, J$_3$=6 Hz), 3.51 (1H, dd, J=15 Hz, J$_2$=7 Hz), 3.44 (1H, dd, J$_1$=15 Hz, J$_2$=4 Hz), 3.35-3.25 (8H, m's; obscured by water signal).

$^{13}$C NMR (DMSO-d$_6$) δ 173.7, 161.3 (d, J=243 Hz), 157.3, 149.8, 136.4 (d, J=3 Hz), 130.1, 127.7 (d, J=8 Hz), 127.2, 116.2, 115.5 (d, J=21 Hz), 53.4, 49.4, 48.0, 44.9.

The starting materials were prepared as follows:

[(S)-2,5-Dioxoimidazolidinyl]methanesulfonyl chloride was prepared according to Mosher et al, 1958, J. Org. Chem. 23:1257.

1-(4'-Fluoro[1,1'-biphenyl]-4-yl)piperazine was prepared according to Example 4.

EXAMPLE 7

Using an analogous procedure to that described in Example 6, [(4S)-2,5-dioxoimidazolidinyl]methanesulfonyl chloride was reacted with the appropriate primary or secondary amine to give the compounds listed below. All the amines employed are commercially available.

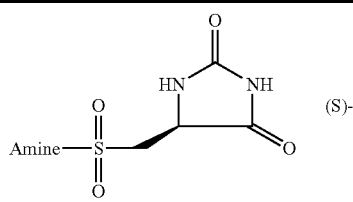

The Table below gives the Amine group for each compound of the above structure.

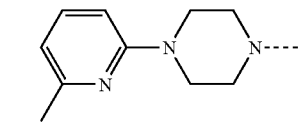

MW. 353.40
m/z 354 (MH+)

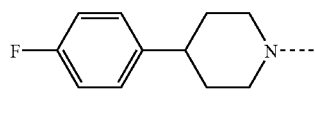

MW. 355.39
m/z 356 (MH+)

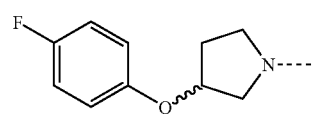

MW. 357.36
m/z 358 (MH+)

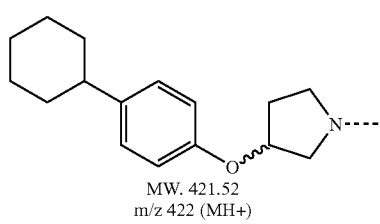

MW. 421.52
m/z 422 (MH+)

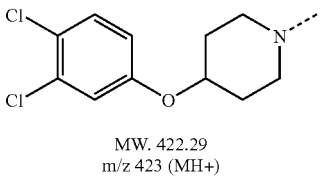

MW. 422.29
m/z 423 (MH+)

-continued

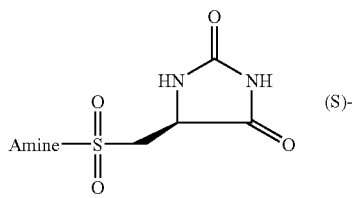

The Table below gives the Amine group for each compound of the above structure.

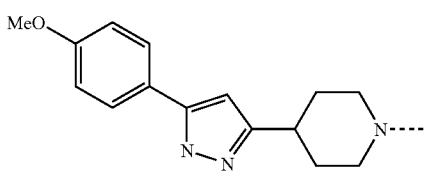

MW. 433.49
m/z 434 (MH+)

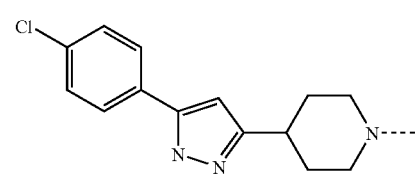

MW. 437.91
m/z 438 (MH+)

EXAMPLE 8

Hydantoins with the following general structure were synthesised (where E is carbon or a heteroatom):

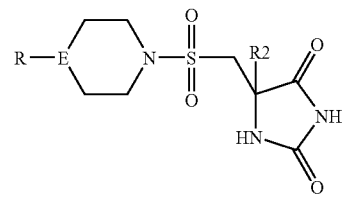

Representative Synthetic Route:

(5R,S)-5-[4-(4-Fluoro-phenyl)-piperidine-1-sulfonyl-methyl]-5-methyl-imidazolidine-2,4-dione

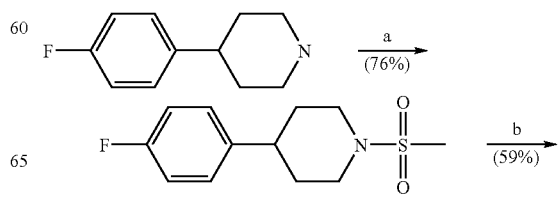

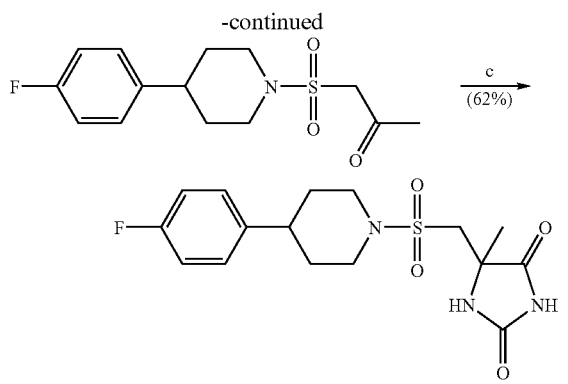

Reagents: a) MeSO$_2$Cl, DCM, 0° C., 2.5 h. b) i. LHMDS, THF, 45 min. ii. MeOAc, THF, 40 min. c) KCN, (NH$_4$)$_2$CO$_3$, 50% EtOH/H$_2$O, 70° C., 17 h.

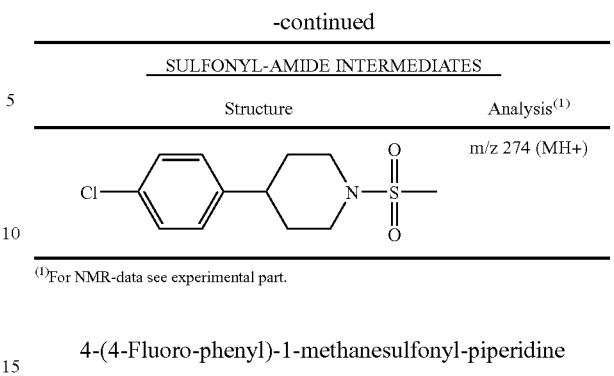

[(1)] For NMR-data see experimental part.

4-(4-Fluoro-phenyl)-1-methanesulfonyl-piperidine 4-(4-Fluoro-phenyl)piperidine hydrochloride (2.16 g; 10 mmol) and diisopropylethylamine (4.35 ml; 25 mmol) was dissolved in DCM (60 ml) and cooled under nitrogen on a ice/water bath. Methanesulfonyl chloride (1.56 ml; 10.1 mmol) was dissolved in DCM (5 ml) and added dropwise during 2 min. The reaction mixture was stirred for 2.5 h on the ice/water bath. The reaction mixture was washed with dilute HCl (aq), pH=2, H$_2$O, and 1M Na$_2$CO$_3$. The organic phase was dried (Na$_2$SO$_4$), filtered and evaporated to give a crude product that was recrystallised from THF/n-Heptane. The colourless crystals was removed by filtration and dried under vacuum at 45° C.

Obtained 1.96 g (76% yield) of the title compound.

LC-MS (APCI) M/Z 258 (MH+).

$^1$H NMR (DMSO-d$_6$): δ 7.31 (m, 2H), 7.12 (m, 2H), 3.67 (m, 2H), 2.80 (dt, 2H), 2.64 (m, 1H), 1.85 (m, 2H), 1.65 (m, 2H).

5-Chloro-2-(1-methanesulfonyl-piperidine-4-yloxy)-pyridine

The title compound was prepared as described in the synthesis of 4-(4-Fluoro-phenyl)-1-methanesulfonyl-piperidine.

5-Chloro-2-(piperidine-4-yloxy)-pyridine (2.13 g; 10 mmol) (preparation of this compound was made as described in WO 99-GB2801), diisopropylethylamine (2.20 ml; 12.5 mmol) and Methanesulfonyl chloride (1.56 ml; 10.1 mmol) gave 2.14 g (74%) of the title compound.

LC-MS (APCI) m/z 291 (MH+).

$^1$H NMR (DMSO-d$_6$): δ 8.20 (d, 1H), 7.81 (dd, 1H), 6.87 (d, 1H), 5.09 (m, 1H), 3.41-3.30 (m, 2H), 3.15-3.06 (m, 2H), 2.90 (s, 3H), 2.04 (m, 2H), 1.75 (m, 2H).

1-methylsulfonyl)-4-[5-trifluoromethyl)pyridin-2-yl] piperazine

1-[5-(Trifluoromethyl)-Pyridin-2-yl]-piperazine (1.0 g; 4.3 mmol) and Diisopropylethylamine (0.9 ml; 5.4 mmol) was dissolved in DCM (10 ml). Molecular sieves (4 A) was added and the solution was cooled on a ice/water bath. Methanesulfonylchloride (0.9 ml; 12 mmol) was added and a slurry formed that was stirred for 15 min, the reaction mixture was allowed to reach room temperature and after 1 h. the reaction was quenched by adding 5% KHCO$_3$. Evaporation of solvents and the residue was dissolved between DCM and 5% KHCO$_3$. Separation and extraction of the waterphase with DCM (1×). The combined organic phases was dried (MgSO$_4$), filtered and evaporated to give a crude product as a slightly yellow solid.

Recrystallised (3x) from EtOAc/Heptan gave the title compound as colourless crystals.

Obtained 1.06 g (79% yield) of the title compound.
Purity>95% (HPLC, 254 nm)
LC-MS (APCI) m/z 310 (MH+).
$^1$H-NMR (DMSO-$d_6$): δ 8.44 (1H, bs), 7.85 (1H, dd), 7.02 (1H, d), 3.77 (4H, bt), 3.20 (4H, bt), 2.90 (3H, s).

The following compounds were prepared as described in the synthesis of 1-(methylulfonyl)-4-[5-(trifluoromethyl)pyridin-2-yl]piperazine

6-[4-(methylsulfonyl)piperazine-1-yl]pyridine-3-carbonitrile 6-(1-piperazino)-pyridine-3-carbonitrile (2.07 g; 11 mmol), Diisopropylethylamine (2.4 ml; 13.8 mmol) and Methanesulfonylchloride (0.86 ml; 11 mmol) in DCM (20 ml) gave 2.53 g (86%) of the title compound.
Purity>95% (NMR).
LC-MS (APCI) m/z 267 (MH+).
$^1$H-NMR (DMSO-$d_6$): δ 8.52 (1H, dd), 7.90 (1H, dd), 7.00 (1H, d), 3.79 (4H, brt), 3.19 (4H, bt), 2.90 (3H, s).

1-(4-fluorophenyl)-4-(methylsulfonyl)piperazine 1-(4-Fluorophenyl)-piperazine (1.98 g; 1 mmol), Diisopropylethylamine (2.4 ml; 13.8 mmol) and Methanesulfonylchloride (0.86 ml; 11 mmol) in DCM (20 ml) gave 2.46 g (86%) of the title compound.
Purity>95% (NMR).
LC-MS (APCI) m/z 259 (MH+).
$^1$H-NMR (DMSO-$d_6$): δ 7.11-6.96 (4H, m), 3.28-3.20 (4H, m), 3.20-3.14 (4H, m), 2.92 (3H, s).

1-[(4-fluorophenyl)methyl]-4-methylsulfonyl)piperazine 1-(4-Fluor-benzyl)-piperazine (2.14 g; 11 mmol), Diisopropylethylamine (2.4 ml; 13.8 mmol) and Methanesulfonylchloride (0.86 ml; 11 mmol) in DCM (20 ml) gave 1.97 g (65%) of the title compound.
Purity>95% (NMR)
LC-MS (APCI) m/z 273 (MH+).
$^1$H-NMR (DMSO-d): δ 7.40-7.28 (2H, m), 7.21-7.10 (2H, m), 3.50 (2H, bs), 3.10 (4H, m), 2.87 (3H, bs), 2.44 (4H, m).

2-[4-(methylsulfonyl)piperazin-1-yl]pyrimidine 1-(2-Pyrimidyl)-piperazine dihydrochloride (2.61 g; 11 mmol) and Diisopropylethylamine (7.2 ml; 41.3 mmol) was stirred in DCM (20 ml) for 30 min. The precipitated salts was removed by filtration and solvents evaporated, residue was redissolved in DCM (20 ml). Diisopropylethylamine (2.4 ml; 1 mmol) and 4 Å mol. sieves was added, the yellow solution was cooled on ice/water bath and Methanesulfonylchloride (0.86 ml; 11 mmol) was added. The resulting red solution was stirred for 15 min, the reaction mixture was allowed to reach room temperature and after 1 h. the reaction was quenched by adding 5% KHCO$_3$. Evaporation of solvents and the residue was dissolved between DCM and 5% KHCO$_3$. Separation difficult due to foam formation. Waterphase was saturated with NaCl and pH adjusted to 10-11. Extraction with EtOAc (3x). The combined organic phases was dried (K$_2$CO$_3$), filtered and evaporated to give a crude product as a red solid.

Recrystallised (3x) from EtOAc/Heptan gave the title compound as a red powder.
Obtained 0.6 g (22%) of the title compound.
Purity>95% (NMR).
LC-MS (APCI) m/z 243 (MH+).
$^1$H-NMR (DMSO-$d_6$): δ 8.39 (2H, d), 6.68 (1H, t), 3.85 (4H, bt), 3.17 (4H, bt), 2.88 (3H, s).

4-(4-chlorophenyl)-1-(methylsulfonyl)piperidine

The title compound was prepared as described in the synthesis of 4-(4-Fluoro-phenyl)-1-methanesulfonyl-piperidine.
4-(4-Chlorophenyl)piperidine hydrochloride (0.9 g, 3.9 mmol), diisopropylethylamine (1.7 ml, 9.7 mmol) and methanesulfonylchloride (0.33 ml, 4.3 mmol) in DCM (30 ml) and gave 0.82 g (78%) of the title compound after recrystallisation from EtOAc/Heptane.
Purity>95%.
LC-MS (APCI) m/z 274 (MH+),
$^1$H NMR CDCl$_3$: δ 1.83 (2H, dd); 1.92-2.01 (2H, m); 2.55-2.68 (1H, m); 2.79 (2H, dt); 2.85 (3H, s); 3.97 (2H, d); 7.16 (2H, d); 7.32 (2H, d).

| ESTER INTERMEDIATES | |
|---|---|
| Structure | Analysis |
| (pyrimidine-CH$_2$CH$_2$CH$_2$-COOEt) | m/z 195 (MH+) $^1$H-NMR |
| (pyrimidine-CH$_2$CH$_2$-COOEt) | m/z 181 (MH+) |
| (Boc-piperidine-CH$_2$-COOMe) | m/z 158 (MH+ − boc) |

All other esters used are commercially available or earlier described.

4-Pyrimidin-2-yl-butyric acid ethyl ester

2-Bromopyrimidine (1.0 g, 6.3 mmol) was slurried in dry THF (8 mL). N$_2$ (g) was bubbled through the slurry for 5 min. Pd(CH$_3$CN)$_2$Cl$_2$ (8 mg, 0.03 mmol) and PPh$_3$ (23.6 mg, 0.09 mmol) was added. Under N$_2$-atmosphere 4-Ethoxy-4-oxo-butylzincbromide (0.5M/THF) (15 mL, 7.5 mL) was added in one portion. The resulting brown solution was stirred at room temperature for 2 h. H$_2$O (5 mL) was added and the mixture stirred for 60 min. before evaporation of solvents. The residue was redissolved in DCM (150 mL) and washed with 0.5M trisodiumcitrate (100 mL), H$_2$O (100 mL) and brine (100 mL), dried (MgSO$_4$), filtered and evaporated to give 1.3 g of an orange oil. The crude product was purified on 70 g of Si-60 gel using a gradient of 100% Heptane to 100% EtOAc as eluent. The fractions containing the product was collected and solvent evaporated to give a yellow oil. Purity by NMR>95% was considered enough for our need. Obtained 1.12 g (92% yield) of the title compound.

LC-MS (APCI) m/z 195 (MH+).

$^1$H-NMR (CDCl$_3$): δ 8.67 (d, 2H), 7.14 (t, 1H), 4.12 (q, 2H), 3.02 (t, 2H), 2.41 (t, 2H), 2.18 (q, 2H), 1.25 (t, 3H).

3-Pyrimidin-2-yl-propionic acid ethyl ester

2-Bromopyrimidine (1.0 g, 6.3 mmol) was dissolved in THF (8 mL) and bubbled through with nitrogen. Pd(MeCN)$_2$Cl$_2$ (8 mg, 0.03 mmol) and PPh$_3$ (23.6 mg, 0.09 mmol) was added followed by addition of 3-ethoxy-3-oxopropylzinkbromid (15 mL, 7.5 mmol). The reaction was stirred at rt for several days. The crude product was purified on silica with Heptane-EtOAc 3:1 as eluent giving 0.60 g (52%) of the title compound.

LC-MS (APCI) m/z 181 (MH+).

tert-butyl 4-(2-methoxy-2-oxoethyl)piperidine-1-carboxylate tert-Butyl 4-(2-methoxy-2-oxoethylidene)piperidine-1-carboxylate (3.6 g, 14 mmol) and 10% Pd/C moistened with water (0.8 g) was mixed in MeOH (75 mL) and stirred under H$_2$ (1 atm) for 4 h. The mixture was filtered through Celite and concentrated to give the title compound (3.6 g, 99%).

LC-MS (APCI) m/z 158 (MH+-boc).

$^1$H NMR (CDCl$_3$): δ 4.07 (2H, bs); 3.68 (3H, s); 2.72 (2H, t); 2.25 (2H, d, J=7.1 Hz); 2.01-1.86 (1H, m); 1.68 (2H, d); 1.46 (9H, s); 1.23-1.08 (2H, m).

KETONE INTERMEDIATES

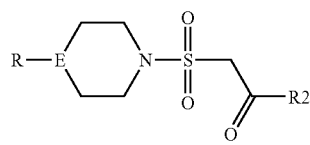

| R | E | R2 | Analysis |
|---|---|---|---|
| 4-F-phenyl | CH | Me | m/z 300 (MH+) |
| 4-F-phenyl | CH | propylphenyl | H-NMR. see exp. part. |
| 4-F-phenyl | CH | butyl-imidazole | m/z 394 (MH+) |
| 4-F-phenyl | CH | butyl-pyrimidine | m/z 406 (MH+)[1] |
| 5-Cl-2-methoxy-pyridin-yl | CH | Me | m/z 333 (MH+)[1] |
| 5-Cl-2-methoxy-pyridin-yl | CH | propylphenyl | m/z 423 (MH+)[1] |
| 5-Cl-2-methoxy-pyridin-yl | CH | butyl-imidazole | m/z 427 (MH+)[1] |
| 5-Cl-2-methoxy-pyridin-yl | CH | butyl-pyrimidine | m/z 439 (MH+)[1] |
| 5-Cl-2-methoxy-pyridin-yl | CH | propyl | m/z 347 (MH+)[1] |

-continued
KETONE INTERMEDIATES
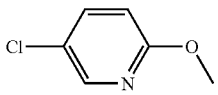
| R | E | R2 | Analysis |
|---|---|---|---|
|  | CH | 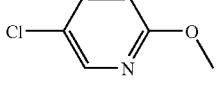 | m/z 361 (MH+)(1) |
|  | CH | 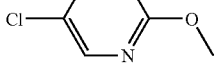 | m/z 375 (MH+)(1) |
| 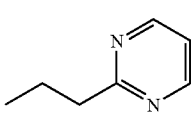 | CH | 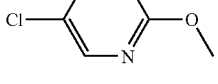 | m/z 425 (MH+)(1) |
| 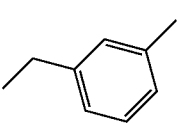 | CH | 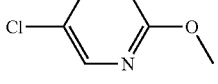 | m/z 423 (MH+)(1) |
| 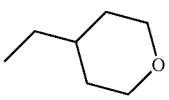 | CH | 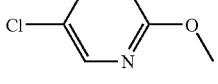 | m/z 417 (MH+)(1) |
| 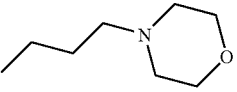 | CH | 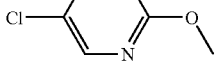 | m/z 446 (MH+)(1) |
| 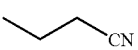 | CH | 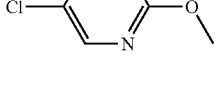 | m/z 372 (MH+)(1) |
| 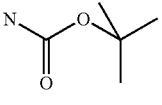 | CH | 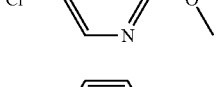 | m/z 476 (MH+)(1) |
| 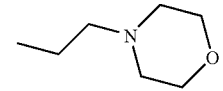 | CH | 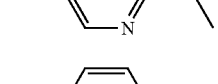 | m/z 432 (MH+)(1) |
| 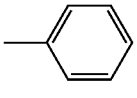 | CH | 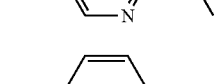 | m/z 395 (MH+)(1) |
|  | CH |  | m/z 413 (MH+)(1) |
| 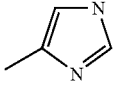 | CH |  | m/z 385 (MH+)(1) |

-continued
KETONE INTERMEDIATES
| R | E | R2 | Analysis |
|---|---|----|----------|
| 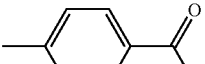 | CH |  | — |
| 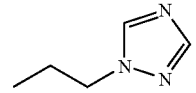 | CH | 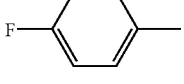 | m/z 414 (MH+)[(1)] |
| 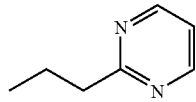 | CH | 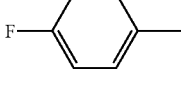 | m/z 392 (MH+)[(1)] |
| 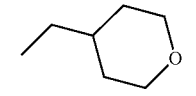 | CH | 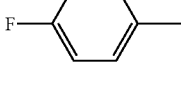 | m/z 384 (MH+)[(1)] |
| 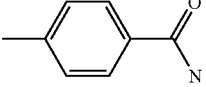 | CH | 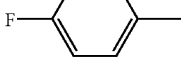 | m/z 405 (MH+)[(1)] |
| 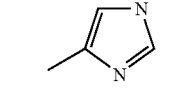 | CH | 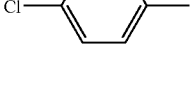 | m/z 352 (MH+)[(1)] |
|  | CH | 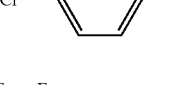 | m/z 400 (MH+)[(1)] |
| 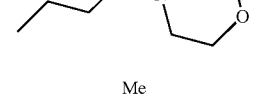 | CH | 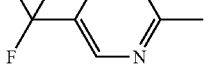 | m/z 429 (MH+)[(1)] |
| 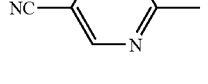 | N | Me | m/z 352 (MH+)[(1)] |
| 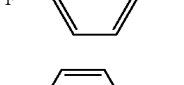 | N | Me | m/z 309 (MH+)[(1)] |
| 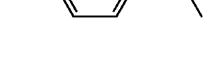 | N | Me | m/z 301 (MH+)[(1)] |
|  | N | Me | m/z 315 (MH+)[(1)] |

KETONE INTERMEDIATES

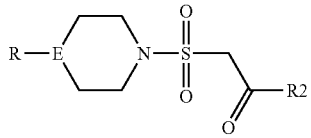

| R | E | R2 | Analysis |
|---|---|---|---|
| 2-pyrimidinyl | N | Me | m/z 285 (MH+)[1] |
| 5-chloro-2-methoxy-pyridinyl (via CH-O-C(=O)-O-tBu linker to 4-ethyl-piperidine) | | | m/z 517 (MH+)[1] |

[1]crude products, no NMR available, mtrl. used directly in next synthetic step.

1-[4-4(Fluoro-phenyl)-piperidine-1-sulfonyl]-propan-2-one 4-(4-Fluoro-phenyl)-1-methanesulfonyl-piperidine (100 mg; 0.39 mmol) was dissolved in dry THF (3 mL) under a protective nitrogen atmosphere. Lithium bis(trimethylsilyl)amide as a 1.0 M solution in THF (1.0 mL; 11.0 mmol) was added in one portion at room temperature, the resulting yellow solution was stirred for 45 min. Methylacetate (50 mg; 0.68 mmol) dissolved in dry THF (0.5 mL) was added, the mixture was stirred at room temperature for 40 min. The reaction was quenched by adding NH$_4$Cl (sat.) (2 mL). The 4 mixture was evaporated and the resulting solid was dissolved in a mixture of DCM and H$_2$O. The organic phase was separated and washed with brine, dried (MgSO$_4$), filtrated and evaporated. The crude product was purified on 20 g of Si-60 gel using a gradient of 100% Heptane to 50% EtOAc, a flow of 20 mL/min was used and UV=254 nm was used for detection. The fractions containing the product was evaporated and this gave the title compound as a colourless solid.

Obtained 70 mg (59% yield).

TLC(Si-60; EtOAc:Heptane (2:1)): R$_f$=0.65

LC-MS (APCI) m/z 300.1 (MH+).

$^1$H-NMR (CDCl$_3$): δ 7.17 (m, 2H), 7.01 (m, 2H), 4.02 (s, 2H), 3.93 (m, 2H), 2.94 (dt, 2H), 2.63 (m, 1H), 2.46 (s, 3H), 1.91 (m, 2H), 1.77 (m, 2H).

The following compounds were prepared as described in the synthesis of 1-[4-4(Fluoro-phenyl)-piperidine-1-sulfonyl]-propan-2-one.

1-[4-4(Fluoro-phenyl)-piperidine-1-sulfonyl]-4 phenyl-butan-2-one 4-(4-Fluoro-phenyl)-1-methanesulfonyl-piperidine (100 mg; 0.39 mmol), Methyl-3-phenylpropionate (112 mg; 0.68 mmol) and Lithium bis(trimethylsilyl)amide 1.0 MT (1.0 mL; 1.0 mmol) gave 93 mg (61%) of the title compound.

TLC(Si-60; EtOAc:Heptane (2:1)): R$_f$=0.68

$^1$H-NMR (CDCl$_3$): δ 7.30-7.10 (m, 7H), 6.99 (m, 2H), 3.97 (s, 2H), 3.79 (m, 2H), 3.11 (t, 2H), 2.94 (t, 2H), 2.83 (dt, 2H) 2.57 (m, 1H), 1.83 (m, 2H), 1.70 (m, 2H).

1-[4-4(Fluoro-phenyl)-piperidine-1-sulfonyl]-5-imidazol-pentan-2-one 4-(4-Fluoro-phenyl)-1-methanesulfonyl-piperidine (100 mg; 0.3-9 mmol), 4-imidazol-1-yl-butyric acid ethyl ester (127 mg; 0.70 mmol) and Lithium bis(trimethylsilyl)amide 1.0M/THF (1.0 mL; 1.0 mmol) gave 75 mg (48%) of the title compound.

LC-MS (APCI) m/z 394 (MH+).

$^1$H-NMR (CDCl$_3$): δ 7.48 (s, 1H), 7.16 (m, 2H), 7.08 (s, 1H), 7.02 (m, 2H), 6.93 (s, 2H), 4.00 (t, 2H), 3.97 (s, 2H), 3.90 (m, 2H), 2.92 (dt, 2H), 2.77 (t, 2H), 2.63 (m, 1H), 2.12 (q, 2H), 1.92 (m, 2H), 1.77 (m, 2H).

1-[4(4-Fluoro-phenyl)-piperidine-1-sulfonyl]-5-pyrimidin-2-yl-pentan-2-one 4-(4-Fluoro-phenyl)-1-methanesulfonyl-piperidine (150 mg; 0.39 mmol) was dissolved in dry THF (3 mL) and cooled on an ice/brine mixture. Lithium bis(trimethylsilyl)amide as a 1.0 M solution in THF (1.5 mL; 1.5 mmol) was added and the mixture was stirred for 40 min. 4-Pyrimidin-2-yl-butyric acid ethyl ester (169 mg; 0.87 mmol) in THF (0.5 mL) was added, the reaction was stirred for 30 min and then allowed to reach room temperature. After 2 h. LC/MS analysis of the reaction mixture showed >98% conversion of the starting material and the reaction was quenched by adding saturated NH$_4$Cl (aq) (2 mL). The mixture was evaporated and the resulting solid was dissolved in a mixture of DCM and 5% KHCO$_3$. The organic phase was separated and the water phase was extracted once with DCM. The combined organic phases was washed with brine, dried (MgSO$_4$), filtered, and evaporated to give a yellow oil. The oil was dissolved in EtOAc and isoHexane was added until a solid formed. Evaporation of solvent gave a yellow solid crude product. This material was analysed using LC/MS only and used without further purification in the next step.

Obtained 234 mg of the crude title compound.

LC-MS (APCI) m/z 406.1 (MH+).

The following compounds were prepared as described in the synthesis of 1-[4-(4-Fluoro-phenyl)-piperidine-1-sulfonyl]-5-pyrimidin-2-yl-pentan-2-one. They were obtained as crude products and used without further purification.

1-[4-(5-Chloro-pyridin-2-yloxy)-piperidine-1-sulfonyl]-propan-2-one

Starting from 5-Chloro-2-(1-methanesulfonyl-piperidine-4-yloxy)-pyridine (150 mg; 0.51 mmol), Methylacetate (61 mg; 0.82 mmol) and Lithium bis(trimethylsilyl)amide 1.0M/THF (1.3 ml; 1.3 mmol).

Obtained 161 mg of the crude title compound. Used without further purification.

LC-MS (APCI) m/z 333.1 (MH+).

1-[4-(5-Chloro-pyridin-2-yloxy)-piperidine-1-sulfonyl]-4-phenyl-butan-2-one

Starting from 5-Chloro-2-(1-methanesulfonyl-piperidine-4-yloxy)-pyridine (150 mg; 0.51 mmol), Methyl-3-phenyl-propionate (126 mg; 0.77 mmol) and Lithium bis(trimethylsilyl)amide 1.0 M/THF (1.3 ml; 1.3 mmol).

Obtained 258 mg of the crude title compound. Used without further purification.

LC-MS (APCI) m/z 423.2 (MH+).

1-[4-(5-Chloro-pyridin-2-yloxy)-piperidine-1-sulfonyl]-5-imidazol-1-yl-pentan-2-one Starting from 5-Chloro-2-(1-methanesulfonyl-piperidine-4-yloxy)-pyridine (150 mg; 0.51 mmol), 4-imidazol-1yl-butyric acid ethyl ester (140 mg; 0.77 mmol) and Lithium bis(trimethylsilyl)amide 1.0 M/THF (1.3 ml; 1.3 mmol).

Obtained 268 mg of the crude title compound. Used without further purification.

LC-MS (APCI) m/z 427.2 (MH+).

1-[4-(5-Chloro-pyridin-2-yloxy)-piperidine-1-sulfonyl]-5-pyrimidin-2-yl-pentan-2-one Starting from 5-Chloro-2-(1-methanesulfonyl-piperidine-4-yloxy)-pyridine (150 mg; to 0.51 mmol), 4-Pyrimidin-2-yl-butyric acid ethyl ester (147 mg; 0.76 mmol) and Lithium bis(trimethylsilyl)amide 1.0 M/THF (1.3 ml; 1.3 mmol).

Obtained 244 mg of the crude title compound. Used without further purification.

LC-MS (APCI) m/z 439.2 (MH+).

1-[4-(5-Chloro-pyridin-2-yloxy)piperidine-1-sulfonyl]-butan-2-one

LC-MS (APCI) m/z 347 (MH+)

1-[4-(5-Chloro-pyridin-2-yloxy)-piperidine-1-sulfonyl]-pentan-2-one

LC-MS (APCI) m/z 361 (MH+)

1-[4-(5-Chloro-pyridin-2-yloxy)-piperidine-1-sulfonyl]-4-methyl-pentan-2-one LC-MS (APCI) m/z 375 (MH+)

1-[4-(5-Chloro-pyridin-2-yloxy)piperidine-1-sulfonyl]-4-pyrimidin-2-yl-butan-2-one LC-MS (APCI) m/z 425 (MH+)

1-({4-[(5-Chloropyridin-2-yl)oxy]piperidin-1-yl}sulfonyl)-3-(3-methylphenyl)propan-2-one LC-MS (APCI) m/z 423 (MH+)

1-({4-[(5-Chloropyridin-2-yl)oxy]piperidin-1-yl}sulfonyl)-3-tetrahydro-2H-pyran-4-ylpropan-2-one LC-MS (APCI) m/z 417 (MH+)

1-({4-[(5-chloropyridin-2-yl)oxy]piperidin-1-yl}sulfonyl)-5-morpholin-4-ylpentan-2-one LC-MS (APCI) m/z 446 (MH+)

5-({4-[(5-chloropyridin-2-yl)oxy]piperidin-1-yl}sulfonyl-4-oxopentanenitrile LC-MS (APCI) m/z 372 (MH+)

1,1-dimethylethyl 5-({4-[(5-chloropyridin-2-yl)oxy]piperidin-1-yl}sulfonyl)-4-oxopentylcarbamate LC-MS (APCI) m/z 476 (MH+)

1-({4-[(5-chloropyridin-2-yl)oxy]piperidin-1-yl}sulfonyl)-4-morpholin-4-ylbutan-2-one LC-MS (APCI) m/z 432 (MH+)

2-{4-[(5-chloropyridin-2-yl)oxy]piperidin-1-yl}sulfonyl)-1-phenylethanone

LC-MS (APCI) m/z 395 (MH+)

2-({4-[(5-chloropyridin-2-yl)oxy]piperidin-1-yl}sulfonyl)-1-(4-fluorophenyl)ethanone LC-MS (APCI) m/z 413 (MH+)

2-({4-[(5-chloropyridin-2-yl)oxy]piperidin-1-yl}sulfonyl)-1-(1H-imidazol-4-yl)ethanone LC-MS (APCI) m/z 385 (MH+)

4-[({4-[(5-chloropyridin-2-yl)oxy]piperidin-1-yl}sulfonyl)acetyl]benzamide n.d.

1-({4-[(5-chloropyridin-2-yl)oxy]piperidin-1-yl}sulfonyl H-1,2,4-triazol-1-yl)butan-2-one LC-MS (APCI) m/z 414 (MH+)

1-{[4-(4-fluorophenyl)piperidin-1-yl]sulfonyl}-4-pyrimidin-2-ylbutan-2-one

LC-MS (APCI) m/z 392 (MH+)

1-({[4-(4-fluorophenyl)piperidin-1-yl]sulfonyl}-3-tetrahydro-2H-pyran ylpropan-2-one LC-MS (APCI) m/z 384 (MH+)

4-({[4-(4-fluorophenyl)piperidin-1-yl]sulfonyl}acetyl)benzamide

LC-MS (APCI) m/z 405 (MH+)

2-{[4-(4-fluorophenyl)piperidin-1-yl]sulfonyl}-1-(1H-imidazol-4-yl)ethanone

LC-MS (APCI) m/z 352 (MH+)

1-{[4-(4-chlorophenyl)piperidin-1-yl]sulfonyl}-3-tetrahydro-2H-pyran-4-ylpropan-2-one LC-MS (APCI) m/z 400 (MH+)

1-{[4-(4-chlorophenyl)piperidin-1-yl]sulfonyl}-5-morpholin-4-ylpentan-2-one

LC-MS (APCI) m/z 429 (MH+)

1-({4-[5-trifluoromethyl)pyridin-2-yl]piperazine-1-yl}sulfonyl)propan-2-one

LC-MS (APCI) m/z 352.1 (MH+)

6-{4-[(2-oxopropyl)sulfonyl]piperazin-1-yl}pyridine-3-carbonitrile

LC-MS (APCI) m/z 309.1 (MH+)

1-{[4-(4-fluorophenyl)piperazine-1-yl]sulfonyl}propan-2-one

LC-MS (APCI) m/z 301.1 (MH+)

1-({4-[(4-fluorophenyl)methyl]piperazine-1-yl}sulfonyl)propan-2-one

LC-MS (APCI) m/z 315.1 (MH+)

1-[(4-pyrimidin-2-ylpiperazine-1-yl)sulfonyl]propan-2-one

LC-MS (APCI) m/z 285.1 (MH+)

1,1-dimethylethyl 4-[3-{4-[(5-chloropyridin-2-yl)oxy]piperidin-1-yl}sulfonyl-2-oxopropyl]piperidine-1-carboxylate LC-MS (APCI) m/z 517 (MH+).

HYDANTOINS OF FORMULA I

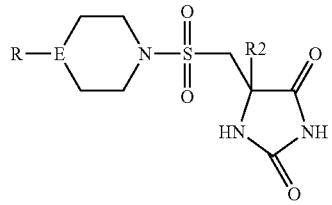

| R | E | R2 | Analysis |
|---|---|----|----------|
| 4-F-phenyl | CH | Me | m/z 370 (MH+)[(1)] |
| 4-F-phenyl | CH | CH2CH2-phenyl | m/z 460 (MH+)[(1)] |
| 4-F-phenyl | CH | CH2CH2CH2-imidazol-1-yl | m/z 464 (MH+)[(1)] |
| 4-F-phenyl | CH | CH2CH2CH2-pyrimidin-2-yl | m/z 476 (MH+)[(1)] |
| 5-Cl-2-methoxypyridin-2-yl | CH | Me | m/z 403 (MH+)[(1)] |
| 5-Cl-2-methoxypyridin-2-yl | CH | CH2CH2-phenyl | m/z 493 (MH+)[(1)] |

-continued

HYDANTOINS OF FORMULA I

| R | E | R2 | Analysis |
|---|---|---|---|
| 5-chloro-2-methoxypyridin-3-yl | CH | butyl-imidazole | m/z 497 (MH+)[1] |
| 5-chloro-2-methoxypyridin-3-yl | CH | butyl-pyrimidine | m/z 509 (MH+)[1] |
| 5-chloro-2-methoxypyridin-3-yl | CH | propyl | m/z 417 (MH+)[1] |
| 5-chloro-2-methoxypyridin-3-yl | CH | butyl | m/z 431 (MH+)[1] |
| 5-chloro-2-methoxypyridin-3-yl | CH | isobutyl | m/z 445 (MH+)[1] |
| 5-chloro-2-methoxypyridin-3-yl | CH | propyl-pyrimidine | m/z 495 (MH+)[1] |
| 5-chloro-2-methoxypyridin-3-yl | CH | 3-methylbenzyl-ethyl | m/z 493 (MH+)[1] |
| 5-chloro-2-methoxypyridin-3-yl | CH | ethyl-tetrahydropyran | m/z 487 (MH+)[1] |
| 5-chloro-2-methoxypyridin-3-yl | CH | butyl-morpholine | m/z 517 (MH+)[1] |
| 5-chloro-2-methoxypyridin-3-yl | CH | propyl-CN | m/z 442 (MH+)[1] |
| 5-chloro-2-methoxypyridin-3-yl | CH | butyl-NHBoc | m/z 547, 490 (MH+), -tBu[1] |
| 5-chloro-2-methoxypyridin-3-yl | CH | propyl-morpholine | m/z 502 (MH+)[2] |

-continued

HYDANTOINS OF FORMULA I

| R | E | R2 | Analysis |
|---|---|---|---|
| 5-Cl, 2-OMe-pyridyl | CH | phenyl | m/z 465 (MH+)[2] |
| 5-Cl, 2-OMe-pyridyl | CH | 4-F-phenyl | m/z 483 (MH+)[2] |
| 5-Cl, 2-OMe-pyridyl | CH | methylimidazolyl | m/z 455 (MH+)[2] |
| 5-Cl, 2-OMe-pyridyl | CH | 4-carboxamidophenyl | m/z 508 (MH+)[2] |
| 5-Cl, 2-OMe-pyridyl | CH | propyl-triazolyl | m/z 484 (MH+)[2] |
| 4-F-phenyl | CH | propyl-pyrimidinyl | m/z 462 (MH+)[1] |
| 4-F-phenyl | CH | ethyl-tetrahydropyranyl | m/z 454 (MH+)[1] |
| 4-F-phenyl | CH | 4-carboxamidophenyl | m/z 475 (MH+)[1] |
| 4-F-phenyl | CH | methylimidazolyl | m/z 422 (MH+)[2] |
| 4-Cl-phenyl | CH | ethyl-tetrahydropyranyl | m/z 470 (MH+)[1] |
| 4-Cl-phenyl | CH | butyl-morpholinyl | m/z 499 (MH+)[1] |
| 5-CF3, 2-methyl-pyridyl | N | Me | m/z 422 (MH+)[1] |

-continued

HYDANTOINS OF FORMULA I

| R | E | R2 | Analysis |
|---|---|----|----------|
| NC-pyridine-methyl (5-cyano-2-methylpyridin-yl) | N | Me | m/z 379 (MH+)[1] |
| 4-fluorophenyl | N | Me | m/z 371 (MH+)[1] |
| 4-fluorophenylethyl | N | Me | m/z 385 (MH+)[1] |
| 2-methylpyrimidin-yl | N | Me | m/z 355 (MH+)[1] |
| 5-chloro-2-methoxypyridin-yl | CH | n-propyl-N | m/z 446 (MH+)[1] |
| 5-chloro-2-methoxypyridin-yl | CH | piperidin-4-ylmethyl | m/z 472 (MH+)[1] |
| 5-chloro-2-methoxypyridin-yl | CH | tetrahydropyran-4-ylmethyl | m/z 403 (MH+)[1] |
| 5-chloro-2-methoxypyridin-yl | CH | pyridin-4-ylmethyl | m/z 466 (MH+)[1] |
| 5-chloro-2-methoxypyridin-yl | CH | N-Boc-piperidin-4-ylethyl | m/z 530 (MH+ − boc)[1] |
| 5-chloro-2-methoxypyridin-yl | CH | piperidin-4-ylethyl | m/z 486 (MH+ − boc)[1] |
| 5-chloro-2-methoxypyridin-yl | CH | N-methanesulfonyl-butylamino | m/z 524 (MH+)[1] |

[1] NMR available, see experimental part.
[2] Not purified.

(5R,S)-5-[4-(4-Fluoro-phenyl)-piperidine-1-sulfonyl-methyl]-5-methyl-imidazolidine-2,4-dione The ketone 1-[4-4(Fluorophenyl)-piperidine-1-sulfonyl]-propan-2-one (68 mg; 0.23 mmol), KCN (30 mg; 0.46 mmol) and $(NH_4)_2CO_3$ (111 mg; 1.16 mmol) was suspended in 50% EtOH/$H_2O$ (8 mL) in a 22 mL sealed tube and heated to 70° C., a solution was formed. The mixture was stirred at 70° C. for 17 h. a solid formed in the tube, the mixture was cooled to room temperature and solvent evaporated, the residue was suspended in water and pH adjusted to pH=6 using 1.0M HCl and precipitated product removed by filtration and washed with water. The water phase was saturated with NaCl and extracted with MeCN. The solid material and MeCN solutions was combined and evaporated. The crude product was purified using a semipreparative HPLC system and a C-18 column with MeCN/$H_2O$+0.1% TFA as eluent. Fractions containing the product was combined and solvent removed by evaporation to give the title compound as a colourless solid.
Obtained 53 mg (62% yield).
Purity by NMR>98%
LC-MS (APCI) m/z 370.0 (MH+).
$^1$H-NMR (DMSO-$d_6$): δ 10.74 (s, 1H), 8.02 (s, 1H), 7.31 (m, 2H), 7.12 (m, 2H), 3.61 (m, 2H), 3.51 (d, 1H), 3.34 (d, 1H), 2.86 (m, 2H), 2.63 (m, 1H), 1.82 (m, 2H), 1.63 (m, 2H), 1.34 (s, 3H).

(5R,S)-5-[4-(4-Fluoro-phenyl)-piperidine-1-sulfonyl-methyl]-5-phenethyl-imidazolidine-2,4-dione The title compound was prepared as described in the synthesis of (5R,S)-5-[4-(4-Fluoro-phenyl)-piperidine-1-sulfonylmethyl]-5-methyl-imidazolidine-2,4-dione. 1-[4-4(Fluorophenyl)-piperidine-1-sulfonyl]-4-phenyl-butan-2-one (93 mg; 0.24 mmol), KCN (40 mg; 0.61 mmol) and $(NH_4)CO_3$ (117 mg; 1.22 mmol) gave 37 mg (33%) of the title compound.
LC-MS (APCI) m/z 460.1 (MH+).
$^1$H-NMR (DMSO-$d_6$): δ 10.87 (s, 1H), 8.13 (s, 1H), 7.30 (m, 4H), 7.15 (m, 5H), 3.63 (m, 2H), 3.56 (d, 1H), 3.41 (d, 1H), 2.87 (m, 2H), 2.61 (m, 2H), 2.39 (m, 1H), 1.92 (bt, 2H), 1.83 (m, 2H), 1.63 (m, 2H).

(5R,S)-5-[4-(4-Fluoro-phenyl)-piperidine-1-sulfonyl-methyl]-5-(3-imidazol-1-yl-propyl)-imidazolidine-2,4-dione 1-[4-4(Fluorophenyl)-piperidine-1-sulfonyl]-5-imidazol-butan-2-one (75 mg; 0.19 mmol), KCN (30 mg; 0.46 mmol) and $(NH_4)_2CO_3$ (91 mg; 0.95 mmol) was dissolved in EtOH/$H_2O$ (1/1) (10 mL) in a sealed 22 mL tube and stirred for 17.5 h at 70° C. Another portion of KCN (40 mg; 0.61 mmol) and $(NH_4)CO_3$ (250 mg; 2.60 mmol) was added and the mixture was stirred at 70° C. for another 16 h. Evaporation of solvent and the residual material was suspended in $H_2O$, precipitating crude product was removed by filtration and purified using a semipreparative HPLC system and a C-18 column with MeCN/$H_2O$+0.1% TFA as eluent. Fractions containing the product was combined and MeCN was removed by evaporation, the acidic waterphase was made basic, pH=8-9, using 5% $KHCO_3$ and the precipitating product was extracted using EtOAc. Organic phase dried ($Na_2SO_4$), filtered and evaporated to give the title compound as a colourless solid.
Obtained 60 mg (68% yield)
LC-MS (APCI) m/z 464.2 (MH+).
$^1$H-NMR (DMSO-$d_6$): δ 10.75 (bs, 1H), 8.06 (s, 1H), 7.59 (s, 1H), 7.30 (m, 2H), 7.16-7.08 (m, 3H), 6.88 (s, 1H), 3.95 (m, 2H), 3.60 (m, 2H), 3.47 (d, 1H), 3.35 (d, 1H), 2.86 (m, 2H), 2.62 (m, 1H), 1.86-1.50 (m, 8H).

(5R,S)-5-[4-(4-Fluoro-phenyl)-piperidine-1-sulfonyl-methyl]-5-(3-pyrimidin-2-yl-propyl)imidazolidine-2,4-dione Crude 1-[4-(4-Fluoro-phenyl)-piperidine-1-sulfonyl]-5-pyrimidin-2-yl-pentan-2-one (234 mg; max 0.58 mmol), KCN (151 mg; 2.3 mmol) and $(NH_4)_2CO_3$ (557 mg; 5.8 mmol) was suspended in EtOH/$H_2O$ (1/1) (26 mL) in a 40 mL sealed tube. The mixture was heated 70° C. and the resulting yellow solution was stirred for 16 h.
LC/MS analysis showed that 15% unreacted ketone remained and another portion of KCN (65 mg; 1 mmol) and $(NH_4)_2CO_3$ (245 mg; 2.55 mmol) was added and the mixture was heated to 70° C. for another 16 h. Solvent was removed by evaporation and the residue was treated with $H_2O$ (25 mL). The precipitating crude product was removed by filtration and purified using semipreparative HPLC system and a C-18 column with MeCN/$H_2O$+0.1% TFA as eluent. Fractions containing the product was combined and MeCN was removed by evaporation, the acidic waterphase was made basic, pH=8-9, using 5% $KHCO_3$ and the precipitating product was filtered off, washed with water and dried in a desiccator under reduced pressure at 40° C. over night. This gave the title compound as a colourless solid. Purity>98% by NMR.
Obtained 120 mg (43% yield, 2 steps).
LC-MS (APCI) m/z 476.2 (MH+).
$^1$H-NMR (DMSO-$d_6$): δ 10.77 (s, 1H), 8.72 (d, 2H), 8.03 (s, 1H), 7.36-7.27 (m, 3H), 7.15-7.09 (m, 2H), 3.60 (m, 2H), 3.50 (d, 1H), 3.34 (d, 1H), 2.92-2.80 (m, 4H), 2.62 (m, 1H), 1.86-1.54 (m, 8H).

The following compounds were prepared as described in the synthesis of (5R,S)-5-[4-(4-Fluoro-phenyl)piperidine-1-sulfonylmethyl]-5-(3-pyrimidin-2-yl-propyl)-imidazolidine-2,4-dione.

(5R,S)-5-[4-(5-Chloro-pyridin-2-yloxy)-piperidine-1-sulfonylmethyl]-5-methyl-imidazolidine-2,4-dione Purification not needed, after evaporation of reaction mixture and addition of water the precipitating product was pure enough >98% by HPLC (220 nm, 254 nm) and NMR Obtained 1.47 mg (71% yield, 2 steps) of the title compound as a colorless solid.
LC-MS (APCI) m/z 403.1 (MH+).
$^1$H-NMR (DMSO-$d_6$): δ 10.73 (bs, 1H), 8.20 (d, 1H), 8.01 (s, 1H), 7.81 (dd, 1H), 6.87 (d, 1H), 5.09 (m, 1H), 3.52 (d, 1H), 3.35 (d, 1H), 3.42-3.26 (m, 2H+$H_2O$), 3.18-3.06 (m, 2H), 2.08-1.96 (m, 2H), 1.79-1.65 (m, 2H), 1.33 (s, 3H).

(5S)-5-[4-(5-Chloro-pyridin-2-yloxy)-piperidine-1-sulfonylmethyl]-5-methyl-imidazolidine-2,4-dione and (5R)-5-[4-(5-Chloro-pyridin-2-yloxy)piperidine-1-sulfonylmethyl]-5-methyl-imidazolidine-2,4-dione The corresponding racemic material (74 mg), was dissolved in 36 mL of isoHexane/EtOH (25/75) and separated into the pure enantiomers by using the following Gilson HPLC system:
Column: CHIRALCEL OD, 2.0×25 cm, flow=6.0 mL/min, eluent=isoHexane/EtOH (25/75), temp=ambient, detector UV=220 nm.
The enantiomers were collected and analysed on a CHIRALCEL OD-H, 0.46×25 cm, 0.5 mL/min, isoHexane/EtOH (25/75), ambient temperature, 220 nm.

Rt=9.88 min. ee>99% for the faster eluting enantiomer, 29 mg (39%).
Rt=11.45 min. ee=98.7% for the slower eluting enantiomer, 27 mg (36%).
LC-MS (APCI) m/z 403.1 (MH+).

(5R,S)-5-[4-(5-Chloro-pyridin-2-yloxy)-piperidine-1-sulfonylmethyl]-5-phenethyl imidazolidine-2,4-dione Starting from crude 1-[4-(5-Chloro-pyridin-2-yloxy)piperidine-1-sulfonyl]-4-phenyl-butan-2-one (258 mg; max 0.51 mmol).
Purification of crude product was made on 70 g Si-60 gel using DCM+5% MeOH as eluent.
Purity>96% by NMR and HPLC (220 nm, 254 nm).
Obtained 201 mg (80% yield, 2 steps) of the title compound as a colourless solid.
LC-MS (APCI) m/z 493.0 (MH+).
$^1$H-NMR (DMSO-$d_6$): δ 10.86 (bs, 1H), 8.21 (bd, 1H), 8.13 (s, 1H), 7.81 (dd, 1H), 7.33-7.24 (m, 2H), 7.22-7.14 (m, 3H), 6.87 (d, 1H), 5.10 (m, 1H), 3.56 (d, 1H), 3.42 (d, 1H), 3.43-3.28 (m, 2H+H$_2$O), 3.20-3.08 (m, 2H), 2.66-2.52 (m, 1H), 2.45-2.31 (m, 1H), 2.08-1.96 (m, 2H), 1.96-1.83 (m, 2H), 1.81-1.65 (m, 2H.

(5R,S)-5-[4-(5-Chloro-pyridin-2-yloxy)-piperidine-1-sulfonylmethyl]-5-(3-imidazol-1yl-propyl)-imidazolidine-2,4-dione Starting from crude 1-[4-(5-Chloro-pyridin-2-yloxy)-piperidine-1-sulfonyl]-5-imidazol-1-yl-pentan-2-one (268 mg; max 0.51 mmol).
Obtained 151 mg (59% yield, 2 steps) of the title compound as a colourless solid.
Purity>98% by NMR.
LC-MS (APCI) m/z 497.2 (MH+).
$^1$H-NMR (DMSO-$d_6$): δ 10.81 (bs, 1H), 8.20 (d, 1H), 3.05 (s, 1H), 7.81 (dd, 1H), 7.59 (bs, 1H), 7.13 (bs, 1H), 6.88 (bs, 1H), 6.87 (d, 1H), 5.08 (m, 1H), 3.47 (d, 1H), 3.40-3.28 (m, 3H+H$_2$O), 3.17-3.06 (m, 2H), 2.07-1.95 (m, 2H), 1.79-1.64 (m, 3H), 1.61-1.48 (m, 3H).

(5R,S)-5-[4-(5-Chloro-pyridin-2-yloxy)piperidine-1-sulfonylmethyl]-5-(3-pyrimidin-2-yl-propyl)-imidazolidine-2,4-dione Starting from crude 1-[4-(5-Chloro-pyridin-2-yloxy)-piperidine-1-sulfonyl]-5-pyrimidin-2-yl-pentan-2-one (244 mg; max 0.51 mmol).
Obtained 105 mg (49% yield, 2 steps) of the title compound as a colourless solid.
Purity>98% by NMR.
$^1$H-NMR (DMSO-$d_6$): δ 10.77 (bs, 1H), 8.72 (d, 2H), 8.20 (d, 1H), 8.03 (s, 1H), 7.81 (dd, 1H), 7.34 (t, 1H), 6.87 (d, 1H), 5.08 (m, 1H), 3.50 (d, 1H), 3.41-3.29 (m, 3H+H$_2$O), 3.16-3.07 (m, 2H), 2.83 (t, 2H), 2.06-1.96 (m, 2H), 1.81-1.66 (m, 5H), 1.63-1.51 (m, 1H).

(5S)-5-[4-(5-Chloro-pyridin-2-yloxy)-piperidine-1-sulfonylmethyl]-5-(3-pyrimidin-2-yl-propyl)-imidazolidine-2,4-dione and (5R)-5-[4-(5-Chloro-pyridin-2-yloxy)-piperidine-1-sulfonylmethyl]-5-(3-pyrimidin-2-yl-propyl)-imidazolidine-2,4-dione The corresponding racemic material (40 mg), was dissolved in 26 mL of isoHexane/EtOH (25/75) and separated into the pure enantiomers by using the same conditions as described for separation of (5R,S)-5-[4-(5-Chloro-pyridin-2-yloxy)-piperidine-1-sulfonylmethyl]-5-methyl-imidazolidine-2,4-dione.
Rt=17.6 min. ee>99% for the faster eluting enantiomer, 17 mg (42%).
Rt=21.0 min. ee=98.9% for the slower eluting enantiomer, 15 mg (37%).
LC-MS (APCI) m/z 509 (MH+).

5-[({4-[(5-chloropyridin-2-yl)oxy]piperidin-1-yl}sulfonyl)methyl]-5-ethylimidazolidine-2,4-dione LC-MS (APCI) m/z 417 (MH+).
$^1$H NMR (DMSO-$d_6$): 0.76 (3H, t); 1.63 (2H, q); 1.66-1.76 (2H, m); 1.96-2.06 (2H, m); 3.12 (2H, bt); 3.48, 3.35 (1H each, ABq, J=14.9); 3.32-3.41 (2H, m); 5.04-5.12 (1H, m); 6.86 (1H, d); 7.80 (1H, dd); 7.96 (1H, s); 8.19 (1H, d); 10.73 (1H, s).
LC-MS (APCI) m/z 417 (MH+).

5-[({4-[(5-chloropyridin-2-yl)oxy]piperidin-1-yl}sulfonyl)methyl]-5-propylimidazolidine-2,4-dione LC-MS (APCI) m/z 431 (MH+).
$^1$H NMR (DMSO-$d_6$): δ 0.84 (3H, t); 1.03-1.16 (1H, m); 1.20-1.35 (1H, m); 1.58 (2H, t); 1.65-1.77 (2H, m); 1.96-2.06 (2H, m); 3.11 (2H, t); 3.21-3.42 (3H, D$_2$O); 3.48 (1H, half ABq, J=14.9); 5.04-5.12 (1H, m); 6.86 (1H, d); 7.80 (1H, dd); 7.99 (1H, s); 8.19 (1H, d); 10.74 (1H, s).

5-[({4-[(5-chloropyridin-2-yl)oxy]piperidin-1-yl}sulfonyl)methyl]-5-(2-methylpropyl)imidazolidine-2,4-dione LC-MS (APCI) m/z 445 (MH+).
$^1$H NMR (DMSO-$d_6$): δ 0.81 (3H, d); 0.88 (3H, d); 1.50-1.59 (3H, m); 1.64-1.78 (2H, m); 1.95-2.05 (2H, m); 3.06-3.16 (2H, m); 3.22-3.41 (3H, D$_2$O); 3.46 (1H half Abq, J=15.1); 5.03-5.12 (1H, m); 6.86 (1H, d); 7.80 (1H, dd); 7.99 (1H, bs); 8.19 (1H, d); 10.71 (1H, bs).

5-[({4-[(5-chloropyridin-2-yl)oxy]piperidin-1-yl}sulfonyl)methyl]-5-(2-pyrimidin-2-ylethyl)imidazolidine-2,4-dione LC-MS (APCI) m/z 495 (MH+).
$^1$H NMR (DMSO-$d_6$): δ 1.66-1.78 (2H, m); 1.96-2.16 (4H, m); 2.64-2.76 (1H, m); 2.84-2.95 (1H, m); 3.08-3.18 (2H, m); 3.33-3.41 (2H, m); 3.43, 3.57 (1H each, ABq, J=14.9); 5.04-5.12 (1H, m); 6.86 (1H, d); 7.34 (1H, t); 7.80 (1H, dd); 8.12 (1H, d); 8.19 (1H, d); 8.70 (1H, d); 10.84 (1H, s).

5-[({4-[(5-chloropyridin-2-yl)oxy]piperidin-1-yl}sulfonyl)methyl]-5-[(3-methylphenyl)methyl]imidazolidine-2,4-dione LC-MS (APCI) m/z 493 (MH+).
$^1$H NMR (DMSO-$d_6$): δ 1.66-1.78 (2H, m); 1.96-2.07 (2H, m); 2.23 (3H, s); 2.84 (2H, s); 3.09-3.20 (2H, m); 3.34-3.43 (2H, m); 3.45, 3.69 (1H each, ABq, J=14.7 Hz); 5.06-5.13 (1H, m); 6.87 (1H, d); 6.93-6.98 (2H, m); 7.01-7.06 (1H, m); 7.10-7.17 (1H, m); 7.81 (1H, dd); 8.08 (1H, s); 8.20 (1H, d); 10.35 (1H, s).

5-[({4-[(5-chloropyridin-2-yl)oxy]piperidin-1-yl}sulfonyl)methyl]-5-(tetrahydro-2H pyran-4-ylmethyl)imidazolidine-2,4-dione LC-MS (APCI) m/z 487 (MH+).
$^1$H NMR DMSO-d$_6$): δ 1.06-1.26 (2H, m); 1.39-1.77 (7H, m); 1.95-2.05 (2H, m); 3.06-3.27 (4H, m); 3.27-3.41 (3H, D$_2$O); 3.48 (1H half ABq, J=15.0 Hz); 3.69-3.79 (2H, m); 5.03-5.12 (1H, m); 6.85 (1H, d); 7.80 (1H, dd); 8.03 (1H, bs); 8.19 (1H, d); 10.79 (1H, s).

5-[({4-[(5-chloropyridin-2-yl)oxy]piperidin-1-yl}sulfonyl)methyl]-5-(3-morpholin-4-ylpropyl)imidazolidine-2,4-dione trifluoroacetic acid LC-MS (APCI) m/z 517 (MH+).
$^1$H NMR (DMSO-d$_6$): δ 1.40-1.78 (6H, m); 1.96-2.06 (2H, m); 2.94-3.18 (6H, m); 3.31-3.44 (5H, m); 3.54 (1H half Abq, J=14.9 Hz); 3.60 (2H, t); 3.90-4.01 (2H, m); 4.25-6.27 (1H); 6.85 (1H, d); 7.80 (1H, dd); 8.05 (1H, bs); 8.19 (1H, d); 9.52 (1H, bs); 10.88 (1H, s).

3-{4-[({4-[5-chloropyridin-2-yl)oxy]piperidin-1-yl}sulfonyl)methyl]-2,5-dioxoimidazolidin-4-yl}propanenitrile LC-MS (APCI) m/z 442 (MH+).
$^1$H NMR (DMSO-d$_6$): δ 1.66-1.78 (2H, m); 1.95-2.05 (4H, m); 2.37-2.57 (2H, DMSO-d$_6$); 3.07-3.17 (2H, m); 3.25-3.40 (2H, D$_2$O); 3.42, 3.52 (1H each, Abq, J=14.7); 5.04-5.12 (1H, m); 6.86 (1H, d); 7.80 (1H, dd); 7.99 (1H, bs); 8.20 (1H, d); 10.91 (1H, s).

1,1-dimethylethyl 3-{4-[({4-[(5-chloropyridin-2-yl)oxy]piperidin-1-yl}sulfonyl)methyl]-2,5-dioxoimidazolidin-4-yl}propylcarbamate LC-MS (APCI) m/z 547, 490 (MH+); (MH+)-tBu.
$^1$H NMR (DMSO-d$_6$): δ 1.10-1.27 (1H, m); 1.27-1.43 (9H, s); 1.52-1.77 (4H, m); 1.94-2.06 (2H, m); 2.80-2.90 (2H, m); 3.06-3.16 (2H, m); 3.22-3.40 (4H, D$_2$O); 3.47 (1H half ABq, J=15.1 Hz); 5.03-5.12 (1H, m); 6.76-6.88 (2H, m); 7.80 (1H, dd); 7.95 (1H, bs); 8.19 (1H, d); 10.73 (1H, bs).

5-[({4-[(5-chloropyridin-2-yl)oxy]piperidin-1-yl}sulfonyl)methyl]-5-(2-morpholin-4-ylethyl)imidazolidine-2,4-dione Not purified.
LC-MS (APCI) m/z 502 (MH+).

5-[({4-[(5-chloropyridin-2-yl)oxy]piperidin-1-yl}sulfonyl)methyl]-5-phenylimidazolidine-2,4-dione Not purified.
LC-MS (APCI) m/z 465 (MH+).

5-[({4-[(5-chloropyridin-2-yl)oxy]piperidin-1-yl}sulfonyl)methyl]-5-(4-fluorophenyl)imidazolidine-2,4-dione Not purified.
LC-MS (APCI) m/z 483 (MH+).

5-[({4-[(5-chloropyridin-2-yl)oxy]piperidin-1-yl}sulfonyl)methyl]-5-(1H-imidazol-4-yl)imidazolidine-2,4-dione Not purified.
LC-MS (APCI) m/z 455 (MH+).

4-{4-[({4-[(5-chloropyridin-2-yl)oxy]piperidin-1-yl}sulfonyl)methyl]-2,5-dioxoimidazolidin-4-yl}benzamide Not purified.
LC-MS (APCI) m/z 508 (MH+).

5-[({4-[(5-chloropyridin-2-yl)oxy]piperidin-1-yl}sulfonyl)methyl]-5-[2-(1H-1,2,4-triazol-1-yl)ethyl]imidazolidine-2,4-dione Not purified.
LC-MS (APCI) m/z 484 (MH+).

5-({[4-(4-fluorophenyl)piperidin-1-yl]sulfonyl}methyl)-5-(2-pyrimidin-2-ylethyl)imidazolidine-2,4-dione LC-MS (APCI) m/z 462 (MH+).
$^1$H NMR (DMSO-d$_6$): δ 1.62 (2H, dq); 1.77-1.86 (2H, m); 2.07-2.19 (2H, m); 2.57-2.76 (2H, m); 2.81-2.96 (3H, m); 3.42, 3.56 (1H each, ABq, J=14.6 Hz); 3.59-3.68 (2H, m); 7.11 (2H, t); 7.27-7.36 (3H, m); 8.08 (1H, bs); 8.71 (1H, d); 10.84 (1H, bs).

5-({[4-(4-fluorophenyl)piperidin-1-yl]sulfonyl}methyl)-5-(tetrahydro-2H-pyran-4-ylmethyl)imidazolidine-2,4-dione LC-MS (APCI) m/z 454 (MH+).
$^1$H NMR (DMSO-d$_6$): δ 1.07-1.28 (2H, m); 1.40-1.68 (7H, m); 1.77-1.85 (2H, m); 2.56-2.67 (1H, m); 2.85 (2H, dq); 3.22 (2H, dq); 3.39-3.45 (1H, m); 3.48 (1H half ABq, J=14.5 Hz); 3.53-3.66 (2H, m); 3.75 (2H, dt); 7.11 (2H, t); 7.26-7.33 (2H, m); 8.00 (1H, bs); 10.68 (1H, bs).

4-[4-({[4-(4-fluorophenyl)piperidin-1-yl]sulfonyl}methyl)-2,5-dioxoimidazolidin-4-yl]benzamide LC-MS (APCI) m/z 475 (MH+).
$^1$H NMR (DMSO-d$_6$): δ 1.61 (2H, dq); 1.77-1.88 (2H, m); 2.58-2.69 (1H, m); 2.85-3.01 (2H, m); 3.60 (1H half ABq, J=14.6 Hz); 3.60-3.69 (2H, m); 7.12 (2H, t); 7.26-7.34 (2H, m); 7.42 (1H, bs); 7.65 (2H, d); 7.91 (2H, d); 8.01 (1H, bs); 8.85 (1H, s); 10.95 (1H, bs).

5-({[4-(4-fluorophenyl)piperidin-1-yl]sulfonyl}methyl)-5-(1H-imidazol-4-yl)imidazolidine-2,4-dione Not purified.
LC-MS (APCI) m/z 422 (MH+).

5-({[4-(4-chlorophenyl)piperidin-1-yl]sulfonyl}methyl)-5-(tetrahydro-2H-pyran-4-ylmethyl)imidazolidine-2,4-dione LC-MS (APCI) m/z 470 (MH+).
$^1$H NMR DMSO-$d_6$): δ 1.07-1.28 (2H, m); 1.40-1.68 (7H, m); 1.76-1.85 (2H, m); 2.56-2.68 (1H, m); 2.85 (2H, q); 3.22 (2H, q); 3.48 (1H half ABq, J=14.5 Hz); 3.53-3.67 (2H, m); 3.75 (2H, t); 7.26-7.37 (4H, m); 8.02 (1H, bs); 10.79 (1H, bs).

5-({[4-(4-chlorophenyl)piperidin-1-yl]sulfonyl}methyl)-5-(3-morpholin-4-ylpropyl)imidazolidine-2,4-dione trifluoroacetic acid LC-MS (APCI) m/z 499 (MH+).
$^1$H NMR (DMSO-$d_6$): δ 1.41-1.87 (8H, m); 2.56-2.69 (1H, m); 2.86 (2H, q); 2.95-3.14 (4H, m); 3.33-3.44 (3H, m); 3.52 (1H half ABq, J=14.6 Hz); 3.55-3.69 (4H, m); 3.90-4.00 (2H, m); 7.25-7.37 (4H, m); 8.07 (1H, s); 9.89 (1H, bs); 10.87 (1H, s).

(5R,S)-5-Methyl-5-[({4-[5-trifluoromethyl)pyridin-2-yl]piperazine-1-yl}sulfonyl)methyl]imidazolidine-2,4-dione LC-MS (APCI) m/z 422.1 (MH+).
Purity>95% by NMR.
$^1$H-NMR (DMSO-$d_6$): δ 10.75 (1H, s); 8.44 (1H, d); 8.02 (1H, s); 7.85 (1H, dd); 7.03 (1H, d); 3.75 (4H, m); 3.55 (1H, d); 3.35 (1H, d); 321 (4H, m); 1.31 (3H, s).

6-(4-{[({4R,S}-4-methyl-2,5-dioxoimidazolidin-4-yl)methyl]sulfonyl}piperazin-1-yl)pyridine-3-carbonitril LC-MS (APCI) m/z 379.1 (MH+).
Purity>99% by NMR.
$^1$H-NMR (DMSO-$d_6$): δ 10.74 (1H, s); 8.52 (1H, d); 8.00 (1H, s); 7.90 (1H, dd); 7.00 (1H, d); 3.78 (4H, m); 3.55 (1H, d); 3.36 (1H, d); 3.20 (4H, m); 1.31 (3H, s).

(5R,S)-5-({[4-(4-fluorophenyl)piperazine-1-yl]sulfonyl}methyl)-5-methylimidazolidine-2,4-dione LC-MS (APCI) m/z 371.1 (MH+).
Purity>98% by NMR.
$^1$H-NMR (DMSO-$d_6$): δ 10.75 (1H, s); 8.03 (1H, s); 7.11-6.95 (4H, m); 3.56 (1H, d); 3.36 (1H, d); 3.25 (4H, m); 3.15 (4H, m); 1.33 (3H, s).

(5R,S)-5-[({4-[(4-fluorophenyl)methyl]piperazine-1-yl}sulfonyl)methyl]-5-methylimidazolidine-2,4-dione LC-MS (APCI) m/z 385.1 (MH+).
Purity>95% by NMR.
$^1$H-NMR (DMSO-$d_6$): δ 10.72 (1H, s); 7.99 (1H, s); 7.33 (2H, m); 7.15 (2H, m); 3.50 (2H, s); 3.49 (1H, d); 3.30 (1H, d); 3.12 (4H, m); 2.42 (4H, m); 1.32 (3H, s).

(5R,S)-5-methyl-5-{[(4-pyrimidin-2-ylpiperazine-1-yl)sulfonyl]methyl}imidazolidine-2,4-dione LC-MS (APCI) m/z 355.1 (MH+).
Purity>99% by NMR.
$^1$H-NMR (DMSO-$d_6$): δ 10.74 (1H, s); 8.40 (2H, d); 8.01 (1H, s); 6.68 (1H, t); 3.83 (4H, m); 3.53 (1H, d); 3.33 (1H, d); 3.18 (4H, m); 1.31 (3H, s).

5-(3-aminopropyl)-5-[({4-[(5-chloropyridin-2-yl)oxy]piperidin-1-yl}sulfonyl)methyl]imidazolidine-2,4-dione trifluoroacetic acid 1,1-dimethylethyl 3-{4-[({4-[(5-chloropyridin-2-yl)oxy]piperidin-1-yl}sulfonyl)methyl]-2,5-dioxoimidazolidin-4-yl}propylcarbamate (426 mg, 0.78 mmol) was dissolved in 10 mL $CH_2Cl_2$ and 4 mL of TFA was added. The reaction was stirred at rt for 1 hour. The solvent was removed to give 408 mg (93%) of the title compound as a white solid.
LC-MS (APCI) m/z 446 (MH+).
$^1$H NMR (CD$_3$OD): δ 1.48-1.63 (1H, m); 1.69-1.96 (5H, m); 2.01-2.12 (2H, m); 2.93 (2H, t); 3.20-3.29 (2H, m); 3.40, 3.60 (1H each ABq, J=14.6 Hz); 3.44-3.54 (2H, m); 4.85 (4H, D$_2$O); 5.14-5.22 (1H, m); 6.78 (1H, d); 7.67 (1H, dd); 8.08 (1H, d).

5-[4-(5-Chloro-pyridin-2-yloxy)-piperidine-1-sulfonylmethyl]-5-piperidin-4-yl-imidazolidine-2,4-dion hydro chloride 4-{4-[4-(5-Chloro-pyridin-2-yloxy)-piperidine-1-sulfonylmethyl]-2,5-dioxo-imidazolidin-4-yl}-piperidine-1-carboxylic acid tert-butyl ester (100 mg, 0.16 mmol) was solved in 2 M hydrogen chloride (ethyl acetate, 30 ml) and methanol (5 ml). The solution was stirred at 50° C. for 1 hour. Evaporation afforded 90.5 mg (0.16 mmol) of the title compound 5-[4-(5-Chloro-pyridin-2-yloxy)-piperidine-1-sulfonylmethyl]-5-piperidin-4-yl-imidazolidine-2,4-dion hydro chloride in quantitative yield.
LC-MS (APCI) m/z 472.3 (MH+).
$^1$H NMR (DMSO-$d_6$): δ10.88 (1H, s); 9.05 (1H, d); 8.48 (1H, m); 8.21 (1H, d); 7.82 (1H, dd); 6.87 1H, d); 5.10 1H, m); 3.47 (2H, s); 3.43-3.13 (7H, m); 2.78 (2H, m); 2.02-1.39 (9H, m).

4-{4-[4-(5-Chloro-pyridin-2-yloxy)-piperidine-1-sulfonylmethyl]-2,5-dioxo-imidazolidin-4-}-piperidine-1-carboxylic acid tert-butyl ester For preparation of the reacting ester, piperidine-1,4-dicarboxylic acid 1-tert-butyl ester 4-methyl ester, se for example Albert A Carr et al, Journal of Organic Chemistry (1990), 55(4), 1399-401.
LC-MS (APCI) m/z 472.3 (MH+-Boc).

5-[4-(5-Chloro-pyridin-2-yloxy)-piperidine-1-sulfonylmethyl]-5-(tetrahydro-pyran-4-yl)-2,4-dion LC-MS (APCI) m/z 403.2 (MH+).
$^1$H NMR (DMSO-$d_6$): δ 10.77 (1H, s); 8.20 (1H, d); 8.19 (1H, s); 7.81 (1H, dd); 6.87 (1H, d); 5.09 (1H, m); 3.88 (2H, t); 3.45 (2H, s); 3.38 (2H, m); 3.21 (2H, t); 3.13 (2H, m); 2.02 (2H, m); 1.84 (1H, t); 1.72 (2H, m); 1.60 (1H, d); 1.32 (4H, m).

5-[4-(5-Chloro-pyridin-2-yloxy)-piperidine-1-sulfonylmethyl]-5-pyridin-4-yl-imidazolidine-2,4-dion trifluoroacetic acid LC-MS (APCI) m/z 466.2 (MH+).
$^1$H NMR (DMSO-$d_6$): δ 11.15 (1H, s); 8.97 (1H, s); 8.76 (2H, d); 8.20 (1H, d); 7.82 (2H, dd); 7.80 (1H, d); 6.86 (1H, d); 5.10 (1H, my, 4.17 (1H, m); 3.73 (1H, d); 3.41 (2H, m); 3.17 (2H, m); 2.08 (2H, m); 1.72 (2H, m).

1,1-dimethylethyl 4-({4-[({4-[(5-chloropyridin-2-yl)oxy]piperidin-1-yl}sulfonyl)methyl]-2,5-dioxoimidazolidin-4}ylmethyl)piperidine-1-carboxylate The title compound was prepared essentially as described in the synthesis of (5R,S)-5-[4-(4-Fluoro-phenyl)-piperidine-1-sulfonylmethyl]-5-methyl-imidazolidine-2,4-dione LC-MS (APCI) m/z 530 (MH+-boc).

$^1$H NMR (DMSO-$d_6$): δ 0.88-1.10 (2H, m); 1.30-1.77 (16H, m); 1.94-2.06 (2H, m); 2.53-2.77 (2H, m); 3.05-3.17 (2H, m); 3.21-3.41 (4H, D$_2$O); 3.48 (1H half ABq, J=14.7 Hz); 3.73-3.88 (2H, m); 5.03-5.12 (1H, m); 6.86 (1H, d); 7.80 (1H, dd); 8.04 (1H, bs); 8.19 (1H, d); 10.55 (1H, bs).

5-[({4-[(5-chloropyridin-2-yl)oxy]piperidin-1-yl}sulfonyl)methyl]-5-(piperidin-4-ylmethyl)imidazolidine-2,4-dione trifluoroacetate The title compound was prepared as described in the synthesis of 5-(3-aminopropyl)-5-[({4-[(5-chloropyridin-2-yl)oxy]piperidin-1-yl}sulfonyl)methyl]imidazolidine-2,4-dione trifluoroacetic acid LC-MS (APCI) m/z 486 (MH+).

$^1$H NMR (DMSO-$d_6$): δ 1.17-1.40 (2H, m); 1.47-1.81 (7H, m); 1.94-2.07 (2H, m); 2.75-2.93 (2H, m); 3.06-3.42 (7H, m); 3.50 (1H half ABq, J=15.6 Hz); 5.04-5.12 (1H, m); 6.85 (1H, d); 7.80 (1H, dd); 8.06 (1H, s); 8.08-8.22 (2H, m); 8.45 (1H, bd); 10.85 (1H, s).

N-(3-{4-[({4-[(5-chloropyridin-2-yl)oxy]piperidin-1-yl}sulfonyl)methyl]-2,5-dioxoimidazolidin-4-yl}propyl)methanesulfonamide 5-(3-Aminopropyl)-5-[({4-[(5-chloropyridin-2-yl)oxy]piperidin-1-yl}sulfonyl)methyl]imidazolidine-2,4-dione trifluoroacetic acid (100 mg, 0.18 mmol) was slurried in 2 mL DCM. DIPEA (624 μL, 0.36 mmol) was added and the slurry was stirred for some minutes. Sulfonylchloride (16 μL, 0.18 mmol) was added and the reaction was stirred at rt over night. The crude product was purified by preparative HPLC.

LC-MS (APCI) m/z 524 (MH+).

$^1$H NMR (DMSO-$d_6$): δ 1.19-1.52 (2H, m); 1.58-1.77 (4H, m); 1.95-2.06 (2H, m); 2.85 (3H, s); 2.83-2.93 (2H, m); 3.12 (2H, t); 3.19-3.46 (3H, D$_2$O); 3.50 (1H half ABq, J=15.7 Hz); 5.04-5.12 (1H, m); 6.86 (1H, d); 6.97 (1H, t); 7.80 (1H, dd); 8.01 (1H, s); 8.19 (1H, d); 10.79 (1H, s).

EXAMPLE 9

(5R,S)-5-[4-(5-Chloro-pyridin-2-yl)-piperazine-1-sulfonylmethyl]-5-(3-pyrimidin-2-yl-propyl)-imidazolidine-2,4-dione

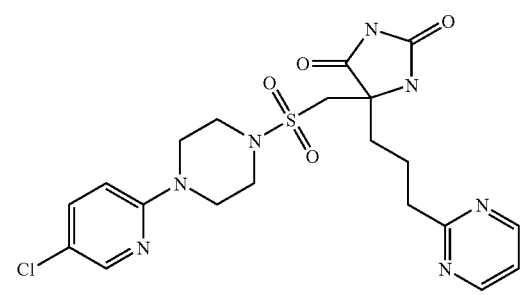

1-([4-(5-Chloro-2-pyridinyl)-1-piperazinyl]sulfonyl)-5-(2-pyrimidinyl)-2-pentanone (0.397 g, 0.936 mmol), potassium cyanide (0.122 g, 1.87 mmol), ammonium carbonate (0.500 g, 4.68 mmol) and 50% ethanol (4 mL) were stirred in a sealed vial at 75° C. (oil temp) for 17 hours. The ethanol was removed by rotary evaporation, pH was adjusted to 6 with 1M HCl, the suspension was filtered, the solid was washed with a little water, collected and dried in vacuo at 45° C. Some more product was recovered from the aqueous filtrate by adding solid sodium chloride to saturation and extracting the mixture with acetonitrile (2×10 mL). Drying with Na$_2$SO$_4$, filtering and concentrating the organic phase gave a second crop. The combined crops were dissolved in tetrahydrofuran (5-10 mL), adsorbed on silica (3 g) and applied on a short silica column. Elution with EtOAc followed by EtOAc-MeCN (1:1) gave 0.30 g (65% yield) of the title compound as a white crystalline solid.

LC-MS (APCI) m/z 494 (MH+).

$^1$H NMR (DMSO-d) δ 10.78 (1H, bs); 8.70 (2H, d, J=5 Hz); 8.13 (1H, d, J=3 Hz); 8.02 (1H, s); 7.63 (1H, dd, J$_1$=3 Hz, J$_2$=9 Hz); 7.33 (1H, t, J=5 Hz); 6.93 (1H, d, J=10 Hz); 3.63-3.56 (4H, m); 3.52 (1H, d, J=14 Hz); 3.34 (1H, d, J=14 Hz; obscured by water signal), 3.24-3.14 (4H, m); 2.82 (2H, t, J=7 Hz) and 1.79-1.50 (4H, ms). $^{13}$C NMR (DMSO-$d_6$) δ 175.6, 169.5, 157.2, 157.0, 156.5, 145.6, 137.3, 119.2, 119.1, 108.8, 62.4, 52.7, 44.5, 38.2, 36.4 and 21.2.

The starting materials were prepared as follows:

1-([4-(5-Chloro-2-pyridinyl)-1-piperazinyl]sulfonyl)-5-(2-pyrimidinyl)-2-pentanone

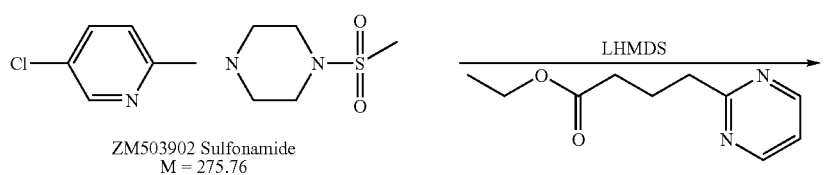

ZM503902 Sulfonamide
M = 275.76

ZM503902 Ester
M = 194.23

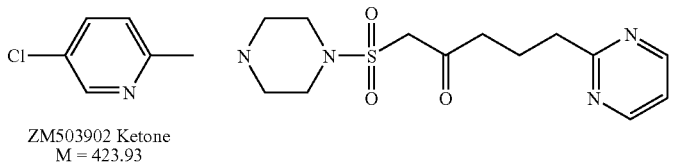

ZM503902 Ketone
M = 423.93

A stirred solution of 1-(5-Chloro-2-pyridinyl)-1-methylsulfonyl piperazine (0.64 g, 2.32 mmol) in dry THF (25 mL, 40 rel vol), under nitrogen, was cooled to −10° C. causing the sulfonamide to precipitate out of solution. LHMDS 1M in THF (4.64 mL, 4.64 mmol) was added dropwise, over 4 min. to the suspension of sulfonamide, the mixture was then stirred for 40 min. 4-(2-Pyrimidinyl)-butyric acid ethyl ester (0.68 g, 3.48 mmol) (example 8) in dry THF (6.4 mL, 10 rel vol) was added dropwise, over 4 min, and the mixture stirred for 30 min. The mixture was quenched with saturated $NH_4Cl$ (0.64 mL, 1 rel vol) and evaporated to a semi-solid residue. The residue was taken up in DCM (20 rel vol) and the organic layer was washed with water (15 mL, 24 rel vol), brine (15 mL, 24 rel vol), and dried with $MgSO_4$. Removal of the solvent by rotary evaporation gave the crude product as an off white solid (0.84 g, 85%). The crude product was purified by Biotage FLASH chromatography, using ethyl acetate/isohexane (90:10) as eluant, to give pure ketone as a white amorphous solid.

1-(5-Chloro-2-pyridinyl)-1-methylsulfonyl piperazine

To a solution containing 1-(5-Chloro-2-pyridinyl)-piperazine (1 eq.) in toluene (25 volumes) is added triethylamine (1.1 eq), and the mixture is cooled down to 5° C. in an ice bath. Methanesulfonyl chloride diluted with toluene (0.5 vols) is slowly added to the cooled solution, keeping the temperature below 10° C. Once the addition is finished, the reaction is allowed to warm-up to room temperature. Water (6.6 vols) is added and the mixture is filtered and cake slurried in Toluene (2 vols). The cake is then washed with Toluene (2 vols) and dried in a vacuum oven at 40° C. overnight.

1-(5-Chloro-2-pyridinyl)-piperazine

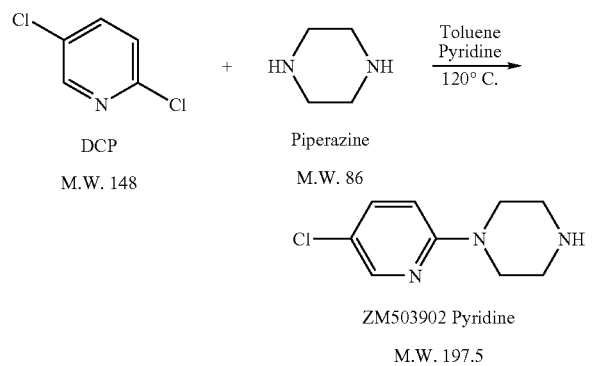

Piperazine (4 eq) is charged in the reaction vessel as a solid. At room temperature pyridine (1.43 vols) is added to the vessel followed by toluene (2.14 vols). The final slurry is stirred and heated to reflux at 120° C. to obtain a complete solution. To a separate vessel charge 2,5-dichloropyridine (DCP) followed by Toluene (1.43 vols) to dissolve the solid. The dissolution is endothermic, and it is necessary to warm up the solution to ~30° C. to get complete solution. The solution containing DCP is then slowly discharged into the reaction vessel over 5 hours. At this point the remaining amount of DCP should be about 20%. The reaction is left refluxing overnight to reach completion.

The reaction mixture is allowed to cool to room temperature, then water is added (6 vols). The two layers are separated, and the aqueous phase is re-extracted with Toluene (5 vols). The two organic layers are combined and re-washed with $H_2O$ (6 vols). Finally, the organic layer is washed with brine (6 vols).

(5S)-5-[4-(5-Chloro-pyridin-2-yl)-piperazine-1-sulfonylmethyl]-5-(3-pyrimidin-2-yl-propyl)-imidazolidine-2,4-dione and 5R)-5-[4-(5-Chloro-pyridin-2-yl)piperazine-1-sulfonylmethyl]-5-(3-pyrimidin-2-yl-propyl)imidazolidine-2,4-dione The corresponding racemic material (23 mg) was dissolved in 8 mL of isoHexane/EtOH (25/75) and separated into the pure enantiomers by using the following Gilson HPLC system:

Column: CHIRALCEL OD, 2.0×25 cm, flow=6.0 mL/mmin, eluent=isoHexane/EtOH (25/75), temp=ambient, detector UV=230 nm.

The enantiomers were collected and analysed on a CHIRALCEL OD-H, 0.46×25 cm, 0.5 mL/min, isoHexane/EtOH (25/75), ambient temperature, 220 nm.

Rt=11.5 min. ee>99% for the faster eluting enantiomer, 8.7 mg (37%).

LC-MS (APCI) m/z 494.1 (MH+).

$[\alpha]_D$=−26.4° (c=0.0022 g/mL, EtOH, t=20° C.)

Rt=14.5 min. ee=98% for the slower eluting enantiomer, 9 mg (39%).

LC-MS (APCI) m/z 494.1 (MH+).

$[\alpha]_D$=+24.50 (c=0.0026 g/mL, EtOH, t=20° C.)

EXAMPLE 10

The following compounds were prepared using a method analogous to that described in Example 8 or 9.

| | |
|---|---|
| 5-[4-(4-Chloro-phenyl)-piperazine-1-sulfonylmethyl]-5-(3-pyrimidin-2-yl-propyl)-imidazolidine-2,4-dione | 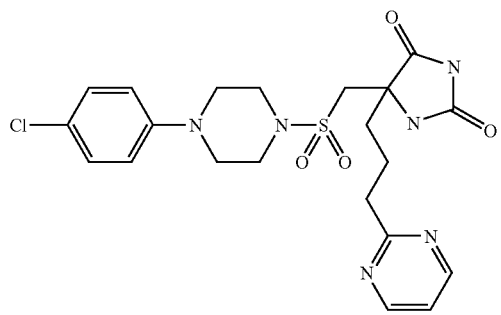<br>m/z 493 (MH+) |
| 5-[4-(4-Fluoro-phenyl)-piperazine-1-sulfonylmethyl]-5-[2-(5-fluoro-pyrimidin-2-yl)-ethyl]-imidazolidine-2,4-dione | 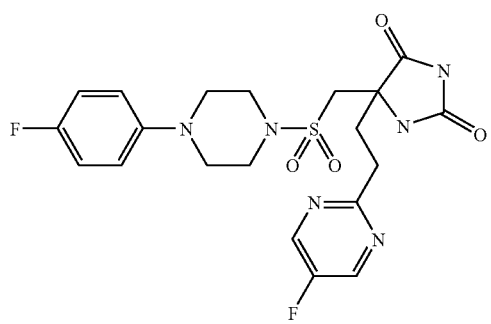<br>m/z 481 (MH+) |
| 5-[4-(5-Chloro-pyridin-2-yl)-piperazine-1-sulfonylmethyl]-5-[2-(5-fluoro-pyrimidin-2-yl-ethyl]-imidazolidine-2,4-dione | 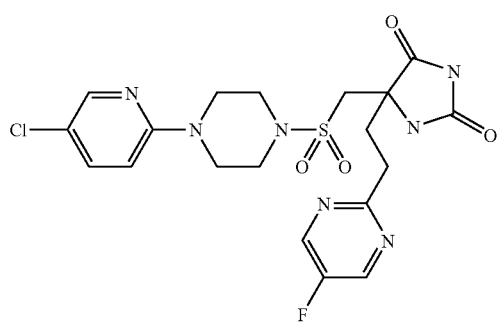<br>m/z 498 (MH+) |
| 5-[4-(3,4-Dichloro-phenyl)-piperazine-1-sulfonylmethyl]-5-(3-pyrimidin-2-yl-propyl)-imidazolidine-2,4-dione | 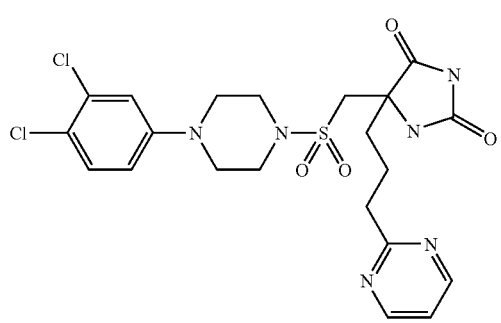<br>m/z 527 (MH+) |

EXAMPLE 11

Compounds with the general formula

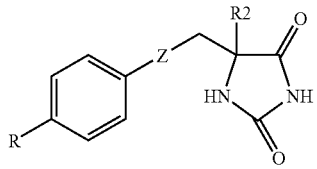

were synthesised according to the method described in Example 8

KETONE INTERMEDIATES

| R | R2 | z | Analysis[1] |
|---|----|----|-------------|
| phenyl | Me | S | GC/MS m/z 242 (M+) |
| 4-NC-phenyl | Me | S | GC/MS m/z 267 (M+) |
| 4-(OCF₃)-phenyl | Me | S | GC/MS m/z 326 (M+) |
| phenyl | Me | SO2 | LC/MS m/z 275 (MH+) |
| 4-NC-phenyl | Me | SO2 | — |

[1]For NMR-data see experimental part.

1-(1,1'-biphenyl-4-ylthio)propan-2-one

1-[(4-bromophenyl)thio]propan-2-one (357 mg, 1.46 mmol) was treated with phenyl boronic acid (231 mg, 1.89 mmol), [1,1'-bis(diphenylphosphino)ferrocene]dichloro palladium (II) complex with dichloromethane (1:1) (36 mg), toluene (20 ml), methanol (7.5 ml), saturated sodium carbonate solution (3.5 ml) and were stirred together at 80° C. for 18 hours. After cooling the reaction mixture was treated with dilute hydrochloric acid and extracted into ethyl acetate. The product was purified by flash chromatography on silica, eluting with 25% ethyl acetate: iso-hexane to give 277 mg product GC/MS m/z: 242 [M+].

$^1$H NMR (CDCl$_3$): δ 2.33 (3H, s); 3.73 (2H, s); 7.37 (1H, s); 7.42-7.48 (4H, m); 7.54-7.59 (4H, m).

The following compounds were prepared as described in the synthesis of 1-(1,1'-biphenyl-4-ylthio)propan-2-one

4'-[(2-oxopropyl)thio]-1,1'-biphenyl-4-carbonitrile

GC/MS m/z: 267 [M+].
$^1$H NMR (CDCl$_3$): δ 2.34 (3H, s); 3.75 (2H, s); 7.44, 7.54 (4H, abq, J=8.5 Hz); 7.67, 7.74 (4H, abq, J=8.5 Hz).

1-({4'-[(trifluoromethyl)oxy]-1,1'-biphenyl-4-yl}thio)propan-2-one

GC/MS m/z: 326 [M+].
$^1$H NMR (CDCl$_3$): δ 2.34 (3H, s); 3.73 (2H, s); 7.30 (2H, d); 7.43 (2H, d); 7.51 (2H, d); 7.58 (2H, d).

1-(1,1'-biphenyl-4-ylsulfonyl)propan-2-one 1-(1,1'-biphenyl-4-ylthio)propan-2-one (69 mg, 0.28 mmol) was stirred at room temperature with sodium bicarbonate (72 mg, 0.85 mmol), oxone ((525 mg, 0.85 mmol), water (5 ml) and methanol (10 ml) for 3 hours. Water (50 ml) was added and the product extracted into ethyl acetate (3×25 ml). The extracts were brine washed, sodium sulphate dried and evaporated to give 78 mg (99%) product that was of sufficient purity to use with out further purification.

LC-MS (APCI) m/z 275 (MH+).
$^1$H NMR (CDCl$_3$): δ 2.47 (3H, s); 4.22 (2H, s); 7.44-7.54 (3H, m); 7.64 (2H, d); 7.80, 7.97 (4H, abq, J=8.6 Hz).

4'-[(2-oxopropyl)sulfonyl]-1,1'-biphenyl-4-carbonitrile

The title compound was prepared as described in the synthesis of 1-(1,1'-biphenyl-4-ylsulfonyl)propan-2-one.
$^1$H NMR (DMSO-d$_6$): δ 2.48 (3H, s); 4.23 (2H, s); 7.74 (2H, d); 7.81 (4H, t); 8.02 (2H, d).

Hydantoins of Formula I

The following compounds were prepared as described in the synthesis of (5R,S)-5-[4-(4-Fluoro-phenyl)-piperidine-1-sulfonylmethyl]-5-methyl-imidazolidine-2,4-dione (Example 8).

| R | R2 | z | Analysis[1] |
|---|----|----|-------------|
| 5-Cl-2-methoxy-pyridinyl | Me | SO2 | m/z 396 (MH+) |
| 4-(OCF₃)-phenyl | Me | S(O) | m/z 413 (MH+) |
| phenyl | Me | SO2 | m/z 345 (MH+) |
| 4-NC-phenyl | Me | SO2 | m/z 370 (MH+) |

[1]For NMR-data see experimental part.

(5R,S)-[4-(5-Chloro-pyridin-2-yloxy)-benzenesulfonylmethyl]-5-methyl-imidazolidine-2,4-dione LC-MS (APCI) m/z 396 (MH+).
$^1$H NMR (DMSO-d$_6$): δ 1.27 (3H, s); 3.71, 3.78 (1H each, ABq, J=15.0); 7.23 (1H, d); 7.36-7.41 (2H, m); 7.82-7.87 (3H, m); 8.04 (1H, dd); 8.27 (1H, d); 10.79 (1H, s).

5-chloro-2-{[4-(methylsulfonyl)phenyl]oxy}pyridine 2,5-dichloropyridine (1.48 g; 10 mmol), 4-methylsulfonylphenol (1.89 g; 11 mmol) and Cs$_2$CO$_3$ (4.24 g; 13 mmol) was slurried in 75 mL of NMP. The slurry was heated to approx 170° C. over night. After cooling the Cs$_2$CO$_3$ was filtered off and the solvent was extracted between H$_2$O and EtOAc. The organic phase was dried over Na$_2$SO$_4$ and evaporated. Heptane:EtOAc 2:1 was added to the residue and the crystals was filtered off. 1.42 g (50%).

LC-MS (APCI) m/z 284 (MH+).
$^1$H NMR CDCl$_3$: δ 3.09 (3H, s); 7.02 (1H, d); 7.33 (2H, d); 7.76 (1H, dd); 8.00 (2H, d); 8.17 (1H, s).

5-methyl-5-[({4'-[(trifluoromethyl)oxy]-1,1'-biphenyl-4-yl}sulfinyl)methyl]imidazolidine-2,4-dione 5-methyl-5-[({4'-[(trifluoromethyl)oxy]-1,1'-biphenyl-4-yl}thio)methyl]imidazolidine-2,4-dione (48 mg, 0.112 mmol) was stirred at room temperature with oxone (50 mg), sodium bicarbonate (50 mg), water (5 ml) and Methanol (10 ml) for 18 hours. The solid was filtered off and crystallized from ethanol to give 20 mg of the title compound.

LC-MS (APCI) m/z very weak 413 (MH+).
$^1$H NMR (DMSO-d$_6$): δ 1.41 (3H, s); 3.04-3.27 (2H, m); 7.47 (2H, d); 7.67-7.73 (2H, m); 7.78-7.90 (5H, m); 8.21 and 8.37 (1H, 2 s); 10.79 and 10.91 (1H, 2 s)

5-methyl-5-[({4'-[(trifluoromethyl)oxy]-1,1'-biphenyl-4-yl}thio)methyl]imidazolidine-2,4-dione LC-MS (APCI) m/z very weak 397 (MH+).
$^1$H NMR (DMSO-d$_6$): δ 1.33 (3H, s); 3.29 (2H, s); 7.42-7.45 (4H, m); 7.61 (2H, d); 7.77 (2H, d); 7.99 (1H, s); 10.75 (1H, s).

5-[(1,1'-biphenyl-4-ylsulfonyl)methyl]-5-methylimidazolidine-2,4-dione

LC-MS (APCI) m/z 345 (MH+).
$^1$H NMR (DMSO-d$_6$): δ 1.27 (3H, s); 3.72, 3.81 (2H, abq, J=15.3 Hz); 7.45 (1H, t); 7.52 (2H, t); 7.76 (2H, d); 7.82 (1H, s); 7.88, 7.94 (4H, abq, J=8.9 Hz); 10.80 (1H, bs).

4'-{[(4-methyl-2,5-dioxoimidazolidin-4-yl)methyl]sulfonyl}-1,1'-biphenyl-4-carbonitrile LC-MS (APCI) m/z very weak 370 (MH+).
$^1$H NMR (DMSO-d$_6$): δ 1.26 (3H, s); 3.74, 3.84 (2H, abq, J=16.0 Hz); 7.81 (1H, s); 7.91-8.03 (8H, m); 10.81 (1H, s).

EXAMPLE 12

Synthesis of Enantiomeric Pure Hydantoins

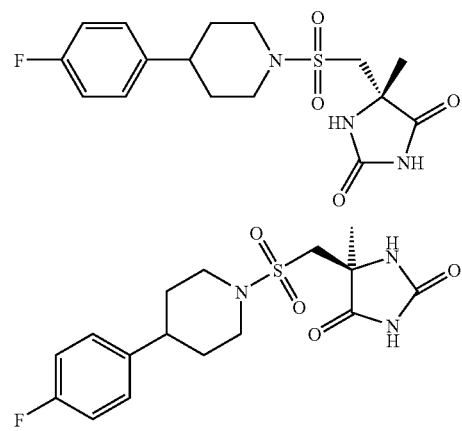

Representative synthetic route is shown overleaf.

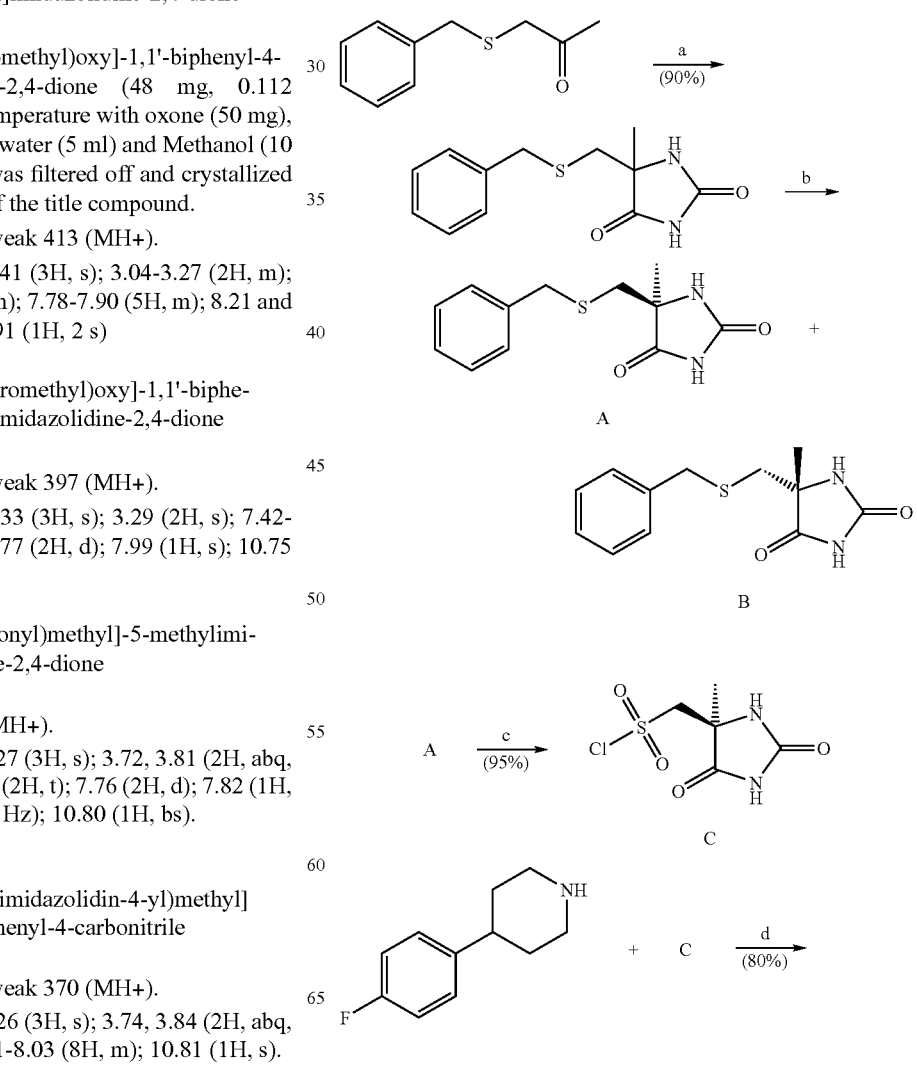

-continued

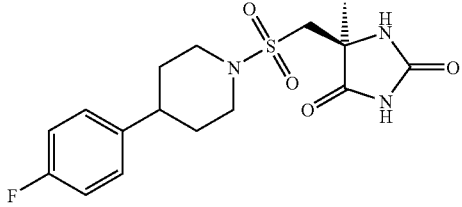

Reagents and conditions:
a) KCN, NH$_4$CO$_3$, EtOH/H$_2$O, +90° C., 3 h.
b) Chiral separation, CHIRALPAK AD, Methanol as eluent.
c) Cl$_2$ (g), AcOH/H$_2$O, < +15° C., 25 min.
d) Diisopropylethylamine, THF. -20° C., 30 min.

EXPERIMENTAL PROCEDURES (5S)-5-({[4-(4-fluorophenyl)piperidin-1-yl]sulfonyl}methyl)-5-methylimidazolidine-2,4-dione 4-(4-Fluorophenyl)piperidine hydrochloride (63 mg, 0.29 mmol) was taken up in 3 mL of dry THF, neutralized with diisopropylethylamine (50 μL, 0.29 mmol) and cooled on an ice-water bath. [(4S)-4-methyl-2,5-dioxo-imidazolodin-4-yl]methanesulfonyl chloride (80 mg, 0.35 mmol) was added and after stirring for 10 min, diisopropylethylamine (50 μL, 0.29 mmol) was added and the reaction mixture was stirred at ambient temperature until LC-MS (APCI) indicated consumption of the amine. The reaction mixture was evaporated and the residue taken up in EtOH and heated to 50° C. and allowed to cool before water was added. The precipitated product was collected and washed with EtOH/water and dried in vacuum to yield 87 mg.

LC-MS (APCI) m/z 370 (MH+).

$^1$H NMR (DMSO-d$_6$): δ 10.73 (1H, s); 8.01 (1H, s); 7.29 (2H, dd); 7.11 (2H, dd); 3.61 (2H, dd); 3.50, 3.33 (1H each, ABq, J=14.7 Hz); 2.91-2.80 (2H, m); 2.67-2.57 (1H, m); 1.82 (2H, d); 1.62 (2H, ddd); 1.33 (3H, s).

The starting materials were prepared as follows:

5-methyl-5-{[(phenylmethyl)thio]methyl}imidazolidine-2,4-dione

A steel vessel was charged with ethanol and water (315 mL/135 mL). 31.7 g (0.175 mol) of benzylthioacetone, 22.9 g (0.351 mol) of potassium cyanide and 84.5 g (0.879 mol) of ammonium carbonate was added. The closed reaction vessel was kept in an is oil bath (bath temperature 90° C.) under vigorous stirring for 3 h.

The reaction vessel was cooled with ice-water (0.5 h), the yellowish slurry was evaporated to dryness and the solid residue partitioned between 400 mL water and 700 mL ethylacetate and separated. The water-phase was extracted with ethylacetate (300 mL). The combined organic phases were washed with saturated brine (150 mL), dried (Na$_2$SO$_4$), filtered and evaporated to dryness. If the product did not crystallize, 300 mL of dichloromethane was added to the oil. Evaporation gave the product as a slightly yellowish powder, 43.8 g (90%).

LC-MS (APCI) m/z 251.1 (MH+).

$^1$H NMR (DMSO-d$_6$) δ: 10.74 (1H, s); 8.00 (1H, s); 7.35-7.20 (5H, m); 3.76 (2H, s); 2.72, 2.62 (1H each, ABq, J=14.0 Hz); 1.29 (3H, s).

$^{13}$C NMR (DMSO-d$_6$) δ: 177.30, 156.38, 138.11, 128.74, 128.24, 126.77, 62.93, 37.96, 36.39, 23.15.

(5S)-5-methyl-5-{[(phenylmethyl)thio]methyl}imidazolidine-2,4-dione

The title compound was prepared by chiral separation of the racemic material using a 250 mm×50 mm column on a Dynamic Axial Compression Preparative HPLC system. The stationary phase used was CHIRALPAK AD, eluent=Methanol, flow=89 mL/min, temp=ambient, UV=220 nm, sample conc=150 mg/mL, injection volume=20 mL.

Retention time for title compound=6 min.

Analysis of chiral purity was made using a 250 mm×4.6 mm CHIRALPAK-AD column from Daicel, flow=0.5 mL/min, eluent=Ethanol, UV=220 nm, temp=ambient.

Retention time for title compound=9.27 min.

Purity estimated to >99% ee.

LC-MS (APCI) m/z 251.1 (MH+).

[α]$_D$=−30.3° (c=0.01 g/mL, MeOH, T=20° C.).

$^1$H NMR (DMSO-d$_6$) δ: 10.74 (1H, s); 8.00 (1H, s); 7.35-7.20 (5H, m); 3.76 (2H, s); 2.72, 2.62 (1H each, ABq, J=14.0 Hz); 1.29 (3H, s).

$^{13}$C NMR (DMSO-d$_6$) δ: 177.30, 156.28, 138.11, 128.74, 128.24, 126.77, 62.93, 37.96, 36.39, 23.15.

(5R)-5-dimethyl-5-{[phenylmethyl)thio]methyl}imidazolidine-2,4-dione

The title compound was prepared by chiral separation of the racemic material using a 250 mm×50 mm column on a Dynamic Axial Compression Preparative HPLC system. The stationary phase used was CHIRALPAK AD, eluent=Methanol, flow-89 mL/min, temp=ambient, UV=220 nm, sample conc=150 mg/mL, injection volume=20 mL.

Retention time for title compound=10 min.

Analysis of chiral purity was made using a 250 mm×4.6 mm CHIRALPAK-AD column from Daicel, flow=0.5 mL/min, eluent=Ethanol, UV=220 nm, temp=ambient.

Retention time for title compound=17.81 min.

Chiral purity estimated to >99% ee.

LC-MS (APCI) m/z 251.0 (MH+).

[α]$_D$=+30.3° (c=0.01 g/mL, MeOH, T=20° C.).

$^1$H NMR (DMSO-d$_6$) δ: 10.74 (1H, s); 8.00 (1H, s); 7.35-7.20 (5H, m); 3.76 (2H, s); 2.72, 2.62 (1H each, ABq, J=14.0 Hz); 1.29 (3H, s).

$^{13}$C NMR (DMSO-d$_6$) δ: 177.31, 156.30, 138.11, 128.74, 128.25, 126.77, 62.94, 37.97, 36.40, 23.16.

[(4S)-4-methyl-2,5-dioxoimidazolidin-4-yl]methanesulfonyl chloride (5S)-5-methyl-5-{[(phenylmethyl)thio]methyl}imidazolidine-2,4-dione (42.6 g; 0.17 mol) was dissolved in a mixture of AcOH (450 mL) and H$_2$O (50 mL). The mixture was immersed in an ice/water bath, Cl$_2$ (g) was bubbled through the solution, the flow of gas was adjusted so that the temperature was kept below +15° C. After 25 min the solution became yellow-green in colour and a sample was withdrawn for LC/MS and HPLC analysis. It showed that starting material was consumed. The yellow clear solution was stirred for 30 min and an opaque solution/slurry was formed.

The solvent was removed on a rotary evaporator using waterbath with temperature held at +37° C. The yellowish solid was suspended in Toluene (400 mL) and solvent removed on the same rotary evaporator. This was repeated once more.

The crude product was then suspended in iso-Hexane (400 mL) and warmed to +40° C. while stirring, the slurry was allowed to cool to room temperature before the insoluble product was removed by filtration, washed with iso-Hexane (6×100 mL), and dried under reduced pressure at +50° C. over night. This gave the product as a slightly yellow powder.

Obtained 36.9 g (95%) of the title compound.
Purity by HPLC=99%, NMR supported that purity.
$[\alpha]_D$=−12.4° (c=0.01 g/mL, THF, T=20° C.).
$^1$H NMR (THF-$d_8$): δ 9.91 (1H, bs); 7.57 (1H, s); 4.53, 4.44 (1H each, ABq, J=14.6 Hz); 1.52 (s, 3H, CH$_3$).
$^{13}$C NMR (THF-$d_8$): δ 174.96; 155.86; 70.96; 61.04; 23.66.

[(4R)-4-methyl-2,5-dioxoimidazolidin-4-yl]methanesulfonyl chloride

Following the procedure described for [(4S)-4-methyl-2,5-dioxoimidazolidin-4-yl]methanesulfonyl chloride.
Starting from (5R)-5-methyl-5-{[(phenylmethyl)thio]methyl}imidazolidine-2,4-dione (10.0 g, 40 mmol).
Obtained 8.78 g (96% yield) of the title compound.

Purity by NMR>98%.
$[\alpha]_D$=+12.80 (c=0.01 g/mL, THF, T=20° C.).
$^1$H NMR (THF-$d_8$): δ 9.91 (1H, brs); 7.57 (1H, s); 4.53, 4.44 (1H each, ABq, J=14.6 Hz); 1.52 (s, 3H, CH$_3$).
$^{13}$C NMR (THF-$d_8$): δ 174.96; 155.84; 70.97; 61.04; 23.66.

EXAMPLE 13

Compounds with the General Formula

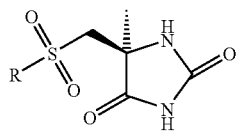

were synthesised according to the method described in Example 12.

| AMINE INTERMEDIATES | |
|---|---|
| Amine | Analysis |
| [structure: 4-(trifluoromethoxy)phenyl-piperidine] | m/z 246 (MH+); $^1$H NMR data |
| [structure: pyridin-2-yl-ethynyl-tetrahydropyridine] | m/z 185 (MH+); $^1$H NMR data |
| [structure: 4-methylphenyl-ethynyl-tetrahydropyridine] | m/z 198 (MH+); $^1$H NMR data |
| [structure: 4-chlorophenyl-ethynyl-tetrahydropyridine] | m/z 218/220 3:1 (MH+); $^1$H NMR data |
| [structure: 5-(trifluoromethyl)pyridin-2-yl-oxy-piperidine] | m/z 247 (MH+); $^1$H NMR data |
| [structure: 5-cyanopyridin-2-yl-oxy-piperidine] | m/z 204 (MH+); $^1$H NMR data |
| [structure: 5-methylpyridin-2-yl-oxy-piperidine] | $^1$H NMR data |

-continued
| AMINE INTERMEDIATES | |
|---|---|
| Amine | Analysis |
| 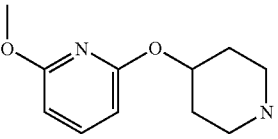 | ¹H NMR data |
| 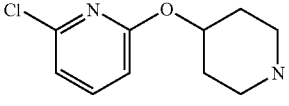 | ¹H NMR data |
| 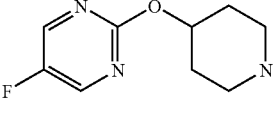 | ¹H NMR data |
| 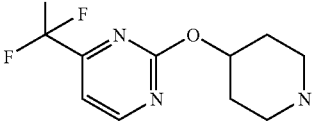 | ¹H NMR data |
| 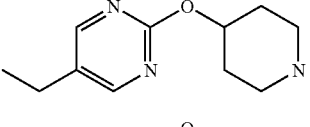 | ¹H NMR data |
| 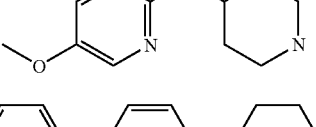 | m/z 225 (MH+) |
| 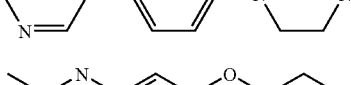 | m/z 240 (MH+) |
| 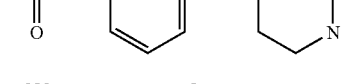 | m/z 235 (MH+) |
| 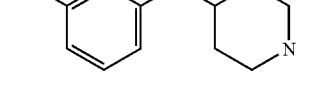 | m/z 203 (MH+) |
| 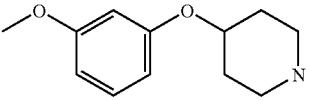 | m/z 208 (MH+) |
| 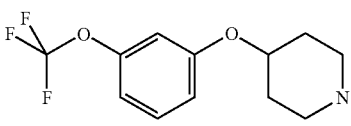 | m/z 262 (MH+) |
| 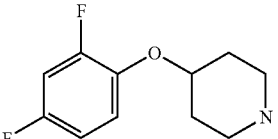 | m/z 214 (MH+) |

-continued
AMINE INTERMEDIATES
| Amine | Analysis |
|---|---|
| 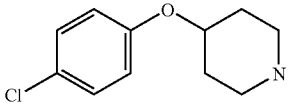 | m/z 212 (MH+) |
| 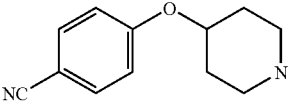 | m/z 203 (MH+) |
| 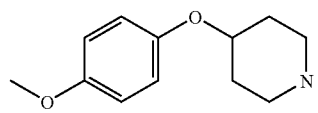 | m/z 208 (MH+) |
| 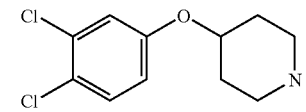 | m/z 246 (MH+) |
| 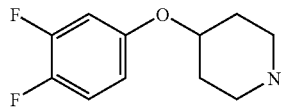 | m/z 214 (MH+) |
| 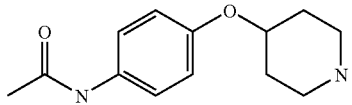 | m/z 235 (MH+) |
| 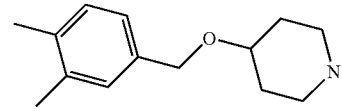 | m/z 220 (MH+) |
| 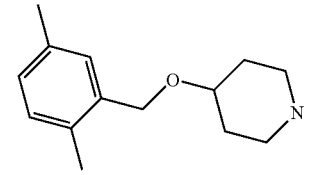 | m/z 220 (MH+) |
| 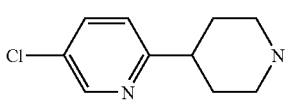 | m/z 197 (MH+); $^1$H NMR data |
| 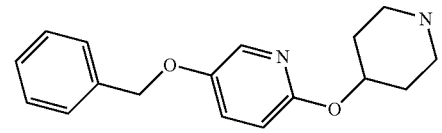 | m/z 285 (MH+) |
| 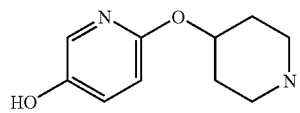 | m/z 195 (MH+); $^1$H NMR data |

-continued

| AMINE INTERMEDIATES | |
|---|---|
| Amine | Analysis |
| 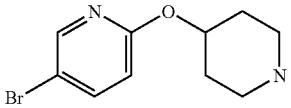 | m/z 257, 259 (MH+) |
| 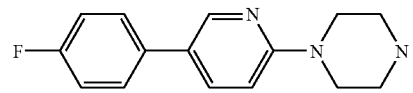 | m/z 258 (MH+) |
| 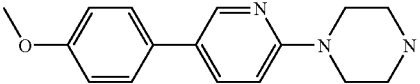 | m/z 270 (MH+) |
| 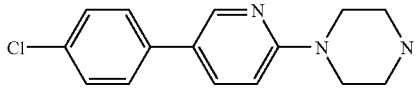 | m/z 274, 276 (MH+) |
| 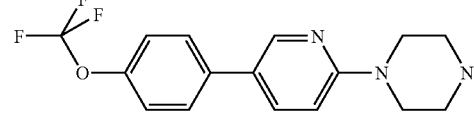 | m/z 324 (MH+) |
|  | m/z 230 (MH+) |
| 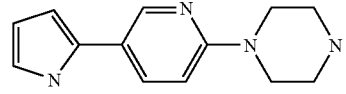 | m/z 229 (MH+) |
| 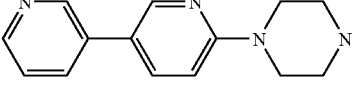 | m/z 241 (MH+) |
| 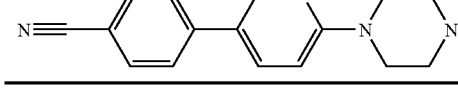 | m/z 265 (MH+) |

All other amines used are commercially available or earlier described.

4-{([(trifluoromethyl)oxy]phenyl}piperidine trifluoroacetic acid

Pd(PPh$_3$)$_4$ (87 mg, 0.0075 mmol), LiCl (190 mg, 4.5 mmol), tert-butyl 4-{[(trifluoromethyl)sulfonyl]oxy}-3,6-dihydropyridine-1(2H)-carboxylate (0.50 g 1.5 mmol), 4-(trifluoromethoxy)phenylboronic acid (0.43 g, 2.1 mmol) and aq Na$_2$CO$_3$ (2 mL, 2N solution) were mixed in 5.2 mL DME and heated at 85° C. for 3 h followed by cooling to room temperature and concentrated under reduced pressure. The residue was partitioned between DCM (10 mL), aq Na$_2$CO$_3$ (10 mL, 2N solution) and conc NH$_4$OH (0.6 mL). The layers were separated and the aqueous layer extracted with DCM (3×10 mL). The combined organic layers were dried (Na$_2$SO$_4$) and concentrated. Purification by column chromatography (SiO$_2$, Heptane/Ethylacetate/DCM 5:1:1) gave tert-butyl 4-[4-(trifluoromethoxy)phenyl]-3,6-dihydropyridine-1(2H)-carboxylate (0.27 g, 52%). The product and 5% Pd/C (30 mg) was mixed in MeOH (3 mL) and stirred under H$_2$ (1 atm) for 24 h. The mixture was filtered through Celite and concentrated to give tert-butyl 4-[4-(trifluoromethoxy)phenyl]piperidine-1-carboxylate-(0.23 g, 86%). The crude product was dissolved in a mixture of TFA (2 mL) and DCM (4 mL) and stirred at RT for 2 h. The reaction mixture was concentrated and purified by preparative HPLC to give the title compound (0.14 g, 58%, three steps 26%).

LC-MS (APCI) m/z 246 (MH+).

$^1$H NMR (CDCl$_3$): δ 9.38 (1H, bs); 8.97 (1H, bs); 7.26 (2H, d); 7.20 (2H, d); 3.60 (2H, bd); 3.07 (2H, q); 2.88-2.72 (1H, m); 2.18-2.01 (4H, m).

$^{19}$F NMR (CDCl$_3$): δ −58.35 (3F), −76.19 (3F).

4-[(4-chlorophenyl)ethynyl]-1,2,3,6-tetrahydropyridine hydrochloride

PdCl$_2$(PPh$_3$)$_2$ (47 mg, 0.07 mmol) and CuI (13 mg, 0.07 mmol) were dissolved in Et$_3$N (2.7 mL) and THF (8.4 mL)

under a stream of argon and stirred for 10 min. A solution of tert-butyl 4-{[(trifluoromethyl)sulfonyl]oxy}-3,6-dihydropyridine-1(2H)carboxylate (0.46 g 1.4 mmol) and 2-ethynylpyridine (152 µL, 1.5 mmol) in 3.5 mL THF was added. The reaction mixture was stirred at RT for 2 h, diethyl ether was added and the precipitate was filtered off. The clear solution was washed with saturated aqueous $NH_4Cl$, water, Brine and dried ($Na_2SO_4$). Concentration and purification by column chromatography ($SiO_2$, Heptane/Diethyl ether 1:2) gave tert-butyl 4-[(4-chlorophenyl)ethynyl]-3,6-dihydropyridine-1(2H)-carboxylate (0.26 g, 58%). The product was dissolved in THF (3 mL) and conc HCl (3 mL) and stirred at RT for 30 min. Concentration several times with toluene and EtOH gave the title compound (0.20 g, 98%, two steps 57%).

LC-MS (APCI) m/z 218/220 3:1 (MH+).

$^1$H NMR (DMSO-$d_6$): δ 9.25 (2H, bs); 7.49-7.44 (4H, m); 6.24-6.11 (1H, m); 3.75-3.63 (2H, m); 3.25-3.15 (2H, m); 2.48-2.42 (2H, m).

The following amines were prepared in a similar way as described for 4-[(4-chlorophenyl)ethynyl]-1,2,3,6-tetrahydropyridine hydrochloride.

2-(1,2,3,6-tetrahydropyridine-4-ylethynyl)pyridine

LC-MS (APCI) m/z 185 (MH+).

$^1$H NMR (CDCl$_3$): δ 8.59-8.55 (1H, m); 7.64 (1H, dt); 7.43-7.39 (1H, m); 7.20 (1H, ddd); 6.30 (1H, bs); 3.51 (2H, q); 3.04 (2H, t); 2.37-2.31 (2H, m).

4-[(4-methylphenyl)ethynyl]-1,2,3,6-tetrahydropyridine

LC-MS (APCI) m/z 198 (MH+).

$^1$H NMR (CDCl$_3$): δ 8.91 (1H, bs); 7.33 (2H, d); 7.15 (2H, d); 6.06 (1H, bs); 3.93-3.80 (2H, m); 3.49-3.335 (2H, m); 2.73-2.60 (2H, m); 2.37 (3H, s).

2-(Piperidin-4-yloxy)-5-trifluoromethyl-pyridine

Sodium hydride (0.52 g, 12 mmol, 55% in oil) was washed twice in hexane, and suspended in dry dimethoxyethane (30 ml). 4-hydroxypiperidine (1.21 g, 12 mmol) and 2-chloro-5-trifluoromethylpyridine was dissolved in dry dimethoxyethane (30 ml). The solution was added dropwise to the sodium hydride-suspension. The reaction was stirred at 80° C. under nitrogen over night. After cooling. Water was carefully added to the mixture and the solvents were removed by rotary evaporation. The residue was dissolved in water and extracted with ethyl acetate. The organic phase was dried over $Na_2SO_4$ and evaporated. The residue was chromatographed on silica gel eluting with 80:20:2 EtOAc/MeOH/Et$_3$N affording 1.7 g (63%) of the title compound as a yellow oil, which crystallised after a few hours.

LC-MS (APCI) m/z 247.1 (MH+).

$^1$H NMR (CDCl$_3$): δ 8.40 (1H, s); 7.74 (1H, dd, J=2.52, 8.70 Hz); 6.78 (1H, d, J=8.74 Hz); 5.25-5.17 (1H, m); 3.19-3.08 (2H, m); 2.83-2.73 (2H, m); 2.10-2.00 (2H, m); 1.83 (1H, s); 1.73-1.62 (2H, m).

The following amines were prepared in a similar way as described in the synthesis of 2-(Piperidin-4-yloxy)-5-trifluoromethyl-pyridine.

6-(Piperidin-4-yloxy)-nicotinonitrile

LC-MS (APCI) m/z 204.2 (MH+).

$^1$H NMR (CDCl$_3$): δ 8.45 (1H, s); 7.76 (1H, dd, J=2.40, 8.77 Hz); 6.78 (1H, d, J=8.77 Hz); 5.28-5.17 (1H, m); 3.19-3.09 (2H, m); 2.83-2.74 (2H, m); 2.10-2.01 (2H, m); 1.74-1.63 (2H, m).

5-Methyl-2-(piperidin-4-yloxy)-pyridine

1H NMR (Methanol-$d_4$): δ 7.90 (1H, s); 7.46 (1H, dd, J=2.47, 8.46 Hz); 6.68 (1H, d, J=8.50 Hz); 5.07-4.98 (1H, m); 3.15-3.07 (2H, m); 2.82-2.73 (2H, m); 2.23 (3H, s); 2.07-1.97 (2H, m); 1.84-1.74 (2H, m).

2-Methoxy-6-(piperidin-4-yloxy)-pyridine $^1$H NMR (CDCl$_3$): δ 7.44 (1H, t, J=7.90 Hz); 7.25 (2H, dd, J=1.83, 7.90 Hz); 5.19-5.11 (1H, m); 3.82 (3H, s); 3.23-3.16 (2H, m); 2.96-2.88 (2H, m); 2.13-2.05 (2H, m); 1.89-1.79 (2H, m).

2-chloro-6-(piperidine-yl-oxy)-pyridine $^1$H NMR (Methanol-$d_4$): δ 7.64 (1H, dd, J=7.60, 8.22 Hz); 6.96 (1H, dd, J=0.66, 7.60 Hz); 6.73 (1H, dd, J=0.60, 8.19 Hz); 5.25-5.14 (1H, m); 3.28-3.18 (2H, m); 3.05-2.94 (2H, m); 2.19-2.07 (2H, m); 1.93-1.80 (2H, m).

5-Fluoro-2-(piperidin-4-yloxy)-pyrimidine $^1$H NMR (CDCl$_3$): δ 8.36 (2H, s); 5.16-5.06 (1H, m); 3.29-3.18 (2H, m); 2.98-2.87 (2H, m); 2.21-2.08 (2H, m); 1.97-1.81 (2H, m).

2-Piperidin-4-yloxy)-4-trifluoromethyl-pyrimidine $^1$H NMR (CDCl$_3$): δ 8.75 (1H, d, J=4.93 Hz); 7.27 (1H, d, J=5.07 Hz); 5.39-5.30 (1H, m); 3.44-3.33 (2H, m); 3.28-3.17 (2H, m); 2.35-2.10 (4H, m).

5-Ethyl-2-(piperidin-4-yloxy)-pyrimidine $^1$H NMR (Methanol-$d_4$): δ 8.40 (2H, s); 5.16-5.08 (1H, m); 3.16-3.06 (2H, m); 2.77-2.70 (2H, m); 2.60 (2H, q, J=7.66, 15.28 Hz); 2.10-2.00 (2H, m); 1.76-1.66 (2H, m); 1.23 (3H, t, J=7.63 Hz).

5-Methoxy-2-(piperidin-4-yloxy)-pyridine; hydrochloride 4-(5-Methoxy-pyridin-2-yloxy)-piperidine-1-carboxylic acid tert-butyl ester (45 mg, 0.14 mmol) was dissolved in THF (3 ml) and conc. HCl (2 ml) was added. The reaction was stirred at room temperature for 2 hrs after which the solvents were removed in vacuo and the remaining water was removed by azeotropic evaporation using EtOH/Toluene affording 35 mg (97%) of the title compound as oily crystals.

LC-MS (APCI) m/z 225.1 (MH+).

The starting material was prepared as follows:

2-Chloro-5-methoxy-pyridine 1-oxide 2-chloro-5-methoxy-pyridine (200 mg, 1.39 mmol) and mCPBA (360 mg, 2.09 mmol) was dissolved in $CH_2Cl_2$ (10 ml). The mixture was stirred at room temperature for 2 days. The mixture was then diluted with $CH_2Cl_2$ and washed with 10% aqueous K$_2$CO$_3$ and brine and dried over Na$_2$SO$_4$. The solvent were removed in vacuo affording 140 mg (63%) of the title compound as white crystals.

$^1$H NMR (DMSO-d$_6$): δ 8.30 (1H, d, J=2.72 Hz); 7.68 (1H, d, J=9.23 Hz); 7.08 (1H, dd, J=2.70, 9.23 Hz); 3.31 (3H, s).

4-(5-Methoxy-1-oxy-pyridin-2-yloxy)-piperidine-1-carboxylic acid tert-butyl ester Potassium tert-butoxide (128 mg, 1.14 mmol) was dissolved in dry THF (10 ml) and 4-Hydroxy-piperidine-1-carboxylic acid tert-butyl ester (177 mg, 0.88 mmol) dissolved in 0 dry THF (5 ml) was added under nitrogen. The mixture was stirred at room temperature for 10 minutes after which 2-Chloro-5-methoxy-pyridine 1-oxide (140 mg, 0.88 mmol) dissolved in dry THF (5 ml) was added. The reaction was stirred for 3 days at room temperature. The solvent were removed and the residue was partitioned between H$_2$O and CHCl$_3$. The organic phase was washed with brine and dried over Na$_2$SO$_4$. The solvent were removed in vacuo affording 245 mg (86%) of the title compound as a brown oil.

$^1$H NMR (CDCl$_3$): δ 7.95-7.93 (1H, m); 6.86-6.84 (2H, m); 4.95-4.85 (1H, m); 3.79 (3H, s); 3.25-3.14 (2H, m); 3.07-2.96 (2H, m); 1.98-1.79 (4H, m); 1.46 (9H, s).

4-(5-Methoxy-pyridin-2-yloxy)-piperidine-1-carboxylic acid tert-butyl ester 4-(5-Methoxy-1-oxy-pyridin-2-yloxy)-piperidine-1-carboxylic acid tert-butyl ester (200 mg, 0.62 mmol) was dissolved in EtOH (5 ml). Indium (498 mg, 4.34 mmol) and saturated aqueous NH$_4$Cl (4 ml) was added to the solution and the reaction was refluxed for 4 days. The mixture was filtered through celite after cooling and the solvents were removed in vacuo. The residue was chromatographed on silica gel eluting with 5:1 Heptane/EtOAc affording 50 mg (26%) of the title compound as a yellowish oil.

$^1$H NMR (CDCl$_3$): δ 7.77 (1H, d, J=3.06 Hz); 7.20 (1H, dd, J=−3.07, 8.89 Hz); 6.66 (1H, d, J=8.99 Hz); 5.14-5.07 (1H, m); 3.80 (3H, s); 3.79-3.72 (2H, m); 3.31-3.23 (2H, m); 2.00-1.91 (2H, m); 1.75-1.64 (2H, m); 1.47 (9H, s).

4-(4-Pyridin-3-yl-phenyl)piperazine; hydrochloride 4-(4-Pyridin-3-yl-phenyl)piperazine-1-carboxylic acid tert-butyl ester (60 mg, 0.18 mmol) in THF (3 ml) and conc. HCl (3 ml) was stirred for 1 hr. The solvents were removed in vacuo and the remaining water was removed by azeotropic evaporation using EtOH/Toluene, affording 50 mg (100%) of the title compound as a yellow powder.

LC-MS (APCI) m/z 240.2 (MH+).

The starting material was prepared as follows:

4-(4-Iodophenyl)piperazine-1-carboxylic acid tert-butyl ester was prepared according to La Clair in *Angew. Chem. Int. Ed.* 1998, 37(3), 325-329 in 55% overall yield starting from N-phenylpiperazine (19 mmol).

4-(4-Pyridin-3-yl-phenyl)piperazine-1-carboxylic acid tert-butyl ester (Ref Wellmar et al. *J. Heterocycl. Chem.* 32(4), 1995, 1159-1164.)

4-(4-Iodophenyl)piperazine-1-carboxylic acid tert-butyl ester (0.272 g, 0.70 mmoles), 3-pyridylboronic acid (0.078 g, 0.64 mmoles), tetrakis(triphenylphosphine)palladium (0.024 g, 0.02 mmoles), 1 M sodium hydrogencarbonate (1.0 mL) and 1,2-dimethoxyethane (1.5 mL) were stirred under nitrogen at 84° C. for 3 hours, taken up in ethyl acetate and washed with water and brine. The organic phase was dried over anhydrous sodium sulfate, filtered, concentrated with silica (1 g) by rotary evaporation to give a solid which was applied on a short silica column. Elution with dichloromethane, dichloromethane/ethyl acetate (4:1) and neat ethyl acetate gave 0.060 g (32% yield) of the title compound as a white solid and 0.060 g of starting material (the iodide), respectively. Yield was calculated from amount of converted iodide.

LC-MS (APCI) m/z 340.3 (MH+).

$^1$H NMR (Methanol-d$_4$): δ 8.75 (1H, d, J=2.0 Hz); 8.43 (1H, m); 8.04 (1H, m); 7.58 (2H, d, J=8.0 Hz); 7.47 (1H, m); 7.10 (2H, d, J=8.0 Hz); 3.59 (4H, m); 3.22 (4H, m); 1.50 (9H, s).

N-[3-Piperidin-4-yloxy)-phenyl]-acetamide; hydrochloride

4-Hydroxy-piperidine-1-carboxylic acid tert-butyl ester (300 mg, 1.5 mmol) was dissolved in dry CH$_2$Cl$_2$ and cooled to −10° C. Polymer bound triphenylphosphine (750 mg, 2.25 mmol) was added and allowed to swell. N-3-Hydroxy-phenyl)-acetamide (340 mg, 2.25 mmol) dissolved in dry THF was added and the reaction was stirred at −10° C. for 10 minutes after which DEAD (0.35 ml, 2.25 mmol) was added dropwise to the mixture. The reaction was stirred over night allowing the temperature rise to room temperature. The polymer was filtered off, using a short plug of silica with Toluene/EtOAc (5:1) as eluent. The volume of the combined fractions was reduced by rotary evaporation and the solution was washed with 5% aqueous KOH and water, dried over Na$_2$SO$_4$ and the solvent removed in vacuo. The resulting white powder was dissolved in THF (10 ml) and conc. HCl (10 ml) and stirred at ambient temperature for 1 hr. The solvents were removed in vacuo and the remaining water was removed by azeotropic evaporation using EtOH/Toluene, affording 230 mg (57%) of the title compound as a white powder.

LC-MS (APCI) m/z 235.1 (MH+).

The following amines were prepared in a similar way as described in the synthesis N-[3-(Piperidin-4-yloxy)-phenyl]-acetamide.

3-(Piperidin-4-yloxy)benzonitrile

LC-MS (APCI) m/z 203.2 (MH+).

4-(3-Methoxy-phenoxy)-piperidine

LC-MS (APCI) m/z 208.2 (MH+).

4-(3-Trifluoromethoxy-phenoxy)piperidine

LC-MS (APCI) m/z 262.1 (MH+).

4-(2,4-Difluoro-phenoxy)-piperidine

LC-MS (APCI) m/z 214.2 (MH+).

4-(4-chloro-phenoxy)-piperidine

LC-MS (APCI) m/z 212.2 (MH+).

4-(Piperidin-4-yloxy)-benzonitrile

LC-MS (APCI) m/z 203.2 (MH+).

4-(4-Methoxy-phenoxy)-piperidine

LC-MS (APCI) m/z 208.2 (MH+).

4-(3,4-Dichloro-phenoxy)-piperidine

LC-MS (APCI) m/z 246.1 (MH+).

4-(3,4-Difluoro-phenoxy)-piperidine

LC-MS (APCI) m/z 214.2 (MH+).

N-[4-(Piperidin-4-yloxy)-phenyl]-acetamide

LC-MS (APCI) m/z 235.1 (MH+).

4-{[(3,4-dimethylphenyl)methyl]oxy}piperidine hydrochloride

LC-MS (APCI) m/z 220 (MH+).

4-{[(2,5-dimethylphenyl)methyl]oxy}piperidine hydrochloride

LC-MS (APCI) m/z 220 (MH+).

5-chloro-2-piperidin-4-ylpyridine hydrochloride

Zn dust (225 mg, 3.5 mmol) was stirred in THF (1 mL) under Ar and 1,2-dibromoethane (50 μL) was added at room temperature. The mixture was heated to 65° C. for 3 min and allowed to cool to room temperature before trimethylsilyl chloride (70 μL) was added and the mixture was stirred at room temperature for 30 min. A solution of 4-iodo-N-Boc-piperidine (840 mg, 2.7 mmol) in THF (1.5 mL) was slowly added and the reaction mixture was stirred at 40° C. for 2 h. $Pd_2(dba)_3$ (22 mg, 0.024 mmol) and $P(2-furyl)_3$ (23 mg, 0.10 mmol) were mixed in THF (0.5 mL), the mixture stirred at room temperature for 10 min and then added to the organozinc reagent solution, followed by 2-bromo-5-chloro-pyridine (624 mg, 3.24 mmol) in THF (1 mL) and DMA (4 mL). The reaction mixture was heated at 80° C. for 3 h, allowed to cool to room temperature and then filtered through Celite and diluted with EtOAc. The filtrate was washed with saturated aqueous $NaHCO_3$ and brine, dried $Na_2SO_4$ and concentrated. Purification on $SiO_2$ eluting with heptane/EtOAc 95:5 to 2:1 gave tert-butyl 4-(5-chloropyridin-2-yl)piperidine-1-carboxylate as an yellow oil (128 mg, 16%). The oil was dissolved in THF (1.5 mL) and conc HCl (1.5 mL) and stirred at RT for 30 min. Concentration several times with toluene and EtOH gave the title compound (89 mg, 89%)

LC-MS (APCI) m/z 197 (MH+).
$^1$H NMR (MeOD-$d_4$): δ 8.54 (1H, d); 7.86 (1H, dd); 7.38 (1H, d); 3.55-345 (2H, m); 3.22-3.06 (3H, m); 2.19-2.09 (2H, m); 2.08-1.98 (2H, m).

5-Benzyloxy-2-(piperidin-4-yloxy)-pyridine; hydrochloride

The amine was prepared in the same way as described in the synthesis of 5-Methoxy-2-(piperidin-4-yloxy)-pyridine.
LC-MS (APCI) m/z 285 (MH+).
The starting material was prepared as follows:

2-Chloro-5-benzyloxypyridine

Sodium hydride (55% in oil, 236 mg, 5.40 mmol) washed in Hexane and 2-Chloro-5-hydroxypyridine (350 mg, 2.70 mmol) was suspended in dry DMF (20 ml). After 10 minutes at room temperature Benzylbromide (0.32 ml, 2.70 mmol) was added and the mixture was stirred for an additional 2 hrs. The reaction was diluted with water and extracted with EtOAc (3*50 ml). The combined organic layers were washed with water and brine, and dried over $Na_2SO_4$. The solvent was removed by rotary evaporation, affording 520 mg (88%) of the title compound as a yellow oil.

LC-MS (APCI) m/z 220 (MH+).
$^1$H NMR (CDCl$_3$): δ 8.19 (1H, d, J=3.00 Hz); 7.55 (1H, dd, J=3.15, 8.81 Hz); 7.48-7.31 (6H, m); 5.19 (2H, s).

2-Chloro-5-benzyloxy-pyridine 1-oxide

The amine was prepared in the same way as described in the synthesis of 2-Chloro-5-methoxy-pyridine 1-oxide.
LC-MS (APCI) m/z 236 (MH+).
$^1$H NMR (DMSO-$d_6$): δ 8.38 (1H, d, J=2.61 Hz); 7.69 (1H, d, J=9.28 Hz); 7.47-7.33 (5H, m); 7.15 (1H, dd, J=2.69, 9.15 Hz); 5.19 (2H, s).

4-(5-Benzyloxy-1-oxy-pyridin-2-yloxy)-piperidine-1-carboxylic acid tert-butyl ester The compound was prepared as described in the synthesis of 4-(5-Methoxy-1-oxy-pyridin-2-yloxy)-piperidine-1-carboxylic acid tert-butyl ester.
LC-MS (APCI) m/z 401 (MH+).
$^1$H NMR (DMSO-$d_6$): δ 8.12 (1H, d, J=2.79 Hz); 7.48-7.32 (5H, m); 7.19 (1H, d, J=9.16 Hz); 7.07 (1H, dd, J=2.88, 9.18 Hz); 5.13 (2H, s); 4.84-4.76 (1H, m); 3.20-3.11 (2H, m); 3.00-2.87 (2H, m); 1.86-1.78 (2H, m); 1.59-1.49 (2H, m); 1.40 (9H, s).

4-(5-Benzyloxy-pyridin-2-yloxy)-piperidine-1-carboxylic acid tert-butyl ester The compound was prepared as described in the synthesis of 4-(5-Methoxy-pyridin-2-yloxy)-piperidine-1-carboxylic acid tert-butyl ester.
LC-MS (APCI) m/z 385 (MH+).
$^1$H NMR (CDCl$_3$): δ 7.86 (1H, d, J=3.10 Hz); 7.46-7.32 (5H, m); 7.28 (1H, dd, J=3.16, 9.04 Hz); 6.67 (1H, d, J=9.04 Hz); 5.16-5.08 (1H, m); 5.05 (2H, s); 3.84-3.72 (2H, m); 3.33-3.25 (2H, m); 2.02-1.93 (2H, m); 1.76-1.66 (2H, m); 1.49 (9H, s).

5-Hydroxy-2-(piperidin-4-yloxy)-pyridine trifluoroacetic acid 4-(5-Benzyloxy-1-oxy-pyridin-2-yloxy)-piperidine-1-carboxylic acid tert-butyl ester (476 mg, 1.19 mmol) was dissolved in Methanol (20 ml) and Pd(OH)$_2$ (30 mg) was added. The mixture was hydrogenated at 1 atm and room temperature for 24 hrs. The catalyst was filtered off, and the mixture was purified using preparative HPLC affording, after freeze drying, 110 mg (30%) of the title compound as a TFA-salt and 34 mg (10%) of the neutral Boc-protected intermediate.

LC-MS (APCI) m/z 195 (MH+).
$^1$H NMR (DMSO-$d_6$): δ 7.66 (1H, d, J=2.94 Hz); 7.20 (1H, dd, J=3.07, 8.82 Hz); 6.68 (1H, d, J=8.93 Hz); 5.12-5.00 (1H, m); 3.29-3.00 (4H, m); 2.16-2.02 (2H, m); 1.93-1.75 (2H, m).

5-Bromo-2-(piperidin-4-yloxy)-pyridine hydrochloride

The amine was prepared in the same way as described in the synthesis of 5-Methoxy-2-(piperidin-4-yloxy)-pyridine.

LC-MS (APCI) m/z 257+259 (MH+)

The starting material was prepared as described in the synthesis of 4-(5-Methoxy-pyridin-2-yloxy)-piperidine-1-carboxylic acid tert-butyl ester:

4-(5-Bromo-pyridin-2-yloxy)-piperidine-1-carboxylic acid tert-butyl ester

LC-MS (APCI) m/z 357+359 (MH+).

$^1$H NMR (DMSO-d$_6$): δ 8.26 (1H, dd, J=0.53, 2.67 Hz); 7.88 (1H, dd, J=2.66, 8.81 Hz); 6.80 (1H, dd, J=0.53, 8.79 Hz); 5.15-5.07 (1H, m); 3.72-3.64 (2H, m); 3.20-3.09 (2H, m); 1.97-1.88 (2H, m); 1.58-1.48 (2H, m); 1.40 (9H, s).

4-(5-(4-Fluoro-phenyl)-pyridine-2-yl)-piperazine hydrochloride 4-(5-(4-Fluoro-phenyl)-pyridine-2-yl)-piperazine-1-carbaldehyde (98 mg, 0.34 mmol) was dissolved in MeOH (5 ml) and conc. HCl (12M, 5 ml) was added. The mixture was stirred at room temperature over night. The solvents were removed in vacuo and the remaining water was removed by azeotropic evaporation using EtOH/Toluene affording 102 mg (100%) of the title compound as a yellow powder.

LC-MS (APCI) m/z 258 (MH+).

The starting material was prepared as follows:

4-(5-(4-Fluoro-phenyl)-pyridine-2-yl)-piperazine-1-carbaldehyde 4-(5-Bromo-pyridine-2-yl)-piperazine-1-carbaldehyde (100 mg, 0.37 mmol), 4-Fluorobenzeneboronic acid (55 mg, 0.39 mmol), (1,1'-bis(diphenylphosphino)ferrocene)-dichloropalladium(II) (10 mg, 0.01 mmol), Toluene (2 ml), EtOH (0.5 ml) and 2M Na$_2$CO$_3$ solution (0.5 ml, 1 mmol) were heated at 80° C. under N$_2$ overnight. After cooling the mixture was diluted with toluene and separated. The organic phase was washed with water and brine, filtered through a pad of celite and dried over Na$_2$SO$_4$. The solvent were removed in vacuo affording 100 mg (94%) of the title product as a beige powder.

LC-MS (APCI) m/z 286 (MH+).

$^1$H NMR (DMSO-d$_6$): δ 8.44 (1H, d, J=2.66 Hz); 8.10 (1H, s); 7.97 (1H, dd, J=2.52, 8.82 Hz); 7.70-7.31 (2H, m); 7.31-7.21 (2H, m); 6.97 (1H, d, J=8.97 Hz); 3.65-3.43 (8H, m).

The following compounds were synthesised as described in the synthesis of 4-(5-(4-Fluoro-phenyl)-pyridine-2-yl)-piperazine hydrochloride:

4-(5-(4-Methoxy-phenyl)-pyridine-2-yl)-piperazine hydrochloride

LC-MS (APCI) m/z 270 (MH+).

4-(5-(4-Chloro-phenyl)-pyridine-2-yl)-piperazine hydrochloride

LC-MS (APCI) m/z 274, 276 (MH+).

4-(5-(4-Trifluoromethoxy-phenyl)-pyridine-2-yl) piperazine hydrochloride

LC-MS (APCI) m/z 324 (MH+).

4-(5-Furan-2-yl-pyridine-2-yl)-piperazine hydrochloride

LC-MS (APCI) m/z 230 (MH+).

4-(5-(1H-Pyrrol-2-yl)-pyridine-2-yl)-piperazine dihydrochloride

The title compound was prepared from 2-(6-(4-Formyl-piperazine-1-yl)-pyridine-3-yl)-pyrrole-1-carboxylic acid tert-butyl ester.

LC-MS (APCI) m/z 229 (MH+).

4-[3,3']-Bipyridinyl-6-yl-piperazine hydrochloride

LC-MS (APCI) m/z 241 (MH+).

4-(6-piperazine-1-yl-pyridine-3-yl)benzonitrile hydrochloride

LC-MS (APCI) m/z 265 (MH+).

| HYDANTOINS OF FORMULA I | |
|---|---|
| Hydantoin | Analysis[1] |
| 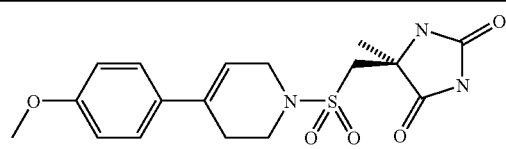 | m/z 380 (MH+) |
| 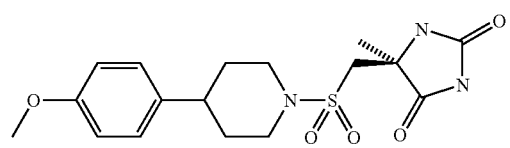 | m/z 382 (MH+) |
| 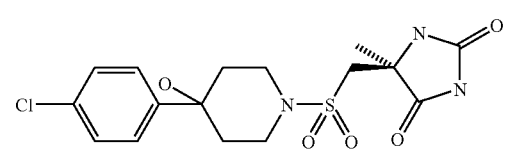 | m/z 402/403 3:1 (MH+) |

-continued
HYDANTOINS OF FORMULA I
| Hydantoin | Analysis[1] |
|---|---|
| 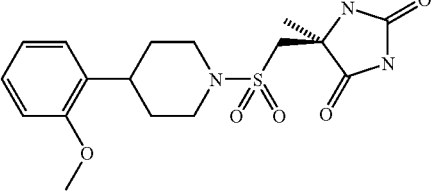 | m/z 382 (MH+) |
| 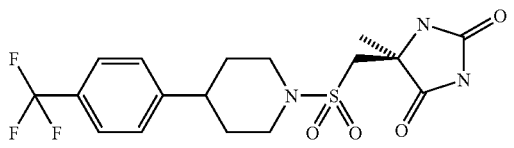 | m/z 420 (MH+) |
| 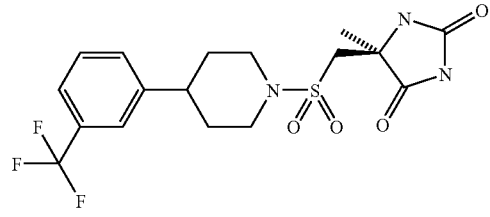 | m/z 420 (MH+) |
| 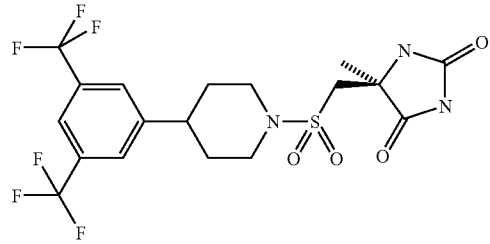 | m/z 488 (MH+) |
| 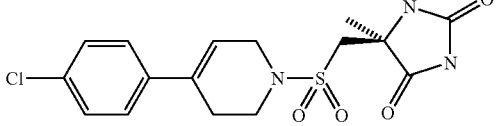 | m/z 384/386 3:1 (MH+) |
| 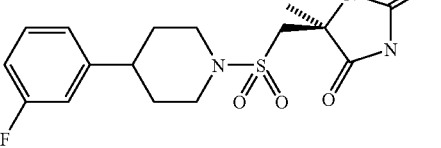 | m/z 370 (MH+) |
| 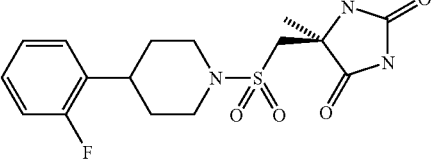 | m/z 370 (MN+) |
| 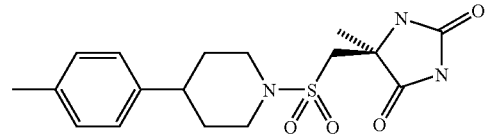 | m/z 366 (MH+) |

-continued
HYDANTOINS OF FORMULA I
| Hydantoin | Analysis[1] |
|---|---|
| 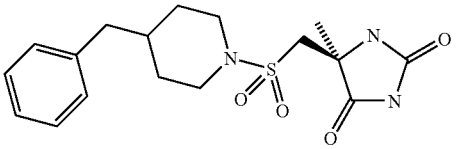 | m/z 366 (MH+) |
| 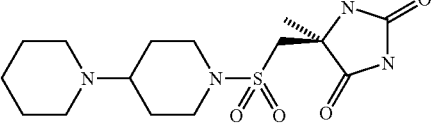 | m/z 359 (MH+) |
| 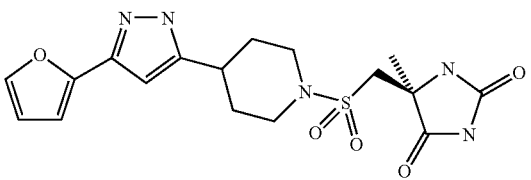 | m/z 408 (MH+) |
| 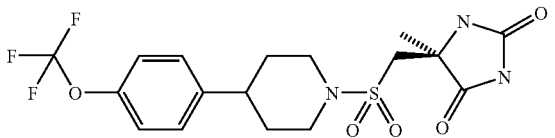 | m/z 436 (MH+) |
| 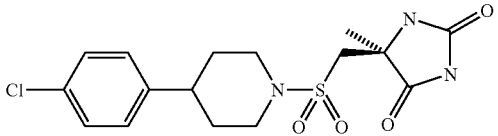 | m/z 386/388 3:1 (MH+) |
| 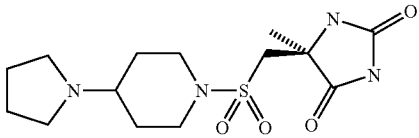 | m/z 345 (MH+) |
| 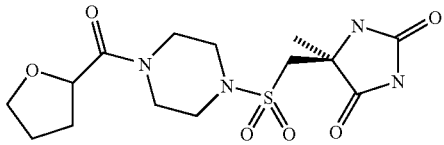 | m/z 375 (MH+) |
| 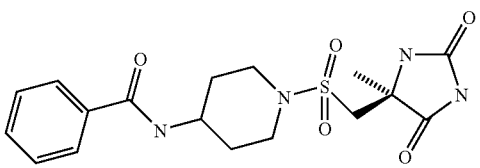 | m/z 395 (MH+) |
| 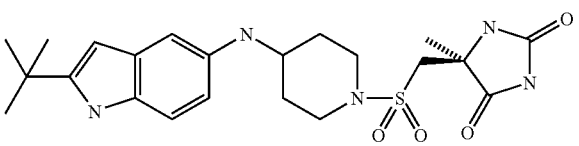 | m/z 462 (MH+) |

-continued
HYDANTOINS OF FORMULA I
| Hydantoin | Analysis[1] |
|---|---|
| 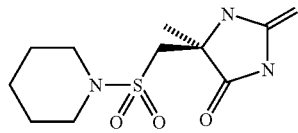 | m/z 276 (MH+) |
| 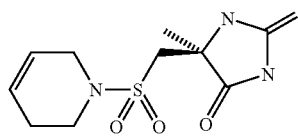 | m/z 274 (MH+) |
| 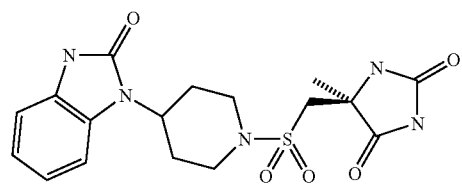 | m/z 408 (MH+) |
| 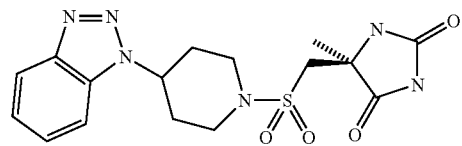 | m/z 393 (MH+) |
| 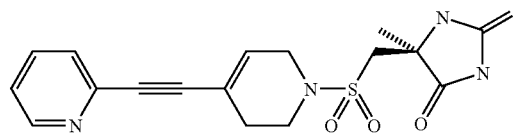 | m/z 375 (MH+) |
| 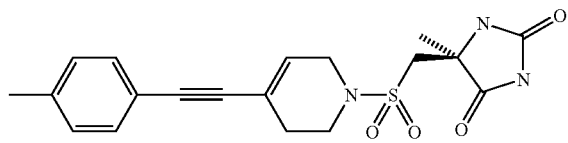 | m/z 388 (MH+) |
| 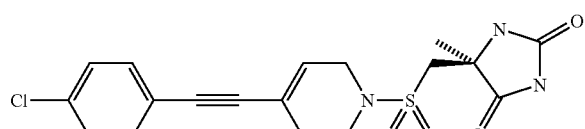 | m/z 408 (MH+) |
| 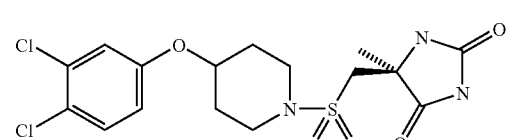 | m/z 436 (MH+) |
| 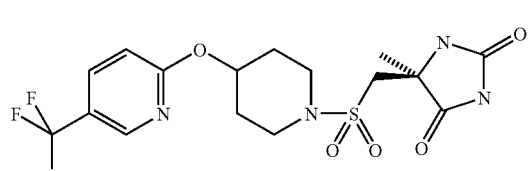 | m/z 437 (MH+) |

-continued
HYDANTOINS OF FORMULA I
| Hydantoin | Analysis[1] |
|---|---|
| 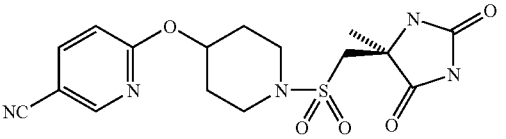 | m/z 394 (MH+) |
| 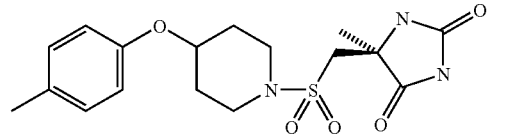 | m/z 382 (MH+) |
| 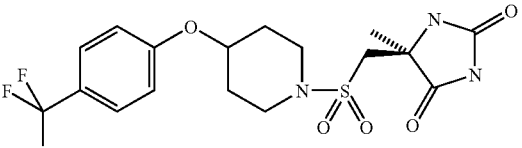 | m/z 436 (MH+) |
| 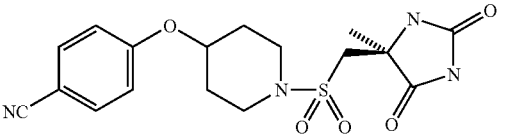 | m/z 393 (MH+) |
| 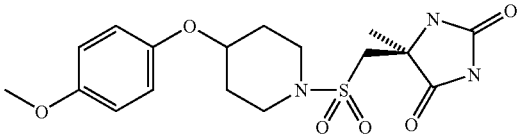 | m/z 398 (MH+) |
| 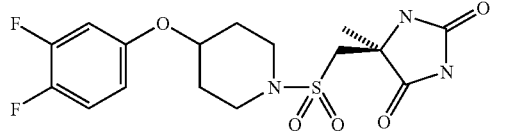 | m/z 404 (MH+) |
| 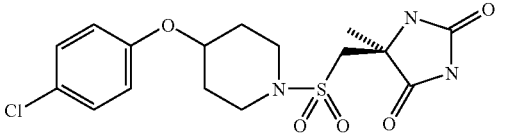 | m/z 402 (MH+) |
| 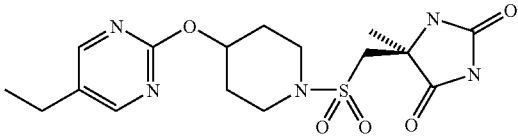 | m/z 398 (MH+) |
| 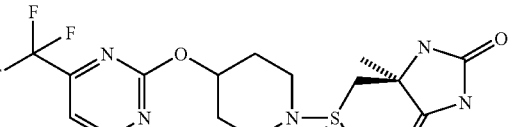 | m/z 438 (MH+) |

-continued
HYDANTOINS OF FORMULA I
| Hydantoin | Analysis[1] |
|---|---|
| 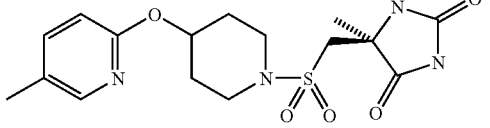 | m/z 383 (MH+) |
| 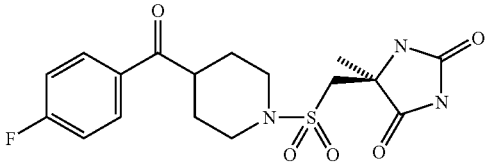 | m/z 398 (MH+) |
| 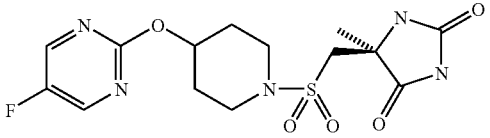 | m/z 388 (MH+) |
| 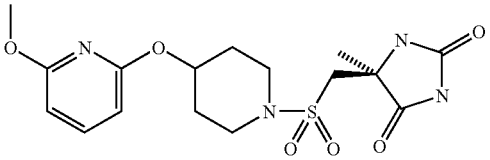 | m/z 399 (MH+) |
| 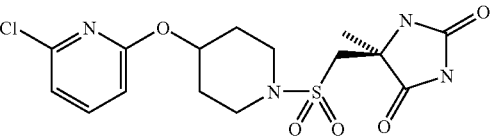 | m/z 403 (MH+) |
| 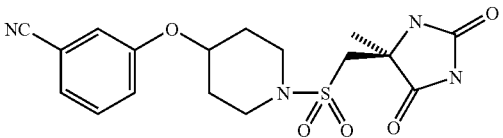 | m/z 393 (MH+) |
| 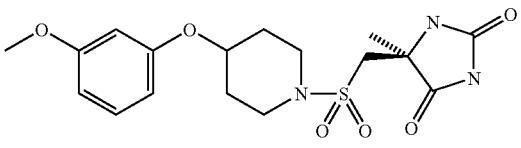 | m/z 398 (MH+) |
| 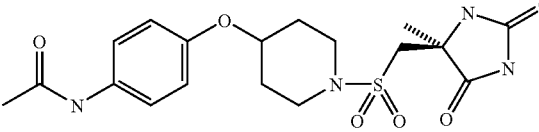 | m/z 425 (MH+) |
| 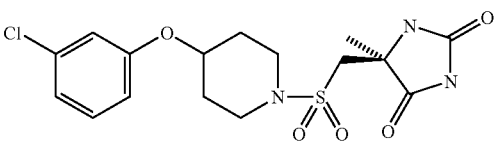 | m/z 402 (MH+) |

-continued

HYDANTOINS OF FORMULA I

| Hydantoin | Analysis[1] |
|---|---|
| [4-(trifluoromethoxy)phenoxy-piperidine sulfonyl methyl hydantoin] | m/z 452 (MH+) |
| [3-(trifluoromethoxy)phenoxy-piperidine sulfonyl methyl hydantoin] | m/z 452 (MH+) |
| [2,4-difluorophenoxy-piperidine sulfonyl methyl hydantoin] | m/z 404 (MH+) |
| [4-fluorophenoxy-piperidine sulfonyl methyl hydantoin] | m/z 386 (MH+) |
| [3-fluorophenoxy-piperidine sulfonyl methyl hydantoin] | m/z 386 (MH+) |
| [2-fluorophenoxy-piperidine sulfonyl methyl hydantoin] | m/z 386 (MH+) |
| [5-methoxypyridin-2-yloxy-piperidine sulfonyl methyl hydantoin] | m/z 399 (MH+) |
| [4-(pyridin-3-yl)phenyl-piperazine sulfonyl methyl hydantoin] | m/z 430 (MH+) |
| [pyridin-2-yloxy-piperidine sulfonyl methyl hydantoin] | m/z 369 (MH+) |

-continued

| HYDANTOINS OF FORMULA I | |
|---|---|
| Hydantoin | Analysis[1] |
| (structure) | m/z 410 (MH+) |
| (structure) | m/z 368 (MH+) |
| (structure) | m/z 413 (MH+) |
| (structure) | m/z 410 (MH+) |
| (structure) | m/z 387 (MH+) |
| (structure) | m/z 475 (MH+) |
| (structure) | m/z 403 (MH+) |
| (structure) | m/z 385 (MH+) |
| (structure) | m/z 418 (MH+) |

HYDANTOINS OF FORMULA I

| Hydantoin | Analysis[1] |
|---|---|
| (4-chlorophenyl-sulfonyl-piperidine sulfonyl methyl hydantoin) | m/z 450 (MH+) |
| (4-fluorophenyl-amino-piperidine sulfonyl methyl hydantoin) | m/z 385 (MH+) |
| (3-acetamidophenoxy-piperidine sulfonyl methyl hydantoin) | m/z 425 (MH+) |
| (4-chlorobenzoyl-piperazine sulfonyl methyl hydantoin) | m/z 415 (MH+) |
| (4-fluorophenyl-carbamoyl-piperidine sulfonyl methyl hydantoin) | m/z 413 (MH+) |
| (5-bromopyridin-2-yloxy-piperidine sulfonyl methyl hydantoin) | m/z 447, 449 (MH+) |
| (5-(4-fluorophenyl)pyridin-2-yl-piperazine sulfonyl methyl hydantoin) | m/z 448 (MH+) |
| (5-(4-methoxyphenyl)pyridin-2-yl-piperazine sulfonyl methyl hydantoin) | m/z 460 (MH+) |
| (5-(4-chlorophenyl)pyridin-2-yl-piperazine sulfonyl methyl hydantoin) | m/z 464, 466 (MH+) |

HYDANTOINS OF FORMULA I

| Hydantoin | Analysis[1] |
|---|---|
| [structure] | m/z 514 (MH+) |
| [structure] | m/z 420 (MH+) |
| [structure] | m/z 419 (MH+) |
| [structure] | m/z 431 (MH+) |
| [structure] | m/z 455 (MH+) |

[1]For NMR-data see experimental part.

The following compounds were prepared in the same way as (5S)-5-({[4-(4-fluorophenyl)piperidin-1-yl]sulfonyl}methyl)-5-methylimidazolidine-2,4-dione (Example 12) and purified either by precipitation and washing with EtOH/water or by preparative HPLC.

(5S)-5-methyl-5-({[4-[4-(methyloxy)phenyl]-3,6-dihydropyridin-1-(2H)-yl]sulfonyl}methyl)imidazolidine-2,4-dione LC-MS (APCI) m/z 380 (MH+).
$^1$H NMR (Methanol-$d_6$): δ 7.35 (2H, d, J=8.9 Hz); 6.87 (2H, d, J=8.9 Hz); 6.01 (1H, dd); 3.92 (2H, dd); 3.78 (3H, s); 3.56, 3.41 (1H each, ABq, J=14.6 Hz); 3.51-3.46 (2H, m); 2.62-2.57 (2H, m); 1.47 (3H, s).

(5S)-5-methyl-5-[({4-[4-(methyloxy)phenyl]piperidin-1-yl}sulfonyl)methyl]imidazolidine-2,4-dione LC-MS (APCI) m/z 382 (MH+).
$^1$H NMR (DMSO-$d_6$): δ 10.73 (1H, s); 8.01 (1H, s); 7.17 (2H, d); 6.85 (2H, d); 3.71 (3H, s); 3.60 (2H, dd); 3.50 (1H, part of ABq, J=14.8 Hz); 2.85 (2H, q); 2.54 (1H, t); 1.79 (2H, d); 1.64-1.53 (2H, m); 1.33 (3H, s).

(5S)-5-({[4-(4-chlorophenyl)-4-hydroxypiperidin-1-yl]sulfonyl}methyl)-5-methylimidazolidine-2,4-dione LC-MS (APCI) m/z 402/404 3:1 (MH+).
$^1$H NMR (DMSO-$d_6$): δ 10.72 (1H, s); 8.01 (1H, s); 7.51 (2H, d); 7.37 (2H, d); 5.22 (1H, s); 3.49, 3.34 (1H each, ABq, J=14.9 Hz); 3.47-3.35 (2H, m); 3.15 (2H, q); 1.93 (2H, t); 1.64 (2H, d); 1.33 (3H, s).

(5S)-5-methyl-5-[({4-[2-(methyloxy)phenyl]piperidin-1-yl}sulfonyl)methyl]imidazolidine-2,4-dione LC-MS (APCI) m/z 382 (MH+).
$^1$H NMR (DMSO-$d_6$): δ 10.72 (1H, s); 8.01 (1H, s); 7.24-7.14 (2H, m); 6.96 (1H, d); 6.90 (1H, t); 3.78 (3H, s); 3.60 (2H, dd); 3.51, 3.33 (1H each, ABq, J=14.7 Hz); 3.02-2.94 (1H, m); 2.88 (2H, q); 1.77 (2H, d); 1.66-1.56 (2H, m); 1.33 (3H, s).

(5S)-5-methyl-5-[({4-[4-(trifluoromethyl)phenyl]piperidin-1-yl}sulfonyl)methyl]imidazolidine-2,4-dione LC-MS (APCI) m/z 420 (MH+).
$^1$H NMR (DMSO-d$_6$): δ 10.73 (1H, s); 8.01 (1H, s); 7.66 (2H, d); 7.50 (2H, d); 3.63 (2H, dd); 3.52, 3.34 (1H each, ABq, J=14.9 Hz); 2.88 (2H, ddd); 2.79-2.68 (1H, m); 1.86 (2H, d); 1.67 (2H, ddd); 1.33 (3H, s).

(5S)-5-methyl-5-[({4-[3-(trifluoromethyl)phenyl]piperidin-1-yl}sulfonyl)methyl]imidazolidine-2,4-dione LC-MS (APCI) m/z 420 (MH+).
$^1$H NMR (DMSO-d$_6$): δ 10.74 (1H, s); 8.02 (1H, s); 7.63-7.52 (4H, m); 3.63 (2H, dd); 3.52 (1H, part of ABq, J=14.9 Hz); 2.87 (2H, ddd); 2.79-2.70 (1H, m); 1.87 (2H, d); 1.75-1.63 (2H, m); 1.33 (3H, s).

(5S)-5-[({4-[3,5-bis(trifluoromethyl)phenyl]piperidin-1-yl}sulfonyl)methyl]-5-methylimidazolidine-2,4-dione LC-MS (APCI) m/z 488 (MH+).
$^1$H NMR (DMSO-d$_6$): δ 10.74 (1H, s); 8.02 (1H, s); 8.00 (2H, s); 7.93 (1H, s); 3.64 (2H, dd); 3.52 (1H, part of ABq, J=14.9 Hz); 2.95-2.81 (3H, m); 1.89 (2H, d); 1.83-1.69 (2H, m); 1.34 (3H, s).

(5S)-5-({[4-(4-chlorophenyl)-3,6-dihydropyridin-1(2H)-yl]sulfonyl}methyl)-5-methylimidazolidine-2,4-dione LC-MS (APCI) m/z 384/386 3:1 (MH+).
$^1$H NMR (DMSO-d$_6$): δ 10.74 (1H, s); 8.03 (1H, s); 7.47 (2H, d); 7.40 (2H, d); 6.23 (1H, app s); 3.85 (2H, app s); 3.52, 3.39 (1H each, ABq, J=14.7 Hz); 3.39-3.32 (2H, m); 2.55 (2H, br s); 1.32 (3H, s).

(5S)-5-({[4-(3-fluorophenyl)piperidin-1-yl]sulfonyl}methyl)-5-methylimidazolidine-2,4-dione LC-MS (APCI) m/z 370 (MH+).
$^1$H NMR (DMSO-d$_6$): δ 10.73 (1H, s); 8.01 (1H, s); 7.38-7.31 (1H, m); 7.15-7.08 (2H, m); 7.05-6.98 (1H, m); 3.62 (2H, dd); 3.51, 3.33 (1H each, ABq, J=14.7 Hz); 2.95-2.80 (2H, m); 2.68-2.60 (1H, m); 1.82 (2H, br d); 1.69-1.58 (2H, m); 1.33 (3H, s).

(5S)-5-({[4-(2-fluorophenyl)piperidin-1-yl]sulfonyl}methyl)-5-methylimidazolidine-2,4-dione LC-MS (APCI) m/z 370 (MH+).
$^1$H NMR (DMSO-d$_6$): δ 10.73 (1H, s); 8.01 (1H, s); 7.36 (1H, t); 7.30-7.20 (1H, m); 7.18-7.12 (2H, m); 3.63 (2H, dd); 3.52, 3.33 (1H each, ABq); 2.96-2.85 (3H, m); 1.80 (2H, brd); 1.69 (2H, ddd); 1.33 (3H, s).

(5S)-5-methyl-5-({[4-(4-(4-methylphenyl)piperidin-1-yl]sulfonyl}methyl)imidazolidine 2,4-dione LC-MS (APCI) m/z 366 (MH+).
$^1$H NMR (DMSO-d$_6$): δ 10.73 (1H, s); 8.01 (1H, s); 7.15-7.07 (4H, m); 3.60 (2H, dd); 3.50, 3.32 (1H each, ABq); 2.85 (2H, q); 2.59-2.51 (1H, m); 2.25 (3H, s); 1.79 (2H, br d); 1.60 (2H, ddd).

(5S)-5-methyl-5-({[4-(phenylmethyl)piperidin-1-yl]sulfonyl}methyl)imidazolidine-2,4-dione LC-MS (APCI) m/z 366 (MH+).
$^1$H NMR (DMSO-d$_6$): δ 10.70 (1H, s); 7.96 (1H, s); 7.29-7.15 (5H, m); 3.46 (2H, t); 3.41, 3.24 (1H each, ABq, J=14.9 Hz); 2.68 (2H, dt); 2.52 (2H, d); 1.54-1.51 (3H, m); 1.30 (3H, s).

(5S)-5-[(1,4'-bipiperidin-1'-ylsulfonyl)methyl]-5-methylimidazolidine-2,4-dione trifluoroacetic acid LC-MS (APCI) m/z 359 (MH+).
$^1$H NMR (DMSO-d$_6$): δ 10.74 (1H, s); 9.25 (1H, br s); 8.02 (1H, s); 3.63 (2H, t); 3.51, 3.34 (1H each, ABq, J=14.8 Hz); 3.39 (2H, d); 3.24 (1H, t); 2.92 (2H, q); 2.81 (2H, t); 2.07 (2H, d); 1.82 (2H, d); 1.74-1.58 (5H, m); 1.45-1.34 (1H, m); 1.31 (3H, s).
$^{19}$F NMR (DMSO-d$_6$): δ −74.48.

(5S)-5-({[4-(3-furan-2-yl-1H-pyrazol-5-yl)piperidin-1-yl]sulfonyl}methyl)-5-methylimidazolidine-2,4-dione LC-MS (APCI) m/z 408 (MH+).
$^1$H NMR (DMSO-d$_6$): δ 10.73 (1H, s); 8.01 (1H, s); 7.66 (1H, s); 6.64 (1H, s); 6.53 (1H, s); 6.34 (1H, s); 3.61-3.49 (2H, m); 3.49 (1H, half ABq, J=14.9 Hz); 2.94-2.84 (2H, m); 2.81-2.72 (1H, m); 1.98 (2H, br d); 1.70-1.58 (2H, m); 1.32 (3H, s).

(5S)-5-methyl-5-{[(4-{4-[(trifluoromethyl)oxy]phenyl}piperidin-1-yl)sulfonyl]methyl}imidazolidine-2,4-dione LC-MS (APCI) m/z 436 (MH+).
$^1$H NMR (DMSO-d$_6$): δ 10.73 (1H, s); 8.01 (1H, s); 7.40 (2H, d); 7.28 (2H, d); 3.70-3.55 (2H, m); 3.51, 3.33 (1H each, ABq, J=14.7 Hz); 2.94-2.80 (2H, m); 2.73-2.61 (2H, m); 1.86 (2H, d); 1.71-1.57 (2H, m); 1.33 (3H, s).

(5S)-5-({[4-(4-chlorophenyl)piperidin-1-yl]sulfonyl}methyl)-5-methylimidazolidine-2,4-dione LC-MS (APCI) m/z 386/388 3:1 (MH+).
$^1$H NMR (DMSO-d$_6$): δ 10.73 (1H, s); 8.01 (1H, s); 7.36-7.28 (4H, m); 3.66-3.54 (2H, m); 3.51, 3.33 (1H each, ABq, J=14.9 Hz); 2.92-2.80 (2H, m); 2.67-2.58 (1H, m); 1.81 (2H, br d); 1.68-1.56 (2H, m); 1.33 (3H, s).

(5S)-5-methyl-5-{[(4-pyrrolidin-1-ylpiperidin-1-yl)sulfonyl]methyl}imidazolidine-2,4-dione trifluoroacetic acid LC-MS (APCI) m/z 345 (MH+).
$^1$H NMR (DMSO-d): δ 10.74 (1H, s); 9.61 (1H, br s); 8.01 (1H, s); 3.60 (2H, t); 3.51, 3.36 (1H each, ABq, J=14.8 Hz); 3.55-3.47 (2H, m); 3.27-3.15 (1H, m); 3.13-3.02 (2H, m); 2.80 (2H, t); 2.12 (2H, br d); 2.07-1.94 (2H, m); 1.86-1.77 (2H, m); 1.62-1.49 (2H, m); 1.32 (3H, s).
$^{19}$F NMR (DMSO-d$_6$): δ −74.02

(5S)-5-methyl-5-({[4-tetrahydrofuran-2-ylcarbonyl)piperazin-1-yl]sulfonyl}methyl)imidazolidine-2,4-dione LC-MS (APCI) m/z 375 (MH+).
¹H NMR (DMSO-d₆): δ 10.73 (1H, s); 8.01 (1H, s); 4.65 (1H, dd); 3.80-3.68 (2H, m); 3.60-3.42 (3H and water, m); 3.33 (1H, half ABq, J=14.9 Hz); 3.19-3.00 (4H, m); 2.09-1.92 (2H, m); 1.87-1.75 (2H, m); 1.30 (3H, s).

N-[1-({[(4S)-4-methyl-2,5-dioxoimidazolidin-4-yl]methyl}sulfonyl)piperidin-4-yl]benzamide LC-MS (APCI) m/z 395 (MH+).
¹H NMR (DMSO-d₆): δ 10.72 (1H, s); 8.30 (1H, d); 8.01 (1H, s); 7.82 (2H, d); 7.51 (1H, t); 7.45 (2H, t); 3.96-3.85 (1H, m); 3.52 (2H, t); 3.50, 3.32 (1H each, ABq, J=14.7 Hz); 2.92 (2H, t); 1.88 (2H, d); 1.55 (2H, q); 1.33 (3H, s).

(5S)-5-{[(4-{[(1,1-dimethylethyl)-1H-indol-5-yl]amino}piperidin-1-yl)sulfonyl]methyl}-5-methylimidazolidine-2,4-dione LC-MS (APCI) m/z 462 (MH+).
¹H NMR (DMSO-d₆): δ 10.72 (1H, s); 10.37 (1H, s); 8.00 (1H, s); 7.02 (1H, d, J=8.4 Hz); 6.58 (1H, s); 6.45 (1H, d, J=8.4 Hz); 5.86 (1H, s); 4.65 (1H, Br s); 3.48, 3.29 (1H each, ABq, J=14.7 Hz); 3.46 (2H, t); 2.93 (2H, t); 1.95 (2H, t); 1.45-1.35 (2H, m); 1.33 (3H, s); 1.29 (9H, s).

(5S)-5-methyl-5-[(piperidin-1-ylsulfonyl)methyl]imidazolidine-2,4-dione

LC-MS (APCI) m/z 276 (MH+).
¹H NMR (DMSO-d₆): δ 10.70 (1H, s); 7.97 (1H, s); 3.44, 3.23 (1H each, ABq, J=14.8 Hz); 3.13-3.01 (4H, m); 1.58-1.42 (6H, m); 1.30 (3H, s).

(5S)-5-[3,6-dihydropyridin-1(2H)-ylsulfonyl)methyl]-5-methylimidazolidine-2,4-dione LC-MS (APCI) m/z 274 (MH+).
¹H NMR (DMSO-d₆): δ 10.72 (1H, s); 8.00 (1H, s); 5.85-5.78 (1H, m); 5.74-5.68 (1H, m); 3.67-3.62 (2H, m); 3.47, 3.33 (1H each, ABq, J=14.7 Hz); 3.22 (2H, dd); 2.14-2.10 (2H, m); 1.31 (3H, s).

(5S)-5-methyl-5-{[4-(2-oxo-2,3-dihydro-1H-benzimidazol-1-yl)piperidin-1-yl]sulfonyl}methyl)imidazolidine-2,4-dione LC-MS (APCI) m/z 408 (MH+).
¹H NMR (DMSO-d₆): δ 10.86 (1H, s); 10.75 (1H, s); 8.02 (1H, s); 7.27-7.17 (1H, m); 7.05-6.91 (3H, m); 4.38-4.20 (1H, m); 3.65 (2H, t); 3.56, 3.38 (1H each, ABq, J=14.8 Hz); 3.03-2.90 (2H, m); 2.41-2.24 (2H, m); 1.76 (2H, d); 1.34 (3H, s).

(5S)-5-([{4-(1H-1,2,3-benzotriazol-1-yl)piperidin-1-yl]sulfonyl}methyl)-5-methylimidazolidine-2,4-dione LC-MS (APCI) m/z 393 (MH+).
¹H NMR (DMSO-d₆): δ 10.77 (1H, s); 8.05 (1H, s); 8.05 (1H, d); 7.93 (1H, d); 7.56 (1H, t); 7.41 (1H, t); 5.12-4.97 (1H, m); 3.71 (2H, t); 3.58, 3.43 (1H each, ABq, J=14.7 Hz); 3.19-3.03 (2H, m); 2.29-2.16 (4H, m); 1.35 (3H, s).

(5S)-5-methyl-5-({[4-pyridin-2-ylethynyl)-3,6-dihydropyridin-1(2H)-yl]sulfonyl}methyl)imidazolidine-2,4-dione trifluoroacetic acid LC-MS (APCI) m/z 375 (MH+).
¹H NMR (DMSO-d₆): δ 10.57 (1H, s); 8.56 (1H, d); 8.03 (1H, s); 7.82 (1H, t); 7.53 (1H, d); 7.38 (1H, dd); 6.31 (1H, br s); 3.83 (2H, d); 3.54, 3.41 (1H each, ABq, J=14.8 Hz); 3.36-3.25 (2H, m); 2.42-2.34 (2H, m); 1.32 (3H, s).
¹⁹F NMR (DMSO-d₆): δ −75.10

(5S)-5-methyl-5-({[4-[(4-methylphenyl)ethynyl]-3,6-dihydropyridin-1(2H)-yl]sulfonyl}methyl)imidazolidine-2,4-dione LC-MS (APCI) m/z 388 (MH+).
¹H NMR (DMSO-d₆): δ 10.74 (1H, s); 8.02 (1H, s); 7.32 (2H, d); 7.19 (2H, d); 6.17 (1H, br s); 3.80 (2H, d); 3.52, 3.39 (1H each, ABq, J=14.8 Hz); 3.29 (2H, t); 2.39-2.32 (2H, m); 2.30 (3H, s); 1.32 (3H, s).

(5S)-5-({[4-[(4-chlorophenyl)ethynyl]-3,6-dihydropyridin-1(2H)-yl]sulfonyl}methyl)-5-methylimidazolidine-2,4-dione LC-MS (APCI) m/z 408 (MH+).
¹H NMR (DMSO-d₆): δ 10.74 (1H, s); 8.02 (1H, s); 7.54-7.38 (4H, m); 6.23 (1H, br s); 3.87-3.76 (2H, m); 3.53, 3.41 (1H each, ABq, J=14.9 Hz); 3.34-2.25 (2H, m); 2.42-2.29 (2H, m); 1.32 (3H, s).

(5S)-5-[4-(3,4-Dichloro-phenoxy)-piperidine-1-sulfonylmethyl]-5-methyl-imidazolidine-2,4-dione LC-MS (APCI) m/z (APCI) m/z 436.1 (MH+).
¹H NMR (DMSO-d₆): δ 10.74 (1H, s); 8.01 (1H, s); 7.53 (1H, d, J=9.2 Hz); 7.31 (1H, d, J=2.9 Hz); 7.02 (1H, dd, J=9.2, 2.9 Hz); 4.65-4.57 (1H, m); 3.51, 3.34 (1H each, ABq, J=15.2 Hz); 3.39-3.27 (2H, m); 3.17-3.08 (2H, m); 2.00-1.90 (2H, m); 1.75-1.65 (2H, m); 1.33 (3H, s).

(5S)-5-[4-(5-Chloro-pyridin-2-yloxy)-piperidine-1-sulfonylmethyl]-5-methyl imidazolidine-2,4-dione LC-MS (APCI) m/z 403.3 (MH+).
¹H NMR (DMSO-d₆): δ 10.74 (1H, s); 8.20 (1H, d, J=2.7 Hz); 7.81 (1H, dd, J=8.7, 2.7 Hz); 6.87 (1H, d, J=2.7 Hz); 5.16-5.03 (1H, m); 3.52, 3.35 (1H each, ABq, J=15.0 Hz); 3.43-3.28 (2H, m); 3.19-3.07 (2H, m); 2.08-1.95 (2H, m); 1.80-1.65 (2H, m); 1.33 (3H, s).

(5S)-5-Methyl-5-[4-(5-trifluoromethyl-pyridin-2-yloxy)-piperidine-1-sulfonylmethyl]-imidazolidine-2,4-dione LC-MS (APCI) m/z 437 (MH+).
¹H NMR (CDCl₃): δ 8.95 (1H, s); 8.42-8.38 (1H, m); 7.79 (1H, dd, J=8.8, 2.5 Hz); 6.81 (1H, d, J=8.8 Hz); 6.71 (1H, s); 5.40-5.28 (1H, m); 3.52-3.39 (2H, m); 3.40-3.28 (2H, m); 3.32 (2H, ABq, J=24.6, 14.0 Hz); 2.16-2.02 (2H, m); 2.02-1.84 (2H, m); 1.67 (3H, s).

6-[1-((4S)-4-Methyl-2,5-dioxo-imidazolidin-4-yl-methanesulfonyl)-piperidin-4-yloxy]-nicotinonitrile LC-MS (APCI) m/z 394.3 (MH+).
$^1$H NMR (DMSO-d$_6$): δ 10.72 (1H, s); 8.68 (1H, d, J=2.3 Hz); 8.14 (1H, dd, J=8.7, 2.3 Hz); 8.00 (1H, s); 6.98 (1H, d, J=8.7 Hz); 5.27-5.14 (1H, m); 3.56-3.28 (4H, m); 3.18-3.06 (2H, m); 2.08-1.96 (2H, m); 1.81-1.66 (2H, m); 1.31 (3H, s).

(5S)-5-Methyl-5-(4-p-tolyloxy-Piperidine-1-sulfonylmethyl)-imidazolidine-2,4-dione LC-MS (APCI) m/z 382.5 (MH+).
$^1$H NMR (DMSO-d$_6$): δ 10.73 (1H, s); 8.01 (1H, s); 7.09 (2H, d, J=8.4 Hz); 6.87 (2H, d, J=8.4 Hz); 4.50-4.42 (1H, m); 3.50, 3.34 (1H each, ABq, J=14.8 Hz); 3.38-3.29 (2H, m); 3.17-3.09 (2H, m); 2.23 (3H, s); 1.99-1.89 (2H, m); 1.73-1.63 (2H, m); 1.33 (3H, s).

(5S)-5-Methyl-5-[4-(4-trifluoromethyl-phenoxy)-piperidine-1-sulfonylmethyl]-imidazolidine-2,4-dione LC-MS (APCI) m/z 436.3 (MH+).
$^1$H NMR (DMSO-d$_6$): δ 10.71 (1H, brs); 8.02 (1H, s); 7.65 (2H, d, J=8.8 Hz); 7.17 (2H, d, J=8.8 Hz); 4.72-4.64 (1H, m); 3.52, 3.35 (1H each, ABq, J=14.7 Hz); 3.40-3.28 (2H, m); 3.19-3.10 (2H, m); 2.05-1.95 (2H, m); 1.78-1.68 (2H, m); 1.33 (3H, s).

4-[1-(4S)-4-Methyl-2,5-dioxo-imidazolidin-4-yl-methanesulfonyl)piperidin-4-yloxy]-benzonitrile LC-MS (APCI) M/Z 393.2 (MH+).
$^1$H NMR (DMSO-d$_6$): δ 10.73 (1H, s); 8.00 (1H, s); 7.76 (2H, d, J=8.8 Hz); 7.15 (2H, d, J=8.8 Hz); 4.74-4.65 (1H, m); 3.51, 3.34 (1H each, ABq, J=14.9 Hz); 3.40-3.27 (2H, m); 3.17-3.07 (2H, m); 2.03-1.94 (2H, m); 1.77-1.66 (2H, m); 1.32 (3H, s).

(5S)-5-[4-(4-Methoxy-phenoxy)-piperidine-1-sulfonylmethyl]-5-methyl-imidazolidine-2,4-dione LC-MS (APCI) m/z 398.2 (MH+).
$^1$H NMR (DMSO-d$_6$): δ 10.73 (1H, s); 8.01 (1H, s); 6.89 (4H, ABq, J=29.1, 9.1 Hz); 4.43-4.34 (1H, m); 3.70 (3H, m); 3.51, 3.33 (1H, ABq, J=15.0 Hz); 3.38-3.28 (2H, m); 3.16-3.05 (2H, m); 1.97-1.87 (2H, m); 1.73-1.62 (2H, m); 1.33 (3H, s).

(5S)-5-[4-(3,4-Difluoro-phenoxy)-piperidine-1-sulfonylmethyl]-5-methyl-imidazolidine-2,4-dione LC-MS (APCI) m/z 404.2 (MH+).
$^1$H NMR (DMSO-d$_6$): δ 10.74 (1H, s); 8.01 (1H, s); 7.35 (1H, q, J=19.6, 9.2 Hz); 7.19-7.11 (1H, m); 6.86-6.80 (1H, m); 4.57-4.48 (1H, m); 3.51, 3.34 (1H each, ABq, J=14.9 Hz); 3.38-3.28 (2H, m); 2.16-2.06 (2H, m); 2.00-1.90 (2H, m); 1.74-1.64 (2H, m); 1.33 (3H, s).

(5S)-5-[4-(4-Chloro-phenoxy)-piperidine-1-sulfonylmethyl]-5-methyl-imidazolidine-2,4-dione LC-MS (APCI) m/z 402 (MH+).
$^1$H NMR (DMSO-d$_6$): δ 10.73 (1H, s); 8.00 (1H, s); 7.32 (2H, d, J=8.8 Hz); 7.00 (2H, d, J=8.8 Hz); 4.56-4.48 (1H, m); 3.50, 3.33 (1H each, ABq, J=14.8 Hz); 3.37-3.28 (2H, m); 3.16-3.06 (2H, m); 2.00-1.90 (2H, m); 1.73-1.63 (2H, m); 1.32 (3H, s).

(5S)-5-[4-(5-Ethyl-pyrimidin-2-yloxy)-piperidine-1-sulfonylmethyl]-5-methyl-imidazolidine-2,4-dione LC-MS (APCI) m/z 398 (MH+).
$^1$H NMR (DMSO-d$_6$): δ 10.74 (1H, s); 8.47 (2H, s); 8.02 (1H, s); 5.11-5.03 (1H, m); 3.52, 3.35 (1H each, ABq, J=14.8 Hz); 3.42-3.28 (2H, m); 3.19-3.10 (2H, m); 2.54 (2H, q, J=15.2, 7.6 Hz); 2.06-1.98 (2H, m); 1.81-1.71 (2H, m); 1.33 (3H, s); 1.17 (3H, t, J=7.2 Hz).

(5S)-5-Methyl-5-[4-(4-trifluoromethyl-pyrimidin-2-yloxy)piperidine-1-sulfonylmethyl]-imidazolidine-2,4-dione LC-MS (APCI) m/z 438 (MH+).
$^1$H NMR (CDCl$_3$): δ 8.84-8.76 (1H, m); 8.02 (1H, s); 7.31 (1H, d, J=4.8 Hz); 6.33 (1H, s); 5.41-5.34 (1H, m); 4.54-4.42 (4H, m); 3.35, 3.24 (1H each, ABq, J=12.9 Hz); 2.17-2.07 (4H, m); 2.02 (3H, s).

(5S)-5-Methyl-5-[4-(5-methyl-pyridin-2-yloxy)-piperidine-1-sulfonylmethyl]-imidazolidine-2,4-dione LC-MS (APCI) m/z 383 (MH+).
$^1$H NMR (CDCl$_3$): δ 8.14 (1H, s); 8.06-7.99 (2H, m); 7.19 (1H, s); 7.09 (1H, d, J=11.6 Hz); 5.28-5.21 (1H, m); 3.70-3.41 (6H, m); 2.44 (3H, s); 2.13-1.96 (4H, m); 1.62 (3H, s).

(5S)-5-[4-(4-Fluoro-benzoyl)-piperidine-1-sulfonylmethyl]-5-methyl-imidazolidine-2,4-dione LC-MS (APCI) m/z 398 (MH+).
$^1$H NMR (DMSO-d$_6$): δ 8.06 (2H, q, J=9.2, 6.0 Hz); 7.40 (2H, t, J=8.8 Hz); 3.61-3.41 (4H, m); 3.00-2.91 (2H, m); 1.90-1.81 (2H, m); 1.62-1.50 (2H, m); 1.33 (3H, s).

(5S)-5-[4-(5-Fluoro-pyrimidin-2-yloxy)-piperidine-1-sulfonylmethyl]-5-methyl imidazolidine-2,4-dione LC-MS (APCI) m/z 388 (MH+).
$^1$H NMR (CDCl$_3$): δ 8.42 (2H, s); 8.30 (1H, s); 6.40 (1H, s); 5.30-5.23 (1H, m); 3.53-3.35 (4H, m); 3.36, 3.21 (1H each, ABq, J=14.4 Hz); 2.10-2.02 (4H, m); 1.70 (3H, s).

(5S)-5-[4-(6-Methoxy-pyridin-2-yloxy)-piperidine-1-sulfonylmethyl]-5-methyl-imidazolidine-2,4-dione LC-MS (APCI) m/z 399 (MH+).
$^1$H NMR (MeOD): δ 7.54 (1H, t, J=8.4 Hz); 6.33-6.28 (2H, m); 5.24-5.14 (1H, m); 3.86 (3H, s); 3.53-3.42 (2H, m); 3.58, 3.39 (1H each, ABq, J=14.4 Hz); 3.30-3.22 (2H, m); 2.13-2.02 (2H, m); 1.96-1.82 (2H, m); 1.47 (3H, s).

(5S)-5-[4-(6-Chloro-pyridin-2-yloxy)-piperidine-1-sulfonyl methyl]-5-methyl-imidazolidine-2,4-dione LC-MS (APCI) m/z 403 (MH+).
$^1$H NMR (MeOD): δ 7.65 (1H, t J=7.8 Hz); 6.97 (1H, d, J=7.2 Hz); 6.73 (1H, d, J=7.2 Hz); 5.25-5.14 (1H, m); 3.55-3.44 (2H, m); 3.58, 3.39 (1H each, ABq, J=14.4 Hz); 3.28-3.19 (2H, m); 2.14-2.02 (2H, m); 1.92-1.79 (2H, m); 1.47 (3H, s).

3-[1-((4S)-4-Methyl-2,5-dioxo-imidazolidin-4-yl-methanesulfonyl)-piperidin-4-yloxy]-benzonitrile LC-MS (APCI) m/z 393 (MH+).
$^1$H NMR (DMSO-d$_6$): δ 10.74 (1H, s); 8.02 (1H, s); 7.52-7.47 (2H, m); 7.42-7.38 (1H, m); 7.36-7.31 (1H, m); 4.69-4.61 (1H, m); 3.52, 3.35 (1H each, ABq, J=17.2 Hz); 3.18-3.07 (2H, m); 2.02-1.95 (2H, m); 1.79-1.65 (2H, m); 1.33 (3H, s).

(5S)-5-[4-(3-Methoxy-phenoxy)-piperidine-1-sulfonylmethyl]-5-methyl-imidazolidine-2,4-dione LC-MS (APCI) m/z 398 (MH+).
$^1$H NMR (DMSO-d$_6$): δ 10.74 (1H, s); 8.01 (1H, s); 7.21-7.15 (1H, m); 6.58-6.50 (3H, m); 4.57-4.49 (1H, m); 3.73 (3H, s); 3.51, 3.34 (1H each, ABq, J=14.4 Hz); 3.17-3.08 (2H, m); 2.01-1.91 (2H, m); 1.74-1.64 (2H, m); 1.33 (3H, s).

N-{4-[1-((4S)-Methyl-2,5-dioxo-imidazolidin-4-ylmethanesulfonyl)-piperidin-4-yloxy]-phenyl}-acetamide LC-MS (APCI) m/z 425 (MH+).
$^1$H NMR (DMSO-d$_6$): δ 10.69 (1H, brs); 9.78 (1H, s); 8.00 (1H, s); 7.47 (2H, d, J=9.2 Hz); 6.91 (2H, d, J=9.2 Hz); 4.48-4.41 (1H, m); 3.51 (1H from ABq, J=14.4 Hz); 3.16-3.06 (2H, m); 2.00 (3H, s); 1.98-1.90 (2H, m); 1.73-1.63 (2H, m); 1.33 (3H, s).

(5S)-5-[4-(3-Chloro-phenoxy)-piperidine-1-sulfonylmethyl]-5-methyl-imidazolidine-2,4-dione LC-MS (APCI) m/z 402 (MH+).
$^1$H NMR (DMSO-d$_6$): δ 10.76 (1H, brs); 7.99 (1H, s); 7.31 (1H, t, J=8.4 Hz); 7.08 (1H, t, J=2.2 Hz); 7.02-6.95 (2H, m); 4.64-4.56 (1H, m); 3.51 (1H from ABq, J=14.4 Hz); 3.17-3.09 (2H, m); 2.00-1.91 (2H, m); 1.75-1.65 (2H, m); 1.33 (3H, s).

(5S)-5-Methyl-5-[4-(4-trifluoromethoxy-phenoxy)-piperidine-1-sulfonylmethyl]-imidazolidine-2,4-dione LC-MS (APCI) m/z 452 (MH+).
$^1$H NMR (DMSO-d$_6$): δ 10.74 (1H, s); 8.01 (1H, s); 7.29 (2H, d, J=8.8 Hz); 7.08 (2H, d, J=9.2 Hz); 4.60-4.52 (1H, m); 3.51 (1H from ABq, J=14.8 Hz); 3.17-3.08 (2H, m); 2.02-1.93 (2H, m); 1.75-1.65 (2H, m); 1.33 (3H, s).

(5S)-5-Methyl-5-[4-(3-trifluoromethoxy-Phenoxy)-piperidin-1-sulfonylmethyl]-imidazolidine-2,4-dione LC-MS (APCI) m/z 452 (MH+).
$^1$H NMR (DMSO-d$_6$): δ 10.74 (1H, s); 8.01 (1H, s); 7.41 (1H, t, J=8.4 Hz); 7.06-6.91 (3H, m); 4.65-4.58 (1H, m); 3.51 (1H from ABq, J=14.8 Hz); 3.18-3.08 (2H, m); 2.02-1.93 (2H, m); 1.76-1.65 (2H, m); 1.33 (3H, s).

(5S)-5-[4-(2,4-Difluoro-phenoxy)-piperidine-1-sulfonylmethyl]-5-methyl-imidazolidine-2,4-dione LC-MS (APCI) m/z 404 (MH+).
$^1$H NMR (DMSO-d$_6$): δ 10.74 (1H, s); 8.02 (1H, s); 7.34-7.23 (2H, m); 7.06-6.97 (1H, m); 4.50-4.41 (1H, m); 3.50 (1H from ABq); 3.17-3.06 (2H, m); 2.02-1.90 (2H, m); 1.78-1.65 (2H, m); 1.33 (3H, s).

(5S)-5-[4-(4-Fluoro-phenoxy)-piperidine-1-sulfonylmethyl]-5-methyl-imidazolidine-2,4-dione LC-MS (APCI) m/z 386 (MH+).
$^1$H NMR (DMSO-d$_6$): δ 10.75 (1H, s); 8.02 (1H, s); 7.17-6.97 (2H, m); 4.52-4.43 (1H, m); 3.17-3.06 (2H, m); 2.00-1.89 (2H, m); 1.75-1.62 (2H, m); 1.33 (3H, s).

(5S)-5-[4-(3-Fluoro-phenoxy)-piperidine-1-sulfonylmethyl]-5-methyl-imidazolidine-2,4-dione LC-MS (APCI) m/z 386 (MH+).
$^1$H NMR (DMSO-d$_6$): δ 10.72 (1H, s); 8.02 (1H, s); 7.36-7.26 (1H, m); 6.91-6.71 (3H, m); 4.62-4.52 (1H, m); 3.18-3.06 (2H, m); 2.02-1.91 (2H, m); 1.78-1.63 (2H, m); 1.33 (3H, s).

(5S)-5-[4-(2-Fluoro-phenoxy)-piperidine-1-sulfonylmethyl]-5-methyl-imidazolidine-2,4-dione LC-MS (APCI) m/z 386 (MH+).
$^1$H NMR (DMSO-d$_6$): δ 10.74 (1H, s); 8.01 (1H, s); 7.28-7.17 (2H, m); 7.17-7.08 (1H, m); 7.02-6.97 (1H, m); 4.59-4.47 (1H, m); 2.04-1.92 (2H, m); 1.80-1.67 (2H, m); 1.33 (3H, s).

(5S)-5-[4-(5-Methoxy-pyridin-2-yloxy)-piperidine-1-sulfonylmethyl]-5-methyl-imidazolidine-2,4-dione LC-MS (APCI) m/z 399 (MH+).
$^1$H NMR (DMSO-d$_6$): δ 10.74 (1H, s); 8.01 (1H, s); 7.89 (1H, d, J=3.16 Hz); 7.39 (1H, dd, J=3.18, 9.07 Hz); 6.77 (1H, d, J=8.95 Hz); 5.08-4.96 (1H, m); 3.76 (3H, s); 3.51, 3.34 (1H each, ABq, J=14.7 Hz); 3.43-3.29 (2H, m); 3.18-3.05 (2H, m); 2.05-1.94 (2H, m); 1.77-1.61 (2H, m); 1.33 (3H, s).

(5S)-5-Methyl-5-[4-(4-pyridin-3-yl-phenyl)piperazine-1-sulfonylmethyl]-imidazolidine-2,4-dione LC-MS (APCI) m/z 430 (MH+).
$^1$H NMR (DMSO-d$_6$): δ 10.76 (1H, s); 8.99 (1H, s); 8.60 (1H, d, J=4.91 Hz); 8.35 (1H, d, J=7.81 Hz); 8.04 (1H, s); 7.70 (2H, d, J=8.87 Hz); 7.12 (2H, d, J=8.91 Hz); 3.57 (1H from ABq); 3.35 (4H, m); 3.27 (4H, m); 1.33 (3H, s).

(5S)-5-methyl-5-({[4-pyridin-2-yloxy)piperidin-1-yl]sulfonyl}methyl)imidazolidine-2,4-dione LC-MS (APCI) m/z 369 (MH+).
$^1$H NMR (CDCl$_3$): δ 1.73 (3H, s); 1.96-2.04 (2H, m); 2.04-2.13 (2H, m); 3.21 (1H, d); 3.36-3.42 (3H, m); 3.45-3.50 (2H, m); 5.29-5.33 (1H, m); 6.30 (1H, bs); 6.78 (1H, d); 6.93 (1H, t); 7.65 (1H, t); 7.70 (1H, bs); 8.16 (1H, d).

(5S)-5-[({4-[(3,4-dimethylbenzyl)oxy]piperidin-1-yl}sulfonyl)methyl]-5-methylimidazolidine-2,4-dione (NB. contains 30% of the 2,3-dimethyl isomer which was in the starting material)
LC-MS (APCI) m/z 410 (MH+).
$^1$H NMR (DMSO-d$_6$): δ 1.3 (3H, s); 1.53-1.64 (2H, m); 1.83-1.89 (2H, m); 2.18 (3H, s); 2.20 (3H, s); 2.95-3.33 (2H, m); 3.25-3.31 (3H, m); 3.45 (1H, d); 3.45-3.53 (1H, m); 4.42 (2H, s); 7.01-7.15 (3H, m); 7.97 (1H, s); 10.70 (1H, s).

(5S)-5-methyl-5-{[(4-phenoxypiperidin-1-yl)sulfonyl]methyl}imidazolidine-2,4-dione LC-MS (APCI) m/z 368 (MH+).
¹H NMR (DMSO-d₆): δ 1.30 (3H, s); 1.64-1.73 (2H, m); 1.92-2.00 (2H, m); 3.08-3.15 (2H, m); 3.28-3.44 (4H, m); 4.49-4.54 (1H, m); 6.92 (1H, t); 6.96 (2H, d); 7.28 (2H, t); 7.69 (1H, bs); 10.7 (1H, bs).

4-Fluoro-N-[1-((4S)-4-methyl-2,5-dioxo-imidazolidin-4-ylmethanesulfonyl)-piperidin-4-yl]-benzamide LC-MS (APCI) m/z 413 (MH+).
¹H NMR (DMSO-d₆): δ 10.73 (1H, s); 8.34 (1H, d, J=7.50 Hz); 8.02 (1H, s); 7.94-7.88 (2H, m); 7.33-7.26 (2H, m); 3.96-3.86 (1H, m); 3.58-3.47 (2H, m); 3.51, 3.32 (1H each, ABq, J=14.81 Hz); 2.97-2.88 (2H, m); 1.92-1.84 (2H, m); 1.62-1.48 (2H, m); 1.33 (3H, s).

(5S)-5-[({4-[(2,5-dimethylbenzyl)oxy]piperidin-1-yl}sulfonyl)methyl]-5-methylimidazolidine-2,4-dione LC-MS (APCI) m/z 410 (MH+).
¹H NMR (DMSO-d₆): δ 1.30 (3H, s); 1.54-1.62 (2H, m); 1.85-1.91 (2H, m); 2.21 (3H, s); 2.24 (3H, s); 2.97-3.03 (2H, m); 3.27-3.34 (3H, m); 3.45 (1H, d); 3.49-3.55 (1H, m); 6.97-7.04 (2H, m); 7.11 (1H, s); 7.98 (1H, s); 10.70 (1H, s).

(5S)-5-{([4-(5-chloropyridin-2-yl)piperidin-1-yl]sulfonyl}-5-methylimidazolidine-2,4-dione LC-MS (APCI) m/z 387 (MH+).
¹H NMR (DMSO-d₆): δ 10.72 (1H, s); 8.54 (1H, d); 8.01 (1H, s); 7.86 (1H, dd); 7.38 (1H, d); 3.61 (2H, bt); 3.50, 3.32 (1H each, ABq, J=14.9 Hz); 2.96-2.76 (3H, m); 1.92 (2H, brd); 1.77-1.62 (2H, m); 1.33 (3H, s).

(5S)-5-[4-(5-Benzyloxy-pyridin-2-yloxy)-piperidine-1-sulfonylmethyl]-5-methyl-imidazolidine-2,4-dione LC-MS (APCI) m/z 475 (MH+).
¹H NMR (DMSO-d₆): δ 10.73 (1H, s); 8.01 (1H, s); 7.90 (1H, d, J=3.13 Hz); 7.48-7.30 (6H, m); 6.76 (1H, d, J=8.97 Hz); 5.10 (2H, s); 5.05-4.98 (1H, m); 3.51 (1H (from ABq), J=14.84 Hz); 3.40-3.30 (3H, m); 3.15-3.07 (2H, m); 2.07-1.95 (2H, m); 1.74-1.64 (2H, m); 1.33 (3H, s).

(5S)-5-[4-(6-Chloro-pyridine-3-yloxy)-piperidine-1-sulfonylmethyl]-5-methyl-imidazolidine-2,4-dione LC-MS (APCI) m/z 403 (MH+).
¹H NMR (DMSO-d₆): δ 10.74 (1H, s); 8.17 (1H, d, J=3.10 Hz); 8.61 (1H, s); 7.56 (1H, dd, J=3.18, 8.80 Hz); 7.44 (1H, d, J=8.77 Hz); 4.67-4.59 (1H, m); 3.52, 3.35 (2H, ABq, J=115.22 Hz); 3.39-3.28 (2H, m); 3.17-3.08 (2H, m); 2.03-1.93 (2H, m); 1.77-1.67 (2H, m); 1.33 (3H, s).

(5S)-5-[4-(5-Hydroxy-pyridin-2-yloxy)-piperidine-1-sulfonylmethyl]-5-methyl-imidazolidine-2,4-dione LC-MS (APCI) m/z 385 (MH+).
¹H NMR (Methanol-d₄): δ 7.73 (1H, d, J=3.01 Hz); 7.53 (1H, dd, J=3.11, 9.03 Hz); 7.04 (1H, d, J=9.04 Hz); 3.80-3.67 (1H, m); 3.58, 3.41 (2H, ABq, J=15.04 Hz); 3.53-3.42 (2H, m); 3.36-3.18 (2H, m); 2.17-2.02 (2H, m), 1.96-1.81 (2H, m); 1.48 (3H, s).

(5S)-5-[4-(4-Chloro-phenylsulfanyl)-piperidine-1-sulfonylmethyl]-5-methyl-imidazolidine-2,4-dione LC-MS (APCI) m/z 418 (MH+).
¹H NMR (DMSO-d₆): δ 10.74 (1H, s); 8.00 (1H, s); 7.45-7.39 (4H, m); 2.97-2.89 (2H, m); 2.00-1.91 (2H, m); 1.56-1.45 (2H, m); 1.31 (3H, s).

(5S)-5-[4-(4-Chloro-benzenesulfonyl)-piperidine-1-sulfonylmethyl]-5-methyl-imidazolidine-2,4-dione LC-MS (APCI) m/z 450 (MH+).
¹H NMR (DMSO-d₆): δ 10.73 (1H, s); 7.99 (1H, s); 7.86 (2H, d, J=8.77 Hz); 7.77 (2H, d, J=8.75 Hz); 3.66-3.54 (2H, m); 3.50-3.41 (1H, m); 3.44, 3.32 (1H each, ABq, J=14.63 Hz); 2.82-2.73 (2H, m); 1.97-1.88 (2H, m); 1.57-1.42 (2H, m); 1.30 (3H, s).

(5S)-5-[4-(4-Fluoro-phenylamino)-piperidine-1-sulfonylmethyl]-5-methyl-imidazolidine-2,4-dione LC-MS (APCI) m/z 385 (MH+).
¹H NMR (Methanol-d₄): δ 7.20-7.11 (4H, m); 3.84-3.71 (2H, m); 3.60-3.48 (1H, m); 3.56, 3.39 (1H each, ABq, J=14.96 Hz); 2.97-2.84 (2H, m); 2.10-2.00 (2H, m); 1.69-1.53 (2H, m); 1.46 (3H, s).

N-{3-[1-((4S)-4-Methyl-2,5-dioxo-imidazolidin-4-ylmethanesulfonyl)-piperidin-4-yloxy]-phenyl}-acetamide LC-MS (APCI) m/z 425 (MH+).
¹H NMR (DMSO-d₆): δ 10.74 (1H, s); 9.89 (1H, s); 8.01 (1H, s); 7.37-7.33 (1H, m); 7.21-7.14 (1H, m); 7.08-7.03 (1H, m); 6.65 (1H, dd, J=1.89, 8.04 Hz); 4.49-4.42 (1H, m); 3.51, 3.34 (1H each, ABq, J=14.73 Hz); 3.39-3.28 (2H, m); 3.18-3.08 (2H, m); 2.02 (3H, s); 2.00-1.92 (2H, m); 1.76-1.65 (2H, m); 1.33 (3H, s).

(5S)-5-[4-(4-Chloro-benzoyl)-piperazine-1-sulfonylmethyl]-5-methyl-imidazolidine-2,4-dione LC-MS (APCI) m/z 415 (MH+).
¹H NMR (DMSO-d₆): δ 10.75 (1H, s); 8.04 (1H, s); 7.54 (2H, d, J=8.38 Hz); 7.45 (2H, d, J=8.38 Hz); 3.79-3.55 (2H, bs); 3.56, 3.35 (1H each, ABq, J=14.84 Hz); 3.51-3.31 (2H, bs); 3.27-3.06 (4H, bs); 1.33 (3H, s).

1-(4S)-4-Methyl-2,5-dioxo-imidazolidine-4-ylmethanesulfonyl)-piperidine-4-carboxylic acid (4-fluoro-phenyl)-amide LC-MS (APCI) m/z 413 (MH+).
¹H NMR (DMSO-d₆): δ 10.74 (1H, s); 9.97 (1H, s); 8.02 (1H, s); 7.65-7.58 (2H, m); 7.16-7.09 (2H, m); 3.62-3.52 (2H, m); 3.49, 3.33 (1H each, ABq, J=14.94 Hz); 2.87-2.77 (2H, m); 2.48-2.39 (1H, m); 1.91-1.84 (2H, m); 1.70-1.57 (2H, m); 1.33 (3H, s).

(5S)-5-[4-(5-Bromo-pyridin-2-yloxy)-piperidine-1-sulfonylmethyl]-5-methyl-imidazolidine-2,4-dione LC-MS (APCI) m/z 447, 449 (MH+).
¹H NMR (DMSO-d₆): δ 10.73 (1H, s); 8.28 (1H, d, J=2.64 Hz); 8.01 (1H, s); 7.91 (1H, dd, J=2.60, 8.84 Hz); 6.83 (1H, d, J=8.79 Hz); 5.12-5.05 (1H, m); 3.52, 3.35 (1H each, ABq, J=14.85 Hz); 3.41-3.34 (2H, m); 3.17-3.08 (2H, m); 2.06-1.97 (2H, m); 1.78-1.67 (2H, m); 1.33 (3H, s).

(5S)-5-[4-(5-(4-Fluoro-phenyl)-pyridin-2-yl)-piperazine-1-sulfonylmethyl]-5-methyl-imidazolidine-2,4-dione LC-MS (APCI) m/z 448 (MH+).
¹H NMR (DMSO-d): δ 10.75 (1H, s); 8.45 (1H, d, J=2.51 Hz); 8.02 (1H, s); 7.88 (1H, dd, J=2.57, 8.86 Hz); 7.70-7.62 (2H, m); 7.30-7.22 (2H, m); 6.98 (1H, d, J=8.94 Hz); 3.70-3.62 (4H, m); 3.55, 3.36 (1H each, ABq, J=14.73 Hz); 3.26-3.19 (4H, m); 1.32 (3H, s)

(5S)-5-[4-(5-(4-Methoxy-phenyl)-pyridin-2-yl)-piperazine-1-sulfonylmethyl]-5-methyl-imidazolidine-2,4-dione LC-MS (APCI) m/z 460 (MH+).

(5S)-5-[4-(5-(4-Chloro-phenyl)-pyridin-2-yl)-piperazine-1-sulfonylmethyl]-5-methyl-imidazolidine-2,4-dione LC-MS (APCI) m/z 464, 466 (MH+).

(5S)-5-[4-(5-(4-Trifluoromethoxy-phenyl)-pyridin-2-yl)-piperazine-1-sulfonylmethyl]-5-methyl-imidazolidine-2,4-dione LC-MS (APCI) m/z 514 (MH+).

(5S)-5-[4-(5-Furan-2-yl-pyridin-2-yl)-piperazine-1-sulfonylmethyl]-5-methyl-imidazolidine-2,4-dione LC-MS (APCI) m/z 420 (MH+).

(5S)-5-Methyl-5-(4-[5-(1H-pyrrol-2-yl)-pyridine-2-yl]-piperazine-1-sulfonylmethyl)-imidazolidine-2,4-dione LC-MS (APCI) m/z 419 (MH+).

(5S)-5-(4-[3,3']-Bipyridinyl-6-yl-piperazine-1-sulfonylmethyl)-5-methyl-imidazolidine-2,4-dione LC-MS (APCI) m/z 431 (MH+).

(4S)-4-(6-[4-(4-Methyl-2,5-dioxo-imidazolidin-4-ylmethanesulfonyl)-piperazine-1-yl]-pyridine-3-yl)-benzonitrile LC-MS (APCI) m/z 455 (MH+).

EXAMPLE 14

Compounds with the General Formula

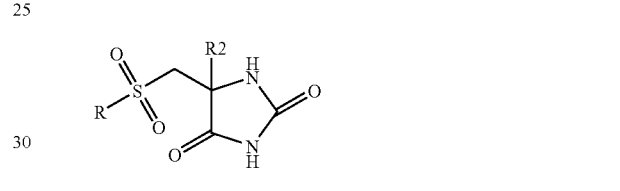

were synthesised according to the method described in Example 12.

| R | R2 | Analysis |
|---|----|----------|
| 5-chloro-pyridin-2-yloxy-piperidin-4-yl | 3-ethyl-1-methyl-5,5-dimethyl-imidazolidine-2,4-dione | m/z 543 (MH+)[1] |
| 5-trifluoromethyl-pyridin-2-yl-piperazin-1-yl | 3-ethyl-1-methyl-5,5-dimethyl-imidazolidine-2,4-dione | m/z 562 (MH+)[1] |
| 4-fluoro-phenyl-piperazin-1-yl | 3-ethyl-1-methyl-5,5-dimethyl-imidazolidine-2,4-dione | m/z 511 (MH+)[1] |
| 5-chloro-pyridin-2-yloxy-piperidin-4-yl-(2-benzyloxy-ethyl) | | m/z 523 (MH+)[1] |

-continued

| R | R2 | Analysis |
|---|---|---|
| 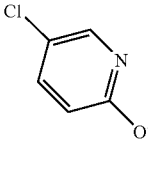 | 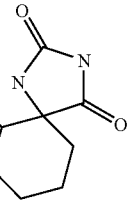 | m/z 443 (MH+)[1] |

[1]NMR available, see experimental part.

5-[({4-[(5-chloropyridin-2-yl)oxy]piperidin-1-yl}sulfonyl)methyl]-5-[(3,4,4-trimethyl-2,5-dioxoimidazolidin-1-yl)methyl]imidazolidine-2,4-dione The title compound was prepared as described in Example 12 from racemic {2,5-dioxo-4-[(3,4,4-trimethyl-2,5-dioxoimidazolidin-1-yl)methyl]imidazolidin-4-yl}methanesulfonyl chloride and 5-chloro-2-(piperidin-4-yloxy)-pyridine.

LC-MS (APCI) m/z 543 (MH+).

$^1$H NMR (DMSO-d$_6$): δ 1.28 (6H, s); 1.63-1.74 (2H, m); 1.95-2.05 (2H, m); 2.77 (3H, s); 3.14 (4H, d); 3.53-3.73 (3H, m); 4.14 (1H, q); 5.04-5.11 (1H, m); 6.85 (1H, d); 7.80 (1H, dd); 7.94 (1H, s); 8.19 (1H, d); 10.83 (1H, s).

The starting material was prepared as follows:

3-[3-(benzylthio)-2-oxopropyl]-1,5,5-trimethylimidazolidine-2,4-dione

Benzyl mercaptan (256 µl, 2.2 mmol) was stirred with cesium carbonate (712 mg, 2.2 mmol) in dimethyl formamide (5 ml) at room temperature for 1 hour. 3-(3-bromo-2-oxopropyl)-1,5,5-trimethylimidazolidine-2,4-dione (552 mg, 1.99 mmol) prepared as in WO99/06361 was added and the mixture stirred 18 hours at room temperature. The reaction mixture was treated with water, extracted into ethyl acetate (3×25 ml), the organic phases combined, brine washed and dried. The product was purified by silica chromatography, eluting with 50% ethyl acetate/iso-hexane to give 300 mg product.

LC-MS (APCI) m/z 321 (MH+).

$^1$H NMR (CDCl$_3$): δ 1.45 (6H, s); 2.91 (3H, s); 3.16 (2H, s); 3.70 (2H, s); 4.53 (2H, s); 7.22-7.33 (5H, m).

5-[(benzylthio)methyl]-5-[(3,4,4-trimethyl-2,5-dioxoimidazolidin-1-yl)methyl]imidazolidine-2,4-dione The title compound was prepared as described in the synthesis of 5-methyl-5-{[(phenylmethyl)thio]methyl}imidazolidine-2,4-dione in Example 12.

LC-MS (APCI) m/z 391 (MH+).

$^1$H NMR (DMSO-d$_6$): δ 1.28 (6H, s); 2.64 and 2.76 (2H, abq, J=14.2 Hz); 2.78 (3H, s); 3.54 & 3.64 (2H, abq, J=14.2 Hz); 3.73 (2H, s); 7.20-7.32 (5H, m); 7.98 (1H, s); 10.83 (1H, s).

{2,5-dioxo-4-[(3,4,4-trimethyl-2,5-dioxoimidazolidin-1-yl)methyl]imidazolidin-4-yl}methanesulfonyl chloride The title compound was prepared as described in the synthesis of [(4S) and (4R)-4-methyl-2,5-dioxoimidazolidin-4-yl]methanesulfonyl chloride in Example 12.

$^1$H NMR (CD$_3$OD): δ 1.38 (6H, s); 2.89 (3H, s); 3.81 and 3.92 (2H, abq, J=14.3 Hz); 4.61 (2H, s).

The following compounds were prepared as described in the synthesis of 5-[({4-[(5-chloropyridin-2-yl)oxy]piperidin-1-yl}sulfonyl)methyl]-5-[(3,4,4-trimethyl-Z 5-dioxoimidazolidin-1-yl)methyl]imidazolidine-2,4-dione.

5-[({4-[5-(trifluoromethyl)pyridin-2-yl]piperazin-1-yl}sulfonyl)methyl]-5-[(3,4,4-trimethyl-2,5-dioxoimidazolidin-1-yl)methyl]imidazolidine-2,4-dione LC-MS (APCI) m/z 562 (MH+).

$^1$H NMR (DMSO-d$_6$): δ 1.26 (6H, s); 2.76 (3H, s); 3.16-3.22 (4H, m); 3.48-3.76 (8H, m); 7.02 (1H, d); 7.81-7.76 (2H, m); 8.43 (1H, s); 10.83 (1H, s).

5-[4-(4-Fluoro-phenyl-piperazine-1-sulfonylmethyl]-5-[(3,4,4-trimethyl-2, dioxoimidazolidin-1-yl)methyl]imidazolidine-2,4-dione LC-MS (APCI) m/z 511 (MH+).

$^1$H NMR (DMSO-d$_6$): δ 1.28 (6H, s); 2.77 (3H, s); 3.10-3.16 (4H, m); 3.21-3.26 (4H, m); 3.48-3.71 (4H, m); 6.95-7.09 (4H, m); 7.88 (1H, s); 10.84 (1H, bs).

5-[({4-[(5-chloropyridin-2-yl)oxy]piperidin-1-yl}sulfonyl)methyl]-5-{2-[(phenylmethyl)oxy]ethyl}imidazolidine-2,4-dione The title compound was prepared as described in the synthesis of 5-[({4-[(5-chloropyridin-2-yl)oxy]piperidin-1-yl}sulfonyl)methyl]-5-[(3,4,4-trimethyl-2,5-dioxoimidazolidin-1-yl)methyl]imidazolidine-2,4-dione starting from 5-Chloro-2-(piperidine-4-yloxy)-pyridine hydrochloride and (2,5-dioxo-4-{2-[(phenylmethyl)oxy]ethyl}imidazolidin-4-yl)methanesulfonyl chloride.

LC-MS (APCI) m/z 523 (MH+).

$^1$H NMR (DMSO-d$_6$): δ 1.37-1.79 (3H, m); 1.83-2.08 (4H, m); 3.00-3.56 (7H, m partially obscured by D$_2$O); 4.33-4.44 (2H, m); 5.01-5.12 (1H, m); 6.85 (1H, d); 7.21-7.36 (5H, m); 7.80 (1H, dd); 8.02 (1H, s); 8.19 (1H, d); 10.70 (1H, bs).

6-({4-[(5-chloropyridin-2-yl)oxy]piperidin-1-yl}sulfonyl)-1,3-diazaspiro[4.5]decane-2,4-dione LC-MS (APCI) m/z 443 (MH+).

The starting material was prepared as follows:

6-[(phenylmethyl)thio]-1,3-diazaspiro[4.5]decane-2,4-dione

Benzylmercaptan (937 mg, 7.5 mmol) was dissolved in 70 mL of THF. NaH (362 mg 60%, 9.0 mmol) was added and the slurry was stirred for some minutes. 2-chlorocyclohexanone (1.0 g, 7.5 mmol) was added and the reaction was stirred at rt over night. The solid was filtered of and the solvent was removed by rotary evaporation. Potassium cyanid (4 eq), $(NH_4)_2CO_3$ (8 eq) and 25 mL of ethanol was added. The reaction was stirred in a sealed vial at 80° C. over night. The suspension was filtered and the solid was recrystallised from DMSO and water to give the title compound as a white solid LC-MS (APCI) m/z 291 (MH+).

$^1$H NMR (DMSO-$d_6$): δ 1.21-1.81 (8H, m); 2.79 (1H, dd); 3.67-3.76 (2H, m); 7.18-7.32 (5H, m); 8.43 (1H, s); 10.68 (1H, s).

EXAMPLE 15

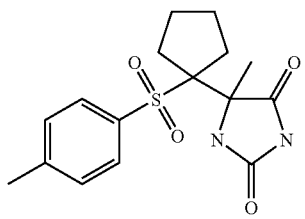

5-Methyl-5-(1-(toluene-4-sulfonyl)cyclopentyl)-imidazolidine-2,4-dione 1-(1-(Toluene-4-sulfonyl)-cyclopentyl))-ethanone (0.10 g, 0.38 mmol), potassium cyanide (0.049 g, 0.75 mmol), ammonium carbonate (0.18 g, 1.9 mmol), 50% ethanol in water (1.6 mL) were stirred in a sealed tube (2 mL volume) at 90° C. for 70 hours. The solution was acidified with 10% acetic acid to pH 6 and concentrated by rotary evaporation to half of its original volume upon which part of the product fell out. The solution and its solid contents were taken up in ethyl acetate, the aqueous phase was separated and washed twice with ethyl acetate. The combined organic phases were washed with brine, dried over anhydrous sodium sulfate, filtered and concentrated by rotary evaporation to give 0.74 g of a white solid. The crude product was dissolved in methanol (5 mL), concentrated with silica (1 g) by rotary evaporation and applied on a short silica column. Elution with ethyl acetate/n-heptane (1:2 and 2:1) gave 0.060 g (48%) of the title product as colourless needles.

LC-MS (APCI) m/z 337 (MH+).

$^1$H NMR (DMSO-$d_6$): δ 0.96-1.10 (1H, m); 1.32-1.44 (1H, m); 1.36 (3H, s); 1.47-1.58 (2H, m); 2.10-2.30 (4H, m); 2.40 (3H, s); 7.41 (2H, d, J=8 Hz); 7.72 (2H, d, J=8 Hz); 7.80 (1H, bs) and 10.7 (1H, bs).

$^{13}$C NMR (DMSO-$d_6$): δ 21.0, 22.60, 22.64, 26.1, 26.3, 30.8, 31.5, 64.1, 78.9, 129.2, 130.3, 135.3, 144.2, 156.0 and 176.2.

The starting material was prepared as follows:

1-Toluene-4-sulfonyl)-propan-2-one was prepared according to Crandall et al. J. Org. Chem. 1985, (8) 50, 1327-1329 from sodium p-toluenesulfinate dihydrate (4.2 g, 18 mmol), chloroacetone (1.0 mL, 12 mmol), n-tetrabutylammonium bromide (0.30 g) and water-benzene-acetone 4:3:3 (10 mL). Work-up and chromatography on silica of the crude using ethyl acetate/n-heptane (1:3 through 1:2) as eluent gave 2.4 g (95%) of the title product as an oil which crystallised on standing in the fridge.

LC-MS (APCI) m/z 213 (MH+).

$^1$H NMR (CDCl$_3$): δ 2.38 (3H, s); 2.42 (3H, s); 4.10 (2H, s); 7.35 (d2H, d, J=8 Hz); 7.74 (d, 2H, d, J=8 Hz).

$^{13}$C NMR (CDCl$_3$): δ 21.7, 31.4, 67.7, 128.0, 129.8, 135.5, 145.3 and 195.9.

1-(1-(Toluene-4-sulfonyl)-cyclopentyl))-ethanone 1-(Toluene-4-sulfonyl)-propan-2-one (0.10 g, 0.47 mmol), 1,4-diiodobutane (0.068 mL, 0.52 mmol), finely ground potassium carbonate (0.14 g, 1.0 mmol) and dry dimethylsulfoxide (0.80 mL) were stirred at 50° C. (oil bath temperature) for 22 hours. The heating was shut off and stirring was continued at 22° C. for 22 hours. The crude product was taken up in ethyl acetate, washed with water (5×50 mL) and brine (1×50 mL), dried over anhydrous sodium sulfate, filtered and concentrated by rotary evaporation. The oily residue was chromatographed on silica using ethyl acetate/n-heptane (1:4 through 1:3) to give 0.10 g (80%) of the title product as a colourless oil.

LC-MS (APCI) m/z 267 (MH+).

$^1$H NMR (CDCl$_3$): δ 1.52 (2H, m); 1.77 (2H, m); 2.26 (2H, m); 2.37 (2H, m); 2.42 (3H, s); 2.48 (3H, s); 7.30 (2H, d, J=8 Hz) and 7.60 (2H, d, J=8 Hz).

$^{13}$C NMR (CDCl$_3$): δ 21.7, 25.4, 28.0, 31.3, 83.9, 129.4, 129.5, 133.2, 145.0 and 202.5.

We claim:

1. A compound of the formula II or a pharmaceutically acceptable salt or an in vivo hydrolysable ester thereof

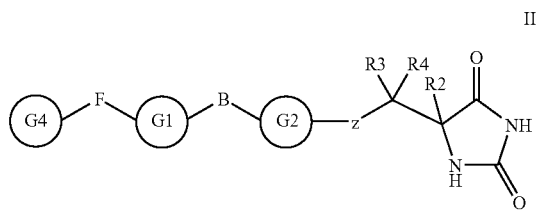

wherein
each of G1, G2 and G4 is a monocyclic ring structure comprising each of up to 7 ring atoms independently selected from cycloalkyl, aryl, heterocycloalkyl or heteroaryl, with each ring structure being independently optionally substituted by one or two substituents independently selected from halogen, hydroxy, haloalkoxy, amino, N-alkylamino, N,N-dialkylamino, cyano, nitro, alkyl, alkoxy, alkyl sulfone, haloalkyl sulfone, alkylcarbamate, alkylamide, wherein any alkyl radical within any substituent may itself be optionally substituted with one or more groups selected from halogen, hydroxy, amino, N-alkylamino, N,N-dialkylamino, cyano, nitro, alkoxy, haloalkoxy, aryloxy, heteroaryloxy, carbamate;
Z is SO$_2$;
each of B and F is independently selected from a direct bond, O, (C1-6)alkyl, (C1-6)heteroalkyl, alkynyl, CO, NCO, CON, NH, S;
R2 is selected from H, alkyl, hydroxyalkyl, alkoxyalkyl, aryloxy alkyl, aminoalkyl, (N-alkylamino)alkyl, (N,N-dialkylamino)alkyl, amidoalkyl, thioalkyl cycloalkyl-alkyl, alkyl-cycloalkyl, arylalkyl, alkylaryl, alkyl-heteroaryl, heteroalkyl, heterocycloalkyl-alkyl, alkyl-heterocycloalkyl, heteroaryl-alkyl, heteroalkyl-aryl;

R3 and R4 are independently selected from H or (C1-3) alkyl;

Optionally R2 and R3 may join to form a ring comprising up to 7 ring atoms, or R2 and R4 may join to form a ring comprising up to 7 ring atoms, or R3 and R4 may join to form a ring comprising up to 7 ring atoms.

2. A compound of the formula II as claimed in claim 1 or a pharmaceutically acceptable salt or an in vivo hydrolysable ester thereof, wherein R2 is alkyl, aminoalkyl, alkyl-heteroaryl, alkyl-heterocycloalkyl or heteroaryl-alkyl.

3. A pharmaceutical composition which comprises a compound of the formula II as claimed in claim 1 or a pharmaceutically acceptable salt or an in vivo hydrolysable ester thereof and a pharmaceutically acceptable carrier.

* * * * *